(12) United States Patent
Choi et al.

(10) Patent No.: US 11,738,078 B2
(45) Date of Patent: Aug. 29, 2023

(54) SEVERE FEVER WITH THROMBOCYTOPENIA SYNDROME VIRUS

(71) Applicant: I.D.BIO., Cheongju-si (KR)

(72) Inventors: Yeo-Jeong Choi, Cheongju-si (KR); Su-Jin Park, Cheongju-si (KR); Young-Il Kim, Daejeon (KR); Min-Ah Yu, Sejong (KR)

(73) Assignee: I.D.BIO., Cheongju-si (KR)

( * ) Notice: Subject to any disclaimer, the term of this patent is extended or adjusted under 35 U.S.C. 154(b) by 107 days.

(21) Appl. No.: 17/050,602

(22) PCT Filed: Apr. 23, 2019

(86) PCT No.: PCT/KR2019/004857
§ 371 (c)(1),
(2) Date: Oct. 26, 2020

(87) PCT Pub. No.: WO2019/208995
PCT Pub. Date: Oct. 31, 2019

(65) Prior Publication Data
US 2021/0121557 A1    Apr. 29, 2021

(30) Foreign Application Priority Data
Apr. 25, 2018  (KR) .................. 10-2018-0047865

(51) Int. Cl.
| *A61K 39/12* | (2006.01) |
| *A61P 31/12* | (2006.01) |
| *G01N 33/569* | (2006.01) |
| *A61K 39/00* | (2006.01) |

(52) U.S. Cl.
CPC .............. *A61K 39/12* (2013.01); *A61P 31/12* (2018.01); *G01N 33/569* (2013.01); *A61K 2039/5252* (2013.01); *A61K 2039/6056* (2013.01)

(58) Field of Classification Search
None
See application file for complete search history.

(56) References Cited

FOREIGN PATENT DOCUMENTS

| KR | 10-2015-0042419 A | 4/2015 |
| KR | 10-2016-0054161 A | 5/2016 |

OTHER PUBLICATIONS

Gen Bank Accession: ASW22984, RNA-dependent RNA polymerase [Severe fever with thrombocytopenia syndrome virus], 2017.*
Gen Bank Accession ASW22984, RNA-dependent RNA polymerase [Severe fever with thrombocytopenia syndrome virus], Sep. 5, 2017.*
Gen Bank Accession ASW22987, membrane glycoprotein polyprotein [Severe fever with thrombocytopenia syndrome virus], Sep. 5, 2017.*
Gen Bank Accession KY789438, Severe fever with thrombocytopenia syndrome virus isolate CB3 segment M, complete sequence, Sep. 5, 2017.*
Gen Bank Accession KY789435, Severe fever with thrombocytopenia syndrome virus isolate CB3 segment L, complete sequence, Sep. 5, 2017.*
GenBank Accession KY789441, Severe fever with thrombocytopenia syndrome virus isolate CB3 segment S, complete sequence, Sep. 5, 2017.*
Brennan et al., Reverse Genetics System for Severe Fever with Thrombocytopenia Syndrome Virus, 2015, vol. 89, No. 6, pp. 3026-3037.*
Seok-Min Yun et al., "Molecular genomic characterization of tick and human-derived severe fever with thrombocytopenia syndrome virus isolates from South Korea", PLOS Neglected Tropical Diseases, Sep. 22, 2017, pp. 1-15.
Yonggeng Fu et al., "Phylogeographic analysis of severe fever with thrombocytopenia syndrome virus from Zhoushan Islands, China: implication for transmission across the ocean", Scientific Reports, Jan. 2016, pp. 1-8, vol. 6, No. 19563.
Tomoki Yoshikawa et al., "Phylogenetic and Geographic Relationships of Severe Fever With Thrombocytopenia Syndrome Virus in China, South Korea, and Japan", Phylogenetic Analysis of SFTSV, Sep. 15, 2015, pp. 889-898, vol. 212.
International Search Report for PCT/KR2019/004857 dated Aug. 19, 2019 (PCT/ISA/210).

* cited by examiner

*Primary Examiner* — Benjamin P Blumel
(74) *Attorney, Agent, or Firm* — Sughrue Mion, PLLC

(57) ABSTRACT

The present invention relates to a novel genotype of severe fever with thrombocytopenia syndrome viruses and use thereof as an immunogenic composition. The severe fever with thrombocytopenia syndrome viruses of the present invention are genetically different from conventional severe fever with thrombocytopenia syndrome viruses and are novel viruses taxonomically belonging to three sub-groups of genotype B. In view of the vaccine property that specific genotype viruses alone show only limited protective potential, the novel viruses of the present invention may be advantageously used as a vaccine having excellent cross-immunogenicity for SFTSV.

5 Claims, 6 Drawing Sheets
Specification includes a Sequence Listing.

SEQUENCE LISTING

<160> NUMBER OF SEQ ID NOS: 24

<210> SEQ ID NO 1
<211> LENGTH: 6255
<212> TYPE: DNA
<213> ORGANISM: Unknown
<220> FEATURE:
<223> OTHER INFORMATION: severe fever thrombocytopenia syndrome virus
      B-1 L gene

<400> SEQUENCE: 1
atggacttgg aagtgctttg tggtaggata aacgtggaga atgggctgtc tcttggagaa      60
ccaggcctgt acgaccaaat ctacgacagg ccagggctgc cagacctaga tgtgactgtc     120

```
gatgccacag gtgtgacagt ggacataggg gctgtgccag actcagcatc acaactgggc      180
tcatcaatca atgctgggtt gatcacaatc cagctctctg aagcatataa gatcaatcat      240
gacttcacat tttctggcct gtcaaagaca acagaccgac gcctctcaga ggtattcccc      300
attacccatg atggttctga tgggatgacc cctgatgtga tccacaccag attggatgga      360
actattgtgg tggttgaatt ttcaaccact aggagccata acattggggg cctggaggca      420
gcatatagga caaagataga aaaatatagg gacccaatct caaggcgtgt tgatatcatg      480
gagaacccga gagtcttctt tggtgttatt gtagtctcgt caggaggggt tctgtccaac      540
atgcccctga ctcaggatga ggcagaggag ctcatgtaca ggttctgcat agccaatgaa      600
atctacacta aggctagatc tatggatgca gacattgagc tacagaagag tgaagaagag      660
cttgaggcta tcagcagggc actttcattc ttcagtttgt tcgagcctaa cattgaaaga      720
gtggaaggaa cattccccaa ttcagaaatt gagatgctgg aacagtttct ctcaacacca      780
gctgatgttg acttcatcac caagaccctc aaagcaaaag aggtggaggc ctatgctgat      840 cttttgtgaca gccactacct aaagcctgaa aaaaccattc aggagcgtct agagatcaat      900
agatgtgagg ctattgacaa aactcaggac ctcctagctg gcctacatgc aaggagcaac      960
aagcaaacat cattgaatcg agggacagtc aaactcccgc cctggctgcc aaagccatca     1020
agtgagtcaa tagacatcaa gaccgactca ggctttggtt ccttaatgga tcatggcgca     1080
tatggtgagc tatgggcaaa gtgccttcta gatgtctcgt taggcaatgt ggagggggta     1140
gtcagtgacc ctgcaaaaga gcttgacatt gctatctctg atgacccaga aaaagacacc     1200
cccaaagagg caaagataac ctataggcga ttcaagcctg ccttaagttc aagtgcccgg     1260
caagaatttt ctctccaagg agtggagggg aagaagtgga agagaatggc agcaaaccag     1320
aagaaagaga aggagtccca tgagacattg agccctttct tggatgttga agacattggg     1380
gatttcctga cattcaacaa tcttcttgca gattcgaggt atggagatga gtccatccag     1440
agagctgtgt caatcttgtt ggaaaaggca tctgccatgc aggacacaga gctcactcat     1500
gctctcaacg actcattcaa gaggaaccta agcagcaatg tggttcagtg gtcccttttgg     1560 gtttcctgtt tggcgcagga gctagctagt gctctgaagc agcactgcag ggctggtgag     1620
ttcatcatca agaagctgaa gttctggcct atctatgtca ttatcaagcc gaccaaatcg     1680
tcatctcaca tcttctacag cttagggatc cgcaaggctg acgtgacaag gaggctcact     1740
ggtagagtct tctctgacac cattgatgca ggggaatggg agctaacaga gttcaaaagc     1800
ctgaagacat gtaagctcac gaaccttgtc aacttaccat gcaccatgct gaactcaata     1860
gctttctgga gagagaagct gggcgtggct ccatggctgg tccggaagcc ttgttcagag     1920
ctcagggagc aggtgggcct gaccttcctg atcagtctgg aggacaagtc taagactgag     1980
gagatcatca ccttgacaag gtacacccag atggagggct ttgtctctcc tcccatgctg     2040
cccaaacccc aaaagatgct agggaaactg gatggacctt tgagaaccaa gctacaggtt     2100
tacctcctca ggaagcatct ggattgcatg gtgcgaattg cttctcagcc attcagccta     2160
atcccaagag aggggagagt agaatgggga ggaacattcc atgccatctc aggccggtcc     2220
acaaatcttg agaatatggt gaacagctgg tacattgggt actacaagaa caaagaggag     2280
tcaacagaac taaatgctct cggagaaatg tataagaaga ttgtggagat ggaagaggac     2340
aagcccagca gccctgagtt tctggggtgg ggggacactg attcccctaa gaagcatgaa     2400
ttctcacgga gcttcctgag agctgcttgc tcatctctga aagagaaat tgctcagcga     2460
```

```
catgaagac aatggaagca gaaccttgag gagcgagtcc tgagagagat tgggaccaag    2520
aacatcctgg accttgcatc catgaaggct actagcaact tttccaaaga ctgggagctc    2580
tactcagaag tccagaccaa agagtaccat aggtccaaac tgctggagaa gatggccaca    2640
ttgattgaga aggggttat gtggtacatt gatgctgtgg gtcaggcatg gaaggcagtt     2700
ctggatgacg ggtgcatgcg aatctgtctc ttcaaaaaga atcagcatgg tggcctcaga    2760
gagatctacg ttatggatgc aaatgcccgg ctcgtgcagt ttggggttga gaccatggct    2820
aggtgtgtct gtgagctgag cccacatgag actgttgcca accctaggct caagaattcc    2880
atcatagaga accatgggct gaagtcagcc cgtagtcttg ccctggctc tataaacata     2940
aactcatcca atgatgccag gaagtggaat caggggcact acacaacaaa gctagctcta    3000
gttctttgtt ggttcatgcc agccaaattc cacagattca tttgggctgc catttccatg    3060
tttcggagaa aaagatgat ggtggaccta aggtttttag ctcacctcag ttctaaatct     3120
gagtctaggt catctgatcc atttagggaa gcaatgacag acgccttcca tgcaataggg    3180
gaagtctcat ggatggacaa agggcgaact tacataaaga cagagacagg tatgatgcag    3240
ggtatactgc actttacatc cagcctcctc cactcttgtg ttcagagctt ttacaagtct    3300
tatttcgtct cgaaactcaa ggagggctac atgggagaaa gcatcaatgg ggtggtggat    3360
gtcatagaag gctctgacga ctcagcgatc atgatcagca tacgccccaa gtcagacatg    3420
gatgaagtcc gatcaaggtt ctttgttgct aacttactcc actctgtaaa gttcttgaac    3480
cctttgtttg ggatctactc atcagagaaa tcaacagtga acacagtgta ttgtgtcgag    3540
tataactctg aattccattt ccacaggcac ttggttcgac ccacactgag atggatagca    3600
gcatctcacc aaatctcaga gactgaggcc cttgcaagca ggcaagagga ttattcaaac    3660
cttctaaccc agtgcttgga gggagggggcc tcattctctc ttacctacct catacagtgc    3720
gctcagctcc tgcaccacta catgcttcta ggactatgct acacccctt gtttggaact     3780
ttcatgggga tgctgatatc agacccagat ccagccctag ggttcttcct catggacaac    3840
cctgcattcg caggaggagc aggatttaga ttcaatctgt ggagagcctg caagactaca    3900
gaccttgggc ggaagtatgc atattatttt aatgagatac agggtaaaac aaagggagat    3960
gaggactaca gagctctgga cgccacatca ggaggaaccc tcagccactc tgttatggtg    4020
tactgggggg acaggaagaa gtatcaggcc ttattgaaca ggatgggcct tcctgaggac    4080
tgggtggagc agatagatga gaatcccggt gtcctttaca ggagagctgc caacaagaag    4140
gaactactct aaaactggc agagaaggtt cattcacctg gtgtgactag cagcctgagt     4200
aaagggcatg tagtgcctcg ggtggtggca gcaggagtat accttctctc acgccattgc    4260
tttcgcttta gctcaagcat ccatggaagg ggctcagcac agaaggctag ccttataaaa    4320
ctgttgatga tgtcttctgt ttctgccatg aagcatgggg gctcactaaa ccctaatcag    4380
gagcgaatgc tcttccctca ggctcaagag tatgacagag tatgcacatt gcttgaggag    4440
gttgaacacc taacagggaa atttgttgtt agggagagga acattgtcag gagccgcata    4500
gacttgttcc aagagccagt ggacttgcgg tgcaaggcag aagatctggt gtcagaggtg    4560
tggtttggcc tgaaaaggac taaacttgga ccccgtctcc tcaaggaaga gtgggacaaa    4620
cttagggcct catttgcatg gctgagcaca gacccatctg aaacattgag ggatggtcct    4680
tttcttagcc atgtgcagtt taggaacttc atagcccacg ttgatgccaa atcaagatca    4740
gtcaggctcc taggtgcccc cgtaaagaag tcaggtgggg tcaccactat aagccaagta    4800
gtcagaatga acttcttccc aggtttttagc ctagaagctg agaagagctt agacaatcag    4860
```

```
gaaagacttg agagcatctc catcctcaag catgtcttgt tcatggtctt gaatggccca    4920
tacactgagg agtacaagct ggaaatgatc atagaggcct tctctactct tgtgataccr    4980
cagccatcag aggtcatcag gaaatcaagg accatgactt tgtgcctctt atcaaattac    5040
ttgtctagta ggggtgggtc cattctagac cagattgaga gggcacagtc aggcactcta    5100
gggggcttca gcaagcccca gaagactttc attaggccag gaggtggtat cggctacaag    5160
ggaaagggtg tgtggactgg agtgatggag gacacccatg ttcaaattct gatagatgga    5220
gatgggacta gtaactggct tgaggagatc aggctcagta gtgatgccag acttatgat    5280 gtcattgagt ccatccgaag gttatgtgat gacctcggga tcaacaacag ggtggcatct    5340
gcatatagag gccattgcat ggttaggctg agtggattca agatcaagcc agcatcaagg    5400
actgatggct gcccagtcag gattatggaa aggggcttca ggatcaggga actccaaaac    5460
ccagatgagg tcaagatgag agtgagaggt gacatcctca acctctctgt caccattcaa    5520
gaaggaaggg tcatgaacat tctaagctac aggccgagag acactgatat atcagaatca    5580
gccgcagcat atctctggag caatcgagac ctcttctcct ttgggaagaa ggagccatcc    5640
tgcagctgga tctgcttgaa aactcttgac aattgggcct ggtcacatgc ctcagttctc    5700
ctggcaaatg ataggaagac ccaaggcatt gataataagg ctatggggaa cattttcagg    5760
gactgtctcg agggttctct tagaaagcaa gggctgatga ggtcaaagct cacagagatg    5820
gtggagaaga atgtagttcc tttaacaact caagagcttg tcgacatcct ggaggaggac    5880
atagactttt cagatgtcat agctgtggaa ctctcagagg gatcacttga tattgaatcc    5940
atctttgatg gggcacctat cttgtggtct gctgaggtgg aagagtttgg ggaaggagtg    6000
gtggctgtga gctattccag taagtactat catctaaccc tgatggacca agctgccatc    6060
acaatgtgtg cgatcatggg taaggaaggc tgtagagggc tccttactga aagagatgc    6120 atggcagcca tacgagagca ggtacggcca ttcctcatat tcctgcaaat ccctgaggat    6180
agcatttctt gggtgtctga tcagttctgc gactccaggg tcttgatga ggagagcacc    6240 attatgtggg gttga                                                     6255
```

<210> SEQ ID NO 2
<211> LENGTH: 3222
<212> TYPE: DNA
<213> ORGANISM: Unknown
<220> FEATURE:
<223> OTHER INFORMATION: severe fever thrombocytopenia syndrome virus B-1 M gene

<400> SEQUENCE: 2

```
atgatgaaag tcatctggtt ctcctctctg atctgcttag tcattcaatg cagtggggat      60
acgggtccaa tcatatgcgc agggcccatc cactcaaaca agagtgccaa catacccac     120 ctgcttggct actctgagaa gatttgtcag atagatcggc tgatacatgt ttcgtcatgg     180
ctgagaaacc attcacaatt tcagggctat gtggggcagc gaggtggacg ctctcaggta     240
agctattacc cagctgaaaa ctcttactca aggtggagtg gacttctaag cccctgtgat     300
gcagattggc ttgggatgct tgttgtgaag aaggccaaag gtctgatat gatagttcct     360 gggccttcat acaagggaaa agtcttttt gaacggccaa cttttgatgg atacgtaggc     420 tgggggctgtg gcagtgggaa gtcaaggaca gagtcagggg agctctgcag ctcagactca     480
gggaccagtt ccggtcttct gccctcagat agggttctct ggataggtga tgttgcttgc     540
cagcctatga cacccatccc tgaggagaca tttctggagc tgaagagttt tagccagagt     600
```

```
gaattcccag acatatgcaa aattgatggc attgtgttca accagtgtga gagtgagagt      660
ctacctcaac ccttagatgt tgcgtggatg gatgtaggcc actctcataa aatcatcatg      720
agggagcaca agactaaatg ggtacaagag agctcatcta aggattttgt gtgctacaag      780
gaagggactg ggccatgttc tgaatcagaa gaaaagactt gcaagaccag tggatcatgt      840 agggggggaca tgcagttttg caaggtggca ggttgtgaac atggggaaga agcatctgat      900
gccaagtgta gatgctcact agtgcacaag cccgggaaag ttgttgtgtc atatggaggg      960
atgcgtgtca gaccaaagtg ttatggcttc tccagaatga tggcaacact agaggtgaac     1020
ccaccagagc aaaggattgg ccaatgcact ggctgccatc ttgaatgcat aaatgggggt     1080
gtgaggctaa tcactctgac tagtgagctc aagtcagcta ctgtctgtgc ttcccacttt     1140
tgtagttctg ccacaagtgg caagaaaagc acggagatta aatttcactc agggtcatta     1200
gttgggaaaa caacaataca cgtcaaaggg gctttggtgg atggaactga attcacattt     1260
gagggcagtt gcatgttccc agatggttgt gacgcagtgg actgcacatt ctgtcgtgag     1320
tttctaaaaa atcctcagtg ctaccctgca aagaaatggc tgttcatcat tattgtcatc     1380
ctccttggat atgcaggcct catgctactt accaatgtcc ttaaggcaat cggggtttgg     1440
ggatcatggg tcatagctcc agtgaagcta atgtttgcca tcataaagaa actgatgaga     1500
tctgtgagct gcttgatggg gaaattaatg gataggggaa ggcaagtgat ccatgaagaa     1560 atagggggaga atagagaggg caaccaagat gatgttagga tcgagatggc aagacccaga     1620
agggtaaggc attggatgta ctcacctgtc atcctgacta ttctagcaat tgggcttgcc     1680
gagggctgcg atgagatggt ccatgctgac tccaaacttg tttcgtgcaa gcaagggagc     1740
ggaaacatga aggaatgtgt cacaactggg agggcactcc ttcctgcggt gaacccagga     1800
caagaggcat gtctgcactt cacggcacct gggagtccgg actcaaaatg tctcaaaatt     1860
aaggtcaaga ggattaacct aaaatgtaag aagtcatcat catattttgt tcctgatgct     1920
cggtctaggt gtacatctgt gaggagatgt cgctgggcag gagactgcca gtctgggtgc     1980
ccctctcatt tcacgtccaa ctccttctct gatgattggg caggtaaaat ggacagggca     2040
ggtctaggat tcagtgggtg ctctgatgga tgtggaggag cagcctgcgg ctgctttaat     2100 gcagccccctt catgcatctt ttggaggaaa tgggtagaga accgcatgg gatcatctgg     2160 aaagtatctc catgtgctgc atgggtccca tcagcagtca tagagctaac aatgccctca     2220
ggggaagtga ggacattcca ccccatgagc ggcatcccta cacaagtctt caagggtgtg     2280
agtgtgacgt acttaggctc agatatggag gtgtctggct tgactgacct gtgtgagata     2340
gaagagctca agtccaagaa gctggcatta gccccctgca atcaggctgg catggggtt     2400 gtaggcaagg ttggagagat acagtgcagt agcgaggaaa gtgcccgtac cataaaaaaa     2460
gatgggtgta tatggaatgc tgaccttgtg ggcatagagc tacgagtgga tgacgctgtg     2520
tgctactcta agatcactag tgtggaggca gttgcaaact actctgccat cccaccacct     2580 attgggggc tgaggtttga gagaagccat gacagccagg gtaaaatatc tggtagcccc     2640
ttagatataa cagccataag agggtctttt tcagttaatt atagaggcct tcgactgagc     2700
ctctcagagg ttactgctac ttgcacagga gaggtgacga atgtgagtgg gtgttactct     2760
tgcatgacag gcgccaaagt ctccatcaaa ctgcatagca gcaaaaatag cactgcccat     2820
gtaagatgca aaggggatga gacagcattc agtgtcctag tgggagttca tagctatact     2880
gtcagtctca gctttgacca tgcagtggtc gatgagcagt gccagctgaa ctgtggaggg     2940
```

| catgagagtc aagtgactct aaaaggcaac ctcatcttcc tggatgtccc aaaatttgtg | 3000 |
| gatggcagct atatgcagac atatcatagt tctgtgccca caggggccaa catcccaagc | 3060 |
| cctacagact ggctgaatgc cttgttcggc aatgggctga gtaggtggat tctgggggta | 3120 |
| ataggggttc tactgggggg attggctctc tttttcttaa tcatgtctct gttcaaattg | 3180 |
| ggaacaaaac aggtatttcg atcaaggacg aagctggctt aa | 3222 |

<210> SEQ ID NO 3
<211> LENGTH: 738
<212> TYPE: DNA
<213> ORGANISM: Unknown
<220> FEATURE:
<223> OTHER INFORMATION: severe fever thrombocytopenia syndrome virus
      B-1 NP gene

<400> SEQUENCE: 3

| atgtcagagt ggtccaggat tgcagtggag tttggtgagc agcagctcaa tttgacggag | 60 |
| cttgaggact tcgcgagaga gctggcctat gaaggccttg atcctgcttt gatcatcaag | 120 |
| aagctgaagg agacaggtgg ggatgattgg gtgagggata caaagttcat cattgtcttt | 180 |
| gccctgactc gaggcaataa gattgtcaag gcatcaggga aaatgtcaaa ctcagggtct | 240 |
| aagaggttga tggcactcca agagaagtat ggactggttg agagggcaga aaccaggctc | 300 |
| tcaatcactc ctgtgagggt ggcacagagc ctacccactt ggacatgtgc tgctgcagca | 360 |
| gccttaaagg agtatcttcc agttgggcca gctgtcatga acctgaaggt cgagaattat | 420 |
| cctccagaga tgatgtgcat ggcctttggg tccctgattc aactgcgggg ggtgtcagaa | 480 |
| gctacaacga agaccctgat ggaggcctac tctctgtggc aagatgcctt cacaaagact | 540 |
| atcaatgtga agatgcgcgg agccagtaag acagaggttt acaactcctt cagggatcct | 600 |
| ctccatgctg ctgtgaactt cgtctttttc ccccaagatg ttcgggtgaa gtggctgaag | 660 |
| gccaagggaa tccttggccc agatggggtc cccagcagag ctgctgaggt tgctgctgct | 720 |
| gcttacagaa acctgtaa | 738 |

<210> SEQ ID NO 4
<211> LENGTH: 882
<212> TYPE: DNA
<213> ORGANISM: Unknown
<220> FEATURE:
<223> OTHER INFORMATION: severe fever thrombocytopenia syndrome virus
      B-1 NS gene

<400> SEQUENCE: 4

| atgtcgctga gcaaatgctc caacgttgac ctcaaatctg tggcaatgaa tgccaacact | 60 |
| gtcaggcttg agccatctct aggagagtac cccactctta ggagagacct cgttgaatgc | 120 |
| tcttgtagtg tgttgactct atcaatggtt aagaggatgg gcaagatgac caacacagta | 180 |
| tggttgtttg gtaacccaaa aaatcctctt caccagcttg agcctggact cgagcagctg | 240 |
| ttggacatgt actacaagga catgaggtgc tactcccaga gagagctgag tgctcttagg | 300 |
| tggcctagtg ggaagccatc tgtatggttc ctgcaggcag ctcatatgtt cttctccatc | 360 |
| aagaacagct gggcaatgga aaccggcaga gagaattggc ggggcctctt ccacaggata | 420 |
| acaaaaggca aaaagtatct tttttgaagga acatggatat tggattctct tgaggccata | 480 |
| gagaagcgaa ggcttagact tgggctacct gagatcctaa taactggact atccccgatt | 540 |
| ctggatgtgg ccctcctcca gatagagtca cttgcaaggc taagaggcat gagcttgaac | 600 |
| caccacttat tcacatcttc ctcattgcgt aagcctttgt tggactgttg ggacttcttt | 660 |

```
attcctatcc ggaaaaagag gacagatggc tcatacagta tcttggatga ggatgatgaa    720
cttggggtcc ttcaaggtta cccatatctg atggcacact atttgaatag gtgcccattc    780
cacaacctca tcaggtttga tgaagagctg agaactgcag ccctaaacac catctgggga    840
agagattggc cggccattgg tgacctcccg aaggaggtct aa                       882
```

<210> SEQ ID NO 5
<211> LENGTH: 6255
<212> TYPE: DNA
<213> ORGANISM: Unknown
<220> FEATURE:
<223> OTHER INFORMATION: severe fever thrombocytopenia syndrome virus
      B-2 L gene

<400> SEQUENCE: 5

```
atgaacttgg aagtgctttg tggtaggata aacgtggaga atgggctgtc tcttggagaa     60
ccaggcctgt acgaccaaat ctacgacagg ccagggctgc cagacctaga tgtgactgtc    120
gatgccacag gtgtgacagt ggacataggg gctgtaccag actcagcatc acaactgggc    180
tcatcaatca atgctgggtt gatcacaatc cagctctctg aagcatataa gatcaatcat    240
gacttcacat tttctggcct gtcaaagaca acagaccgac gcctctcaga ggtattcccc    300
attacccatg atggttcaga tgggatgacc cctgatgtga ttcataccag attggatgga    360
accattgtgg tggttgaatt ttcaaccact aggagccata acattggggg cctggagacg    420
gcatatagaa caaagataga gaaatatagg gacccaatct caaggcgtgt tgatatcatg    480
gagaacccga gggtcttctt tggcgttatt gtagtctcgt caggaggggt tctatccaac    540 atgccctga ctcaggatga ggcagaggag ctcatgtaca ggttctgcat agccaatgag    600
atctacacca aggctagatc tatggatgca gacattgagc tacagaagag tgaagaagag    660
cttgaggcta ttagcagggc actgtcattc ttcagtttgt ttgagcctaa cattgaaaaa    720
gtggaaggaa cattccccaa ttcagaaatc gagatgctgg aacagtttct ttcaacacca    780
gctgatgttg acttcatcac taagacactc aaagcaaaag aggtggaggc ctatgctgat    840
ctttgtgaca gccactacct aaagcctgaa aaaaccattc aggagcggct agagatcaat    900
agatgtgagg ctattgataa aactcaggac ctcctagcta gcctgcatgc aaggagcaac    960
aaacaaacat cactgaatcg agggacagtc aaactcccgc cctggctacc aaagccatca   1020
agtgagtcaa tagacatcaa gaccgactca ggctttggtt ccttaatgga ccatggcgca   1080
tatggtgagc tgtgggcaaa gtgccttcta gatgtctcgc tggcaatgt ggagggggta   1140 atcagtgacc ctgcaaaaga acttgacatt gctatctctg atgatccaga aaagatacc   1200 cccaaagaag caaagataac ctataggcga ttcaagcctg ccttaagttc aagtgcccgt   1260 caggaattt ctctccaagg agtggaggga agaagtgga agagaatggc agcaaaccag   1320 aagaagaga aggagtccca tgaggcattg agccccttct tggatgttga ggacattggg   1380
gatttcctaa cattcaacaa tcttcttgca gattcaaggt atggagatga gtccgtccag   1440
agagctgtgt caatcctgtt ggagaaggca tctgccatgc aaaacacaga gctaactcat   1500
gccctcaatg actcattcaa gaggaaccta agcagtaatg tggttcagtg gtccctctgg   1560
gtctcctgtt tagcacagga gctagctagt gctctgaagc agcactgcag ggctggtgag   1620
ttcatcatca agaagttgaa gttctggcct atctatgtca tcatcaagcc gaccaaatcg   1680
tcttcccata tcttctacag cttagggatc cgcaaggctg atgtgacaag gaggctcact   1740
ggcagagtct tctctgacac cattgatgct ggggaatggg agctaacaga gttcaaaagc   1800
```

```
ctgaagacat gcaagctcac gaaccttgtc aacttaccat gcaccatgct gaactcaata    1860
gctttctgga gagagaagct gggcgtggct ccatggctgg ttcggaagcc ttgttcagag    1920
ctcagagagc aggtgggcct gaccttcctg atcagtctgg aggacaagtc taagactgag    1980
gagatcatca ccttgacaag gtacacccag atggagggct tgtctctcc tcccatgctg     2040 cctaagcccc aaaagatgct agggaaactg gatggacctt tgagaactaa gttacaggta    2100
tacctcctca ggaagcatct ggattgcatg gtgcgaattg cttctcagcc attcagccta    2160
atccctagag aggggagggt agaatgggga ggaacattcc atgccatctc aggccggtcc    2220
acaaaccttg agaatatggt gaacagctgg tacattgggt actacaagaa caaagaggag    2280
tcaacagagc taaatgctct cggagaaatg tataagaaga ttgtagagat ggaagaggac    2340
aagcccagta gccctgagtt tctagggtgg ggggacactg attcccctaa gaagcatgaa    2400
ttctcacgga gcttcctcag agctgcttgc tcatctctgg agagagaaat tgctcagcga    2460
catggaagac aatggaagca gaaccttgag gagcgtgtcc tgagagagat tgggaccaag    2520
aacatcctgg accttgcatc catgaaggct acaagcaact tttccaaaga ctgggagctc    2580
tactcagagg tccagaccaa agagtaccat aggtccaaac tgctggagaa gatggccaca    2640
ttgatagaga agggggttat gtggtacatt gatgctgtgg ccaggcatg gaaggcagtt    2700 ctagatgacg ggtgcatgcg aatctgtctc ttcaaaaaga atcagcatgg tggtctcaga    2760
gagatctacg ttatggatgc aaatgcccgg ctcgtgcagt ttggggttga gaccatggct    2820
aggtgtgtct gtgagttgag cccacatgag actgttgcca accctagact caagaattcc    2880
atcatagaga accatgggct gaagtcagcc cgtagtcttg gtcctggctc tataaacata    2940
aactcatcca atgacgccaa gaagtggaat caggggcact acacaacaaa gctagctcta    3000 gttcttttgtt ggttcatgcc agccaaattc cacagattca tttgggccgc catttccatg    3060
tttcggagaa aaaagatgat ggtggaccta aggttttttag ctcacctcag ttctaaatct    3120
gagtctaggt catctgaccc gtttagggaa gcaatgacag acgctttcca tggtaatagg    3180
gaagtctcat ggatggacaa agggcgaact tacataaaga cagagacagg aatgatgcag    3240
ggcatactgc actttacatc cagcctcctt cactcttgtg ttcagagctt ttacaagtct    3300
tatttcgtct cgaagcttaa ggagggctac atggggggaaa gcatcaatgg ggtggtggat    3360
gtcatagaag gctctgacga ctctgcgatc atgatcagca tacgccctaa gtcagacatg    3420
gatgaagtcc gatcaaggtt ctttgttgct aacttgctcc actctgtcaa gttcttgaac    3480
cctttgtttg gtatttactc atcagagaaa tcaacagtga acacagtgta ttgtgttgag    3540
tataactctg aattccactt ccacaggcac ttggtcagac ccacactgag atggatagca    3600
gcgtctcacc aaatctcaga gactgaagcc cttgcaagca ggcaagagga ttactccaac    3660
cttctaaccc agtgcttgga aggaggggcc tcattctctc ttacctacct tatacagtgc    3720
gctcagctcc tgcaccacta catgctccta ggactatgct tacatccctt gtttggaact    3780
ttcatgggga tgctgatatc agacccagat ccagccctag ggttcttcct catggacaac    3840
cctgcattcg cagggggagc aggatttagg ttcaatctgt ggagggcctg caagactaca    3900
gaccttgggc ggaagtatgc atattatttt aatgagatac agggtaaaac aaagggagat    3960
gaggattaca gagctctgga cgccacatcg ggaggaactc tcagccactc tgtcatggtg    4020
tactgggggg acaggaagaa gtatcaggcc ttattgaaca ggatgggcct tcctgaagac    4080
tgggtggagc agatagatga gaatcctgga gtcctttaca ggagagctgc caacaaaaag    4140
```

```
gaactactct taaaactggc agagaaggtt cattcaccag gtgtgactag cagcctgagt    4200
aaagggcatg tagtgcctcg ggtggtggca gcaggagtat accttctctc acgccactgc    4260
tttcgcttta gctcaagtat ccatggaagg ggctcagcac agaaggctag tcttataaaa    4320
ctgctgatga tgtcttctat ttctgccatg aagcacgggg gctcactaaa ccctaatcag    4380
gagcgaatgc tcttccctca ggcccaggag tatgacagag tatgcacatt gcttgaggaa    4440
gttgagcacc taacagggaa atttgttgtt agggagagaa acattgtcag gagccgtata    4500
gacttgttcc aagagccagt ggacttgcgg tgcaaggcag aagatctggt gtcagaggtg    4560
tggtttggcc tgaaaaggac taagcttgga ccccgtctcc tcaaggaaga gtgggacaaa    4620
cttagggcct catttgcatg gctgagcaca gacccatctg aaacattgag ggatggccct    4680
tttcttagcc atgtgcagtt tagaaacttc atagcccatg ttgatgccaa atcaagatca    4740
gtcaggctcc taggtgcccc cgtaaagaag tcaggtgggg tcaccactat aagccaagta    4800
gtcaggatga acttcttccc tggttttagc ctagaagctg agaagagctt agacaatcag    4860
gaaagacttg agagcatctc catcctcaag catgtcttgt tcatggtctt gaatggccca    4920
tacactgagg agtacaagct ggaaatgatc atagaggcct tctctactct tgtgatacct    4980
cagccatcag aggtcatcag gaaatcaagg accatgactt tatgcctctt atcgaattac    5040
ttgtctagta ggggtgggtc cattctagac cagattgaga gggcacagtc aggcactcta    5100
gggggcttca gcaagcccca gaagacattc attaggccag gaggtggtat tggctacaag    5160
ggaaaaggtg tgtggactgg agtgatggag gacacccatg ttcaaatctt gatagatgga    5220
gatgggacta gtaactggct tgaggagatc aggctcagta gtgatgccag gctttatgat    5280
gtcattgaat ccatccgaag gttatgtgac gaccttggga tcaataacag ggtggcatct    5340
gcatatagag gtcattgcat ggttaggctg agtgggttca agatcaagcc agcatcaagg    5400
actgacggct gtccagtcag gattatggaa aggggcttca ggatcaggga acttcaaaac    5460
ccagatgagg tcaagatgag agtgagggt gacatcctca acctttcagt caccatacaa    5520
gaaggaaggg tcatgaacat tctaagctac aggcctagag acactgatat atcagagtca    5580
gccgcagcat acctctggag caatcgagac ctcttctcct tgggaagaa ggagccatcc    5640 tgcagctgga tctgcttgaa aactcttgac aattgggcct ggtcacatgc ctcagttctc    5700
ctggcaaatg ataggaagac ccaaggcatt gataatagag ccatgggaa catttttcagg    5760 gactgtctcg agggctctct tagaaagcag gggctgatga ggtcaaaact cacagagatg    5820
gtggagaaga atgttgttcc tttaacaact caagagcttg tcgacatctt ggaggaggac    5880
atagactttt cagatgtcat agctgtggag ctctcagagg gatcacttga cattgaatcc    5940
atctttgatg gggcacctat cttgtggtct gctgaggtgg aagagttcgg ggaaggagtg    6000
gtggctgtga gctattccag taagtactat catctaaccc tgatggatca ggctgccatc    6060
acaatgtgtg cgatcatggg taaggaaggc tgtagagggc tccttactga aagagatgc    6120 atggcagcca tacgagagca ggtacggcca ttcctcatat tcctgcaaat tcctgaggac    6180
agcatttctt gggtatctga tcagttctgt gactccaggg gtcttgatga agagagcacc    6240
attatgtggg gttga                                                     6255
```

<210> SEQ ID NO 6
<211> LENGTH: 3222
<212> TYPE: DNA
<213> ORGANISM: Unknown
<220> FEATURE:
<223> OTHER INFORMATION: severe fever thrombocytopenia syndrome virus B-2 M gene

<400> SEQUENCE: 6

```
atgatgaaag tcatctggtt ctcctctctg atctgcttag tcattcaatg cagtggggac        60
acgggcccaa tcatatgcgc agggcccatc cactcaaaca agagtgccga catacccac        120
ctgcttggtt actctgagaa gatttgtcag atagatcggc tgatacatgt ttcgtcatgg       180
ctgagaaacc attcacaatt tcagggctac gtggggcagc gaggtggacg ctctcaggtg       240
agttacttcc cagctgaaaa ctcttactca aggtggagtg ggcttctaag cccctgtgat       300
gctgattggc ttgggatgct tgtcgtgaag aaggccaagg ggtctgatat gatagttcct       360
gggccttcat acaagggaaa agtcttttt gaacggccaa cttttgatgg atatgttggc       420
tggggctgtg gcagtgggaa gtcaaggact gagtcaggag agctctgcag ctcagactca       480
gggaccagtt ccggtcttct gccctcaaat agggttctct ggataggtga tgttgcttgc      540
cagcctatga cacccatccc tgaagagaca tttctggagc tgaagagttt agccagagt       600
gaatttccag atatatgcaa aattgatggc attgtgttca accagtgtga gagtgagagc       660
ctacctcagc cctttgatgt tgcttggatg gatgttggcc actctcataa aatcatcatg       720
agggagcaca agaccaaatg ggtacaagag agctcatcta aggattttgt gtgctacaag       780
gaagggactg ggccgtgttc tgaatcagaa gaaaagactt gcaagaccag tggatcatgt       840
agggggggaca tgcagttttg caaggtggca ggttgtgaac atggggaaga acatctgag       900
gccaaatgca gatgctcact agtgcacaag cccggggaag ttgttgtgtc atatggaggg       960
atgcgtgtca gaccaaaatg ctatggtttc tccagaatga tggcaacact agaggtgaac      1020
ccaccagagc aaaggattgg ccaatgtact ggctgccatc tagaatgcat aaatggggt       1080
gtgaggataa tcactctaac tagtgagctc aagtcagcta ctgtctgtgc ttcccactt       1140
tgtagttctg ccacaagtgg caagaaaagc acggagattc aattccactc agggtcatta      1200
gttgggaaaa cagcaattca cgtcaaaggg gcattggtgg atggaactga attcacattt      1260
gaaggcagtt gcatgttccc agatggttgt gacgcagtgg actgcacatt ctgtcgtgag      1320
tttctaaaaa atcctcagtg ctaccctgca aagaaatggt tgttcatcat tattgtcatc      1380
ctccttggat atgcaggcct catgctactc accaatgtcc ttaaggcaat cggggtttgg      1440
gggtcatggg tcatagctcc agtgaagcta atgtttgcca tcataaagaa actgatgaga      1500
tctgtgagct gcttgatggg gaaattgatg gataggggaa ggcaagtgat ccatgaagaa      1560
atagggggaga atagagaggg caaccaagat gatgttagga tcgagatggc aaggcctaga      1620
agggtaaggc actggatgta ctcacctgtc atcctgacta ttctagcaat tgggcttgct      1680
gagggggtgcg atgagatggt ccatgcagat tctaaacttg tttcgtgcaa gcaagggagc      1740
ggaaatatga aggaatgtgt cacaactggg agggcgctcc ttcctgcggt gaacccaggg      1800
caagaggcat gtctgcactt cacagcacca gggagtccgg actcaaaatg tctcaaaatc      1860
aaagttaaga ggatcaacct gaaatgcaag aagtcatcat catatttcgt tcctgatgct      1920
cggtccaggt gtacatctgt gaggagatgc cgctgggcag agactgtca gtctgggtgc      1980
ccctctcatt tcacgtccaa ctcctttttct gacgattggg caggtaaaat ggacagggct      2040
ggtctaggat tcagtgggtg ctctgatgga tgtggaggag cagcctgcgg ctgctttaat      2100
gcggccctt catgcatctt ctggaggaaa tgggtagaga atccacatgg gatcatctgg      2160
aaagtatctc catgtgctgc atgggtccca tcagcagtca tagagcttac aatgcctcg      2220
ggggaagtga ggacattcca ccccatgagc ggcatcccta ctcaagtctt caagggtgtg      2280
```

```
agtgtgactt atttgggctc agatatggag gtatctggct tgactgatct gtgtgaaata    2340
gaagagctca agtccaagaa gctggcatta gctccctgca atcaggctgg catgggggtt    2400
gtaggcaagg ttggagagat acagtgcagt agtgaggaaa gtgcccgtac cataaaaaaa    2460
gatgggtgta tatggaatgc tgacctcgtg ggcatcgagc tacgagtgga tgacgctgtg    2520
tgctactcta agatcactag tgtggaggca gttgcaaact actctgccat acccaccact    2580
attgggggac tgaggtttga gagaagccat gacagccagg gcaaaatatc tggtagcccc    2640
ttggacatca cagccataag agggtctttt tcagttaact atagaggcct tcgactgagc    2700
ctctcagaaa ttactgctac ttgcacaggg gaggtgacaa atgtgagtgg gtgttactct    2760
tgcatgacag gcgccaaagt ctccatcaaa ctgcatagca gcaaaaatag cactgcacat    2820
gtaaggtgca aaggggatga gactgcgttc agtgtcctgg agggagttca tagctatact    2880
gtcagcctca gttttgacca tgcagtggtc gatgagcagt gccagctgaa ctgtgggggg    2940
catgagagcc aagtgactct aaaaggcaac ctcatcttcc tggatgtccc aaaattcgta    3000
gatggcagct acatgcagac atatcatagc tctgtaccca caggagcaaa tatcccaagc    3060
ccaacagact ggctgaatgc cctgtttggc aatgggctga gtaggtggat tctgggggtg    3120
ataggggttc tactggggggg attagctctc ttttttcctaa tcatgtcttt gttcaaactg    3180
ggaacaaaac aggtatttcg atcaaggacg aagctggctt ag                        3222

<210> SEQ ID NO 7
<211> LENGTH: 738
<212> TYPE: DNA
<213> ORGANISM: Unknown
<220> FEATURE:
<223> OTHER INFORMATION: severe fever thrombocytopenia syndrome virus
      B-2 NP gene

<400> SEQUENCE: 7
atgtcagagt ggtccaggat tgcagtggag tttggtgagc agcagctcaa tttgactgag      60
cttgaagatt ttgcgagaga gctggcctat gaaggccttg atcctgcatt gatcatcaag     120
aagctgaagg agacaggtgg agatgattgg gtgagggaca caaagttcat cattgtctttt   180 gccctgactc gaggcaacaa gatcgtcaag gcatcaggga aaatgtcaaa ctctgggtct     240
aagaggttga tggcactcca agagaaatat gggctggttg agagggcaga aaccaggctc     300
tcaatcactc ctgtgagggt tgcacagagc cttcccactt ggacatgtgc tgcagcagca     360
gccctaaagg agtatctccc agtggggcca gctgtcatga acctgaaggt cgaaaaattat     420 cccccctgaga tgatgtgcat ggcctttggg tccctgattc caactgcagg ggtatctgaa     480
gccacaacga agaccctgat ggaggcctac tctctgtggc aagatgcctt caccaagact     540
atcaatgtaa agatgcgcgg agccagcaag acagaggttt acaactcttt cagggatcct     600
ctccatgctg ctgtgaactc tgtcttcttt cccaatgatg tccgggtgaa gtggctgaag     660
gccaagggaa tccttggccc agatggggtc cccagcagag ctgctgaggt tgctgccgct     720
gcttacagaa acctgtaa                                                   738

<210> SEQ ID NO 8
<211> LENGTH: 882
<212> TYPE: DNA
<213> ORGANISM: Unknown
<220> FEATURE:
<223> OTHER INFORMATION: severe fever thrombocytopenia syndrome virus
      B-2 NS gene
```

<400> SEQUENCE: 8

```
atgtcgctga gcaaatgctc caacgttgac ctcaaatctg ttgcaatgaa tgccaacact      60
gtcaggcttg agccatctct aggagagtac cccactctta ggagagacct cgttgaatgc     120
tcttgtagtg tgttgactct atcaatggtc aagaggatgg gcaagatgac caacacagta     180
tggctatttg caacccaaa gaatcctctt caccagcttg agcctggact cgagcagctg      240
ttagacatgt actacaagga catgaggtgc tactcccaga gagagctgag tgctcttagg     300
tggcctagtg ggaagccatc tgtatggttc ctacaggcag ctcacatgtt cttctccatc     360
aagaacagct gggcaatgga aaccggtaga gagaactggc ggggcctctt ccacaggata     420
acaaaaggcc aaaagtatct ttttgaaggg gacatgatat tggattctct tgaggccata     480
gagaagcgaa ggcttagact agggttacct gagatcctaa taactgggct atccccaatt     540
ctggatgtgg ccctcctcca gatagagtca cttgcaaggc taagaggaat gagcttgaac     600
caccacttat tcacttcttc ctcattgcgt aagcctctat tagactgttg ggacttcttt     660
attcccatcc gcaaaaagaa gacagatggc tcatacagtg tcctggatga ggatgatgag     720
cctgggatcc ttcaaggtta tccatatctg atggcacact atttgaatag gtgcccattc     780
cacaacctca tcaggtttga tgaagagctg agaactgcag ccctaaacac catctgggga     840
agagattggc cagccattgg tgacctcccg aaggaggtct aa                        882
```

<210> SEQ ID NO 9
<211> LENGTH: 6255
<212> TYPE: DNA
<213> ORGANISM: Unknown
<220> FEATURE:
<223> OTHER INFORMATION: severe fever thrombocytopenia syndrome virus B-3 L gene

<400> SEQUENCE: 9

```
atgaacttgg aagtgctttg tggtaggata aacgtggaga tgggctgtc tcttggagaa       60
ccaggcctgt acgaccaaat ctacgacagg ccagggctgc cagacctaga tgtgactgtc     120
gatgccatag gtgtgacagt ggacataggg gctgtgccag actcagcatc acaactgggt     180
tcatcaatca atgctgggtt gatcacaatc cagctctctg aagcatataa gatcaatcat     240
gatttcacgt tttctggcct gtcaaagaca acagaccgac gcctctcaga ggtattcccc     300
attacacatg atggttctga tgggatgacc cctgatgtga tccacaccag attggatgga     360
accattgtgg tggttgaatt ttcaactact aggagccata acattggggg tctggaggca     420
gcatacagga caaagataga aaatatagg gaccctatct caaggcgtgt tgatatcatg     480
gagaacccga gggtcttctt tggcgtcatt gtggtctcgt caggggagt tctgtccaac     540
atgccctga ctcaggatga ggcagaggag ctcatgtaca ggttctgcat agccaatgag     600
atctacacta aggctaggtc tatggatgca gacattgagc tgcagaagag cgaagaagag     660
cttgaggcta ttagcagggc actatcattc ttcagtttgt ttgagccaaa cattgaaaga     720
gtggaaggaa cattccctaa ttcggaaatc gagatgctgg aacagtttct ctcaactcca     780
gctgatgttg acttcatcac caagacccta aagcaaaag aggtggaggc ctatgctgat     840
cttttgtgaca gccactatct aaagcctgaa aaaaccattc aggagcggct agagatcaat     900
agatgtgagg ctattgacaa gactcaggac ctcctagcta gcctgcatgc aaggagcaac     960
aagcaaacat cattgaatcg agggacagtc aagctcccgc cctggctacc aaagccatca    1020
agtgagtcaa tagacatcaa gactgactca ggctttggtt ccttaatgga tcatggcaca    1080
```

```
tatggagagc tgtgggcaaa gtgcctccta gatgtctcgc tgggcaatgt ggaggggta    1140 gtcagtgacc ctgcaaaaga acttgacatt gctatctctg atgatccaga aaaagatacc   1200
cccaaagagg caaagataac ctataggcgg ttcaagcctg ccttgagctc aagtgcccgt   1260
caagaatttt ctctccaagg agtggagggg aagaagtgga agagaatggc agcaaaccag   1320
aagaaagaga aggagtccca tgagacattg agccctttct tggatgttga agacattggg   1380
gatttcctaa cattcaacaa tcttctcgca gattcgaggt atggagatga gtccgtccag   1440
agagctgtgt caatcttgtt ggaaaaggca tctgccatgc aagacacaga gctcactcat   1500
gccctcaacg actcattcaa gaggaaccta agcagcaatg tggttcagtg gtcccttggg   1560
gtctcctgtc tagcacaaga gctagctagt gctctgaagc agcactgcag ggctggtgag   1620
ttcatcatca agaagctgaa gttctggcct atctatgtca ttatcaagcc gaccaaatcg   1680
tcatcccata tcttctacag cttagggatc cgcaaggctg atgtgacaag gaggctcact   1740
ggcagagtct tctctgacac cattgatgct ggggaatggg agctaacaga gttcaagagc   1800
ctgaagacat gcaagctcac caaccttgtc aacttgccat gcaccatgct gaactcaata   1860
gctttctgga gagagaagct gggcgtggcc ccatggctgg ttcggaagcc ttgttcagag   1920
ctcagagagc aggtgggcct gaccttcttg atcagtttgg aggacaagtc taagactgag   1980
gagatcatca ccttgacaag gtacactcaa atggagggct cgtctctcc tcctatgctg   2040 cctaagcccc aaaagatgct agggaaactg gatgggcctt tgagaactaa gctacaggta   2100
tacctcctca ggaagcatct ggattgcatg gtgcgaattg cttcccagcc attcagcctg   2160
atccctagag aggggagggt agaatgggga gggacattcc atgccatctc aggccggtcc   2220
acaaaccttg agaatatggt gaacagctgg tacattgggt actacaagaa caaagaggag   2280
tcaacagagc taaatgctct tggagaaatg tataagaaga ttgtggagat ggaagaggac   2340
aagcccagca gccctaagtt tctagggtgg ggggacactg attcccctaa gaagcatgaa   2400
ttctcacgga gcttcctcag agctgcttgc tcatctctgg agagaaaat tgctcagcga   2460 catggaagac aatggaagca gaaccttgag gagcgtgtcc tgagagagat tggaaccaag   2520
aacatcctag accttgcatc catgaaggct acaagcaact tttccaaaga ctgggagctc   2580
tactcagaag tccagaccaa agagtaccat aggtccaaat tgctggagaa gatggccaca   2640
ttgattgaga aggggttat gtggtacatt gatgctgtgg gccaggcttg gaaggcagtt   2700
ctagatgacg ggtgcatgcg aatctgtctc ttcaaaaaga atcagcatgg tggcctcaga   2760
gagatctacg ttatggatgc aaatgcccgg ctcgtgcagt ttgggggtga gaccatggct   2820
aggtgtgtct gtgagctgag cccacatgag actgttgcca atcctaggct taagaattcc   2880
atcatagaga accatgggct gaagtcagcc cgtagccttg gcctggctc tataaacata   2940 aactcatcca atgatgccaa gaagtggaat caggggcact acacaacaaa gctagctcta   3000
gttctttgtt ggttcatgcc agccaaattc cacagattca tttgggctgc catttccatg   3060
tttcggagaa aaaagatgat ggtggaccta aggttttag ctcacctcag ttctaaatct   3120
gagtccaggt catctgatcc atttagggaa gcaatgacag acgcattcca tggaaatagg   3180
gaagtctcat ggatggacaa ggggcgaact tacataaaga cagagacagg gatgatgcag   3240
ggcatactgc actttacatc cagcctcctc cactcttgtg ttcagagtttt ttacaagtct   3300 tatttcgtct cgaagctcaa ggagggctac atgggggaaa gcatcagtgg ggtggtggat   3360
gtcatagaag ttctgacga ctcagcgatc atgatcagca tacgccctaa gtcagatatg   3420
gatgaagtcc gatcaaggtt ttttgttgct aacctgctcc actctgtcaa attcttgaac   3480
```

```
cctttgtttg ggatttactc atcagagaag tcaacagtga acacagtgta ttgtgtcgag    3540
tataactctg aattccattt ccacaggcac ttggttagac ccacactgag atggatagca    3600
gcgtctcacc aaatctcaga gactgaagcc cttgcaagca ggcaagagga ttactccaac    3660
cttctaaccc agtgcttgga aggagggcc tcattctctc ttacctacct catacagtgc     3720
gctcagctcc tacaccacta catgcttcta ggactatgct tgcatccctt gtttggaacc    3780
ttcatgggga tgctgatatc agacccagat cctgccctag gattcttcct catggacaac    3840
cctgcattcg caggaggagc aggatttaga ttcaatctgt ggagagcctg caagaccaca    3900
gaccttgggc ggaagtatgc atattacttc aatgagatac agggtaaaac aaagggagat    3960
gaggactaca gagctctgga cgccacatcg ggaggaactc tcagccactc tgttatggtg    4020
tactgggggg acaggaagaa gtatcaggcc ttattgaaca ggatgggcct tcctgaagac    4080
tgggtggagc agatagatga gaatcctgga gtccttttaca ggagagctgc caacaagaag    4140
gaactactct aaaaactggc agagaaggtt cattcacctg gtgtgactag cagcctgagt    4200
aaagggcatg tagtgcctcg ggtggtggca gcaggagtat accttctctc acgccactgc    4260
tttcgcttta gctcaagcat ccatggaagg ggctcagcac agaaggctag tctcataaaa    4320
ctgctgatga tgtcttctat ttctgccatg aaacacgggg gctcattaaa ccccaatcag    4380
gagcgaatgc tcttccctca ggctcaagag tatgatagag tatgcacatt gcttgaggaa    4440
gttgaacacc taacagggaa atttgttgtt agggagagaa acattgtcag gagccgcata    4500
gacttgttcc aagagccagt tgacttgcgg tgtaaggcag aagatctggt gtcagaggtg    4560
tggtttggcc tgaaaaggac taagcttgga ccccgtctcc tcaaggaaga gtgggacaaa    4620
cttagggcct catttgcatg gctgagcaca gacccatctg aaacattgag ggatggtcct    4680
tttcttagcc atgtgcagtt taggaacttc atagcccacg ttgatgccaa atcaagatca    4740
gtcaggctcc taggtgcccc cgtgaagaag tcaggtgggg taaccaccat aagccaagta    4800
gtcagaatga acttcttccc tggttttagc ctagaagctg agaagagctt agacaatcag    4860
gagagacttg agagcatctc catcctcaag catgtcttgt tcatggtctt gaatggccca    4920
tacactgagg agtacaagct ggacatgatc atagaggcct tctctactct tgtgatacct    4980
cagccatcag aggtcatcag gaaatcaagg accatgactt tatgcctctt atcgaattac    5040
ttgtctagta ggggtgggtc cattctagac cagattgaga gggcacagtc aggcactcta    5100
gggggattca gcaagcccca gaagacattc atcaggccag aggtggtat tggctacaag    5160 ggaaaaggtg tgtggactgg agtgatggag gacacccatg ttcaaattct gatagatgga    5220
gatgggacta gcaactggct tgaggagatc aggctcagta gtgatgccag gctttatgat    5280
gtcattgaat ccatccggag gttatgtgat gaccttggga tcaacaacag ggtggcatcg    5340
gcatataggg gtcattgcat ggttagactg agtggattca agatcaagcc agcatcaagg    5400
actgacggct gtccagttag gattatggaa aggggcttca ggatcagaga gcttcaaaac    5460
ccagatgagg tcaagatgag agtgaggggt gacattctca acctctctgt taccatacaa    5520
gaaggaagag tcatgaacat tctgagctac aggccgagag acactgatat atcagagtca    5580
gcagcagcat acctatggag caatcgagac ctcttctcct tgggaagaa ggagccatcc    5640 tgcagctgga tctgcttgaa aactcttgac aattgggcct ggtcacatgc ctcagttctc    5700
ctggcaaatg ataggaagac ccaaggcatt gataatagag ctatgggga cattttcagg    5760 gactgtctcg agggttccct cagaaagcaa gggctgatga ggtcaaagct cactgagatg    5820
```

```
gtggagaaga atgtggttcc tttaacaact caagagcttg tcgatatcct ggaggaggat      5880
atagactttt cagatgtcat agctgtggag ctctcagagg gatcacttga cattgagtcc      5940
atctttgatg gagcacctat cttgtggtct gctgaggtgg aagagtttgg agaaggagtg      6000
gtagctgtga gctattccag taagtactat catctaaccc tgatggacca agctgccatc      6060
acaatgtgtg cgatcatggg taaggagggc tgtagagggc tcctcactga aagagatgc      6120 atggcagcca tacgagagca ggtaaggcca ttcctcatat tcctgcaaat ccctgaggac      6180
agcatttctt gggtgtctga tcagttctgc gactccaggg gtcttgatga agagagcacc      6240
attatgtggg gttaa                                                       6255

<210> SEQ ID NO 10
<211> LENGTH: 3222
<212> TYPE: DNA
<213> ORGANISM: Unknown
<220> FEATURE:
<223> OTHER INFORMATION: severe fever thrombocytopenia syndrome virus
      B-3 M gene

<400> SEQUENCE: 10
atgatgaaag tcatctggtt ctcctctctg atctgcttag tcattcaatg cagtggggat        60
acgggcccaa tcatatgcgc tgggcccatc cactcaaaca agagcgccaa catacccac       120 ctgcttggtt actctgagaa aatttgtcag atagatcggc ttatacatgt ttcgtcatgg      180
ctgagaaacc attcacaatt tcagggctac gtggggcagc gaggtggacg ctctcaggtg      240
agttactacc cagctgaaaa ctcttactca aggtggagtg gacttctaag cccctgtgat      300
gctgattggc ttgggatgct tgtcgtgaag aaggccaagg ggtctgatat gatagttcct      360
gggccttcat acaaagggaa agtcttcttt gaacggccaa cttttgatgg atatgtgggc      420
tggggctgtg gtagtgggaa gtcaaggaca gagtcaggtg agctctgcag ctcagactca      480
gggaccagtt ctggtctact gccctcaaat agggttctct ggataggtga tgttgcttgc      540
cagcctatga cacccatccc tgaggagaca tttctggagc tgaagagttt tagccagagt      600
gaattcccag acatatgcaa agttgatggc attgtgttca accagtgtga gagtgagagt      660
ctacctcagc cctttgatgt tgcatggatg gatgtaggcc actctcataa aatcatcatg      720
agggagcaca gaccaaaatg ggtacaagag agctcatcta aggattttgt gtgctacaag      780
gaagggactg ggccgtgttc tgaatcagaa gaaaagactt gcaagaccag tggatcatgc      840
aggggggaca tgcagttttg caaggtagca ggttgtgaac atggggaaga ggcatctgaa      900
gccaaatgta gatgctcact agtgcacaag cccgggggaag ttgttgtgtc atatggaggg      960
atgcgtgtca gaccaaagtg ttatggtttc tccagaatga tggcaacact agaggtgaac      1020
ccaccagagc aaagaattgg ccaatgcact ggctgccatc tagaatgcat aaatggggt      1080 gtgaggctaa ttactctaac tagtgagctc aagtcagcta ctgtctgtgc ttcccacttt      1140
tgtagttctg ctacaagtgg caagaaaagc acggagattc aattccactc agggtcatta      1200
gttgggaaag cagcaattca cgtcaaaggg actttggtgg atggaactga attcacattt      1260
gagggcagtt gcatgttccc agatggttgt gacgcagtgg actgcacatt ctgtcgcgag      1320
ttcctaaaaa atcctcagtg ctaccctgca aagaaatggt tgttcataat tattgccatc      1380
ctccttggat atgcaggcct catgctgctc accaatgttc ttaaggcaat cggggtttgg      1440
ggatcatggg tctagctcc agtgaagctg atgtttgcca tcataaagaa actgatgaga      1500
tctgtgagct gcttgatggg gaaattaatg gataggggaa ggcaagtgat tcatgaagaa      1560
```

-continued

| | |
|---|---|
| ataggggaga atagagaggg caaccaagaa gatgttagaa ttgagattgc aagacccaga | 1620 |
| agggtgaggc attggatgta ctcacctgtc atcctggcta ttctagcaat tgggcttgct | 1680 |
| gagggctgcg atgagatggt ccatgcagat tcaaaacttg tttcgtgcag gcaagggagc | 1740 |
| ggaaatatga aggaatgtgt cacaactggg agggcgcttc ttcctgcggt gaacccagga | 1800 |
| caagaggcat gtctgcactt cacggcacct ggaagtccgg actcaaaatg tctcaagatc | 1860 |
| aaggttaaga ggatcaacct aaaatgtaag aagtcatcat catattttgt tcctgatgct | 1920 |
| cggtccagat gtacgtctgt gaggagatgt cgctgggcag gagactgtca gtctgggtgc | 1980 |
| ccctctcatt tcacgtccaa ctccttctct gatgattggg caggtaaaat ggacagggct | 2040 |
| ggtctaggat tcagtgggtg ctctgatgga tgtggaggag cagcctgcgg ctgctttaat | 2100 |
| gcggccccct catgcatctt ttggaggaaa tgggtagaga atccacatgg gatcatctgg | 2160 |
| aaagtatctc catgtgctgc atgggtccct tcaacagtca tagagctaac aatgccctcg | 2220 |
| ggggaagtga ggacattcca ccccatgagc ggcatcccca cacaagtctt caagggtgtg | 2280 |
| agtgtgactt acttaggctc agatatggag gtgtctggcc tgactgacct gtgtgagata | 2340 |
| gaagagctca gtccaagaa gctggcatta gctccctgca atcaggctgg catgggagtt | 2400 |
| gtgggcaagg ttggagagat acagtgcagt agcgaggaaa gcgcccgttc cataaagaaa | 2460 |
| gatgggtgta tatggaatgc tgaccttgtg ggcatagagc tacgagtgga tgacgcagtg | 2520 |
| tgctattcta agatcactag tgtggaggca gttgcaaact actctgccat acccaccact | 2580 |
| attgggggt tgaggtttga gagaagccat gacagccagg gtaaaatatc tggtagcccc | 2640 |
| ctagacatta cagccataag agggtctttt tccgttaatt atagaggcct tcgactgagc | 2700 |
| ctctcagaaa tcactgctac ttgcacagga gaggtgacga atgtgagtgg gtgttactct | 2760 |
| tgcatgacag gcgccaaagt ctccatcaaa ctgcatagca gcaaaaatag cactgcccat | 2820 |
| gtaagatgca aggggatga accgcattc agtgtcctgg agggagttca tagctatact | 2880 |
| gtcagtctta gctttgacca tgcagtggtc gatgagcagt gccagctgaa ctgtgggggg | 2940 |
| catgagagtc aagtgactct aaaaggcaac ctcatcttcc tggatgtccc aaaatttgta | 3000 |
| gatggcagct atatgcagac atatcatagt tctgtgccca caggggctaa tatcccaagc | 3060 |
| cctacagact ggctgaatgc cttgtttggc aatgggctga gtaggtggat tcttggggta | 3120 |
| atagggggttc tactgggggg attggctctc ttcttcttaa ttatgtccct tgttcaaactg | 3180 |
| ggaacaaaac agatattccg atcaaggacg aagctggctt ag | 3222 |

<210> SEQ ID NO 11
<211> LENGTH: 738
<212> TYPE: DNA
<213> ORGANISM: Unknown
<220> FEATURE:
<223> OTHER INFORMATION: severe fever thrombocytopenia syndrome virus
    B-3 NP gene

<400> SEQUENCE: 11

| | |
|---|---|
| atgtcagagt ggtccaggat tgcagtggag tttggtgagc agcagctcaa tttgactgag | 60 |
| cttgaggatt tcgcgagaga gctagcctat gaaggccttg atcctgcctt gataatcaag | 120 |
| aagctgaagg agacaggtgg agatgattgg gtgagagata caaagttcat cattgtcttt | 180 |
| gccctgaccc gaggcaacaa gatcgtcaag gcatcaggga aaatgtcaaa ctcagggtct | 240 |
| aagaggttga tggcacttca agagaaatat ggactggttg agagggcaga aaccaggctc | 300 |
| tcaatcactc ctgtgagggt agcacagagc cttcccactt ggacgtgcgc tgcagcagca | 360 |

```
gccttaaagg agtatctccc agtgggccca gctgtcatga acctgaaggt cgaaaattac    420 ccccccagaga tgatgtgcat ggcctttggg tctctgattc aactgcagg ggtatcagaa    480 gccacaacga agaccctgat ggaggcctac tctctgtggc aagatgcctt caccaagact    540
attaatgtga agatgcgtgg agccagcaag acagaggttt acaactcctt cagagatccc    600
ctccatgctg ctgtgaactc tgtcttcttt cccaatgatg ttcgggtgaa gtggctgaag    660
gccaagggaa tcctaggccc agatggggtc cccagcagag ctgctgaggt tgctgctgct    720
gcttacagaa acctgtaa                                                  738
```

<210> SEQ ID NO 12
<211> LENGTH: 882
<212> TYPE: DNA
<213> ORGANISM: Unknown
<220> FEATURE:
<223> OTHER INFORMATION: severe fever thrombocytopenia syndrome virus B-3 NS gene
<400> SEQUENCE: 12

```
atgtcgctga gcaaatgctc caacgttgac ctcaaatctg tagcaatgaa tgccaacact    60
gttaggcttg aaccatctct aggagagtac cccactctta ggaaagacct cgttgaatgc    120
tcttgtagtg tgttgactct atcaatggtc aagaggatgg gcaagatgac caacacagta    180
tggttatttg gcaacccaaa aaatcctctt caccagcttg agcctggact tgagcagctg    240
ttggatatgt actacaagga catgaggtgc tactcccaga gagagctgag tgccctcagg    300
tggcctagtg ggaagcctct tgtatggttc ctacaggcag ctcacatgtt cttttccatc    360
aagaacagct gggcaatgga aaccggtaga gagaactggc ggggcctctt ccacaggata    420
acaaaaggca aaaagtatct ttttgaaggg gacatgatat tggattctct tgaagccata    480
gagaagcgaa ggctcagact tgggttacct gagatcctaa taactggact atccccaatt    540
ctggatgtgg ccctcctcca gatagagtca cttgcaaggc taagaggcat gagcttgaac    600
caccacttat tcacttcttc ctcactgcgt aagcctctgt tagattgttg ggacttcttt    660
attcctatcc gcaaaaagaa gacagatggc tcatacagtg ttttggatga ggatgatgag    720
cctggggtcc ttcaaggtta cccatatctg atggcacact atctgaacag gtgcccattc    780
cacaacctca tcagatttga tgaagaactg agaactgcag ccctgaacac catctgggga    840
agagattggc cggccattgg tgacctcccg aaggaggtct aa                        882
```

<210> SEQ ID NO 13
<211> LENGTH: 2084
<212> TYPE: PRT
<213> ORGANISM: Unknown
<220> FEATURE:
<223> OTHER INFORMATION: severe fever thrombocytopenia syndrome virus B-1 L
<400> SEQUENCE: 13

```
Met Asp Leu Glu Val Leu Cys Gly Arg Ile Asn Val Glu Asn Gly Leu
1               5                   10                  15

Ser Leu Gly Glu Pro Gly Leu Tyr Asp Gln Ile Tyr Asp Arg Pro Gly
            20                  25                  30

Leu Pro Asp Leu Asp Val Thr Val Asp Ala Thr Gly Val Thr Val Asp
        35                  40                  45

Ile Gly Ala Val Pro Asp Ser Ala Ser Gln Leu Gly Ser Ser Ile Asn
    50                  55                  60

Ala Gly Leu Ile Thr Ile Gln Leu Ser Glu Ala Tyr Lys Ile Asn His
```

-continued

```
            65                  70                  75                  80
Asp Phe Thr Phe Ser Gly Leu Ser Lys Thr Asp Arg Arg Leu Ser
                    85                  90                  95
Glu Val Phe Pro Ile Thr His Asp Gly Ser Asp Gly Met Thr Pro Asp
                100                 105                 110
Val Ile His Thr Arg Leu Asp Gly Thr Ile Val Val Glu Phe Ser
                115                 120                 125
Thr Thr Arg Ser His Asn Ile Gly Gly Leu Glu Ala Ala Tyr Arg Thr
    130                 135                 140
Lys Ile Glu Lys Tyr Arg Asp Pro Ile Ser Arg Arg Val Asp Ile Met
145                 150                 155                 160
Glu Asn Pro Arg Val Phe Phe Gly Val Ile Val Ser Ser Gly Gly
                    165                 170                 175
Val Leu Ser Asn Met Pro Leu Thr Gln Asp Glu Ala Glu Glu Leu Met
                180                 185                 190
Tyr Arg Phe Cys Ile Ala Asn Glu Ile Tyr Thr Lys Ala Arg Ser Met
                195                 200                 205
Asp Ala Asp Ile Glu Leu Gln Lys Ser Glu Glu Leu Glu Ala Ile
    210                 215                 220
Ser Arg Ala Leu Ser Phe Phe Ser Leu Phe Glu Pro Asn Ile Glu Arg
225                 230                 235                 240
Val Glu Gly Thr Phe Pro Asn Ser Glu Ile Glu Met Leu Glu Gln Phe
                    245                 250                 255
Leu Ser Thr Pro Ala Asp Val Asp Phe Ile Thr Lys Thr Leu Lys Ala
                260                 265                 270
Lys Glu Val Glu Ala Tyr Ala Asp Leu Cys Asp Ser His Tyr Leu Lys
                275                 280                 285
Pro Glu Lys Thr Ile Gln Glu Arg Leu Glu Ile Asn Arg Cys Glu Ala
                290                 295                 300
Ile Asp Lys Thr Gln Asp Leu Leu Ala Gly Leu His Ala Arg Ser Asn
305                 310                 315                 320
Lys Gln Thr Ser Leu Asn Arg Gly Thr Val Lys Leu Pro Pro Trp Leu
                    325                 330                 335
Pro Lys Pro Ser Ser Glu Ser Ile Asp Ile Lys Thr Asp Ser Gly Phe
                340                 345                 350
Gly Ser Leu Met Asp His Gly Ala Tyr Gly Glu Leu Trp Ala Lys Cys
                355                 360                 365
Leu Leu Asp Val Ser Leu Gly Asn Val Glu Gly Val Val Ser Asp Pro
    370                 375                 380
Ala Lys Glu Leu Asp Ile Ala Ile Ser Asp Asp Pro Glu Lys Asp Thr
385                 390                 395                 400
Pro Lys Glu Ala Lys Ile Thr Tyr Arg Arg Phe Lys Pro Ala Leu Ser
                    405                 410                 415
Ser Ser Ala Arg Gln Glu Phe Ser Leu Gln Gly Val Glu Gly Lys Lys
                420                 425                 430
Trp Lys Arg Met Ala Ala Asn Gln Lys Lys Glu Lys Glu Ser His Glu
                435                 440                 445
Thr Leu Ser Pro Phe Leu Asp Val Glu Asp Ile Gly Asp Phe Leu Thr
    450                 455                 460
Phe Asn Asn Leu Leu Ala Asp Ser Arg Tyr Gly Asp Glu Ser Ile Gln
465                 470                 475                 480
Arg Ala Val Ser Ile Leu Leu Glu Lys Ala Ser Ala Met Gln Asp Thr
                    485                 490                 495
```

```
Glu Leu Thr His Ala Leu Asn Asp Ser Phe Lys Arg Asn Leu Ser Ser
            500                 505                 510

Asn Val Val Gln Trp Ser Leu Trp Val Ser Cys Leu Ala Gln Glu Leu
        515                 520                 525

Ala Ser Ala Leu Lys Gln His Cys Arg Ala Gly Glu Phe Ile Ile Lys
530                 535                 540

Lys Leu Lys Phe Trp Pro Ile Tyr Val Ile Lys Pro Thr Lys Ser
545                 550                 555                 560

Ser Ser His Ile Phe Tyr Ser Leu Gly Ile Arg Lys Ala Asp Val Thr
                565                 570                 575

Arg Arg Leu Thr Gly Arg Val Phe Ser Asp Thr Ile Asp Ala Gly Glu
            580                 585                 590

Trp Glu Leu Thr Glu Phe Lys Ser Leu Lys Thr Cys Lys Leu Thr Asn
        595                 600                 605

Leu Val Asn Leu Pro Cys Thr Met Leu Asn Ser Ile Ala Phe Trp Arg
    610                 615                 620

Glu Lys Leu Gly Val Ala Pro Trp Leu Val Arg Lys Pro Cys Ser Glu
625                 630                 635                 640

Leu Arg Glu Gln Val Gly Leu Thr Phe Leu Ile Ser Leu Glu Asp Lys
                645                 650                 655

Ser Lys Thr Glu Glu Ile Ile Thr Leu Thr Arg Tyr Thr Gln Met Glu
            660                 665                 670

Gly Phe Val Ser Pro Pro Met Leu Pro Lys Pro Gln Lys Met Leu Gly
        675                 680                 685

Lys Leu Asp Gly Pro Leu Arg Thr Lys Leu Gln Val Tyr Leu Leu Arg
    690                 695                 700

Lys His Leu Asp Cys Met Val Arg Ile Ala Ser Gln Pro Phe Ser Leu
705                 710                 715                 720

Ile Pro Arg Glu Gly Arg Val Glu Trp Gly Gly Thr Phe His Ala Ile
                725                 730                 735

Ser Gly Arg Ser Thr Asn Leu Glu Asn Met Val Asn Ser Trp Tyr Ile
            740                 745                 750

Gly Tyr Tyr Lys Asn Lys Glu Glu Ser Thr Glu Leu Asn Ala Leu Gly
        755                 760                 765

Glu Met Tyr Lys Lys Ile Val Glu Met Glu Asp Lys Pro Ser Ser
    770                 775                 780

Pro Glu Phe Leu Gly Trp Gly Asp Thr Asp Ser Pro Lys Lys His Glu
785                 790                 795                 800

Phe Ser Arg Ser Phe Leu Arg Ala Ala Cys Ser Ser Leu Glu Arg Glu
                805                 810                 815

Ile Ala Gln Arg His Gly Arg Gln Trp Lys Gln Asn Leu Glu Glu Arg
            820                 825                 830

Val Leu Arg Glu Ile Gly Thr Lys Asn Ile Leu Asp Leu Ala Ser Met
        835                 840                 845

Lys Ala Thr Ser Asn Phe Ser Lys Asp Trp Glu Leu Tyr Ser Glu Val
    850                 855                 860

Gln Thr Lys Glu Tyr His Arg Ser Lys Leu Leu Glu Lys Met Ala Thr
865                 870                 875                 880

Leu Ile Glu Lys Gly Val Met Trp Tyr Ile Asp Ala Val Gly Gln Ala
                885                 890                 895

Trp Lys Ala Val Leu Asp Asp Gly Cys Met Arg Ile Cys Leu Phe Lys
            900                 905                 910
```

```
Lys Asn Gln His Gly Gly Leu Arg Glu Ile Tyr Val Met Asp Ala Asn
            915                 920                 925

Ala Arg Leu Val Gln Phe Gly Val Glu Thr Met Ala Arg Cys Val Cys
930                 935                 940

Glu Leu Ser Pro His Glu Thr Val Ala Asn Pro Arg Leu Lys Asn Ser
945                 950                 955                 960

Ile Ile Glu Asn His Gly Leu Lys Ser Ala Arg Ser Leu Gly Pro Gly
            965                 970                 975

Ser Ile Asn Ile Asn Ser Ser Asn Asp Ala Arg Lys Trp Asn Gln Gly
            980                 985                 990

His Tyr Thr Thr Lys Leu Ala Leu Val Leu Cys Trp Phe Met Pro Ala
            995                 1000                1005

Lys Phe His Arg Phe Ile Trp Ala Ala Ile Ser Met Phe Arg Arg
    1010                1015                1020

Lys Lys Met Met Val Asp Leu Arg Phe Leu Ala His Leu Ser Ser
    1025                1030                1035

Lys Ser Glu Ser Arg Ser Ser Asp Pro Phe Arg Glu Ala Met Thr
    1040                1045                1050

Asp Ala Phe His Gly Asn Arg Glu Val Ser Trp Met Asp Lys Gly
    1055                1060                1065

Arg Thr Tyr Ile Lys Thr Glu Thr Gly Met Met Gln Gly Ile Leu
    1070                1075                1080

His Phe Thr Ser Ser Leu Leu His Ser Cys Val Gln Ser Phe Tyr
    1085                1090                1095

Lys Ser Tyr Phe Val Ser Lys Leu Lys Glu Gly Tyr Met Gly Glu
    1100                1105                1110

Ser Ile Asn Gly Val Val Asp Val Ile Glu Gly Ser Asp Asp Ser
    1115                1120                1125

Ala Ile Met Ile Ser Ile Arg Pro Lys Ser Asp Met Asp Glu Val
    1130                1135                1140

Arg Ser Arg Phe Phe Val Ala Asn Leu Leu His Ser Val Lys Phe
    1145                1150                1155

Leu Asn Pro Leu Phe Gly Ile Tyr Ser Ser Glu Lys Ser Thr Val
    1160                1165                1170

Asn Thr Val Tyr Cys Val Glu Tyr Asn Ser Glu Phe His Phe His
    1175                1180                1185

Arg His Leu Val Arg Pro Thr Leu Arg Trp Ile Ala Ala Ser His
    1190                1195                1200

Gln Ile Ser Glu Thr Glu Ala Leu Ala Ser Arg Gln Glu Asp Tyr
    1205                1210                1215

Ser Asn Leu Leu Thr Gln Cys Leu Glu Gly Gly Ala Ser Phe Ser
    1220                1225                1230

Leu Thr Tyr Leu Ile Gln Cys Ala Gln Leu Leu His His Tyr Met
    1235                1240                1245

Leu Leu Gly Leu Cys Leu His Pro Leu Phe Gly Thr Phe Met Gly
    1250                1255                1260

Met Leu Ile Ser Asp Pro Asp Pro Ala Leu Gly Phe Phe Leu Met
    1265                1270                1275

Asp Asn Pro Ala Phe Ala Gly Gly Ala Gly Phe Arg Phe Asn Leu
    1280                1285                1290

Trp Arg Ala Cys Lys Thr Thr Asp Leu Gly Arg Lys Tyr Ala Tyr
    1295                1300                1305

Tyr Phe Asn Glu Ile Gln Gly Lys Thr Lys Gly Asp Glu Asp Tyr
```

```
            1310                1315                1320

Arg Ala Leu Asp Ala Thr Ser Gly Gly Thr Leu Ser His Ser Val
    1325                1330                1335

Met Val Tyr Trp Gly Asp Arg Lys Lys Tyr Gln Ala Leu Leu Asn
    1340                1345                1350

Arg Met Gly Leu Pro Glu Asp Trp Val Glu Gln Ile Asp Glu Asn
    1355                1360                1365

Pro Gly Val Leu Tyr Arg Arg Ala Ala Asn Lys Lys Glu Leu Leu
    1370                1375                1380

Leu Lys Leu Ala Glu Lys Val His Ser Pro Gly Val Thr Ser Ser
    1385                1390                1395

Leu Ser Lys Gly His Val Val Pro Arg Val Val Ala Ala Gly Val
    1400                1405                1410

Tyr Leu Leu Ser Arg His Cys Phe Arg Phe Ser Ser Ser Ile His
    1415                1420                1425

Gly Arg Gly Ser Ala Gln Lys Ala Ser Leu Ile Lys Leu Leu Met
    1430                1435                1440

Met Ser Ser Val Ser Ala Met Lys His Gly Gly Ser Leu Asn Pro
    1445                1450                1455

Asn Gln Glu Arg Met Leu Phe Pro Gln Ala Gln Glu Tyr Asp Arg
    1460                1465                1470

Val Cys Thr Leu Leu Glu Glu Val Glu His Leu Thr Gly Lys Phe
    1475                1480                1485

Val Val Arg Glu Arg Asn Ile Val Arg Ser Arg Ile Asp Leu Phe
    1490                1495                1500

Gln Glu Pro Val Asp Leu Arg Cys Lys Ala Glu Asp Leu Val Ser
    1505                1510                1515

Glu Val Trp Phe Gly Leu Lys Arg Thr Lys Leu Gly Pro Arg Leu
    1520                1525                1530

Leu Lys Glu Glu Trp Asp Lys Leu Arg Ala Ser Phe Ala Trp Leu
    1535                1540                1545

Ser Thr Asp Pro Ser Glu Thr Leu Arg Asp Gly Pro Phe Leu Ser
    1550                1555                1560

His Val Gln Phe Arg Asn Phe Ile Ala His Val Asp Ala Lys Ser
    1565                1570                1575

Arg Ser Val Arg Leu Leu Gly Ala Pro Val Lys Lys Ser Gly Gly
    1580                1585                1590

Val Thr Thr Ile Ser Gln Val Val Arg Met Asn Phe Phe Pro Gly
    1595                1600                1605

Phe Ser Leu Glu Ala Glu Lys Ser Leu Asp Asn Gln Glu Arg Leu
    1610                1615                1620

Glu Ser Ile Ser Ile Leu Lys His Val Leu Phe Met Val Leu Asn
    1625                1630                1635

Gly Pro Tyr Thr Glu Glu Tyr Lys Leu Glu Met Ile Ile Glu Ala
    1640                1645                1650

Phe Ser Thr Leu Val Ile Pro Gln Pro Ser Glu Val Ile Arg Lys
    1655                1660                1665

Ser Arg Thr Met Thr Leu Cys Leu Leu Ser Asn Tyr Leu Ser Ser
    1670                1675                1680

Arg Gly Gly Ser Ile Leu Asp Gln Ile Glu Arg Ala Gln Ser Gly
    1685                1690                1695

Thr Leu Gly Gly Phe Ser Lys Pro Gln Lys Thr Phe Ile Arg Pro
    1700                1705                1710
```

Gly Gly Gly Ile Gly Tyr Lys Gly Lys Gly Val Trp Thr Gly Val
    1715                1720                1725

Met Glu Asp Thr His Val Gln Ile Leu Ile Asp Gly Asp Gly Thr
    1730                1735                1740

Ser Asn Trp Leu Glu Glu Ile Arg Leu Ser Ser Asp Ala Arg Leu
    1745                1750                1755

Tyr Asp Val Ile Glu Ser Ile Arg Arg Leu Cys Asp Asp Leu Gly
    1760                1765                1770

Ile Asn Asn Arg Val Ala Ser Ala Tyr Arg Gly His Cys Met Val
    1775                1780                1785

Arg Leu Ser Gly Phe Lys Ile Lys Pro Ala Ser Arg Thr Asp Gly
    1790                1795                1800

Cys Pro Val Arg Ile Met Glu Arg Gly Phe Arg Ile Arg Glu Leu
    1805                1810                1815

Gln Asn Pro Asp Glu Val Lys Met Arg Val Arg Gly Asp Ile Leu
    1820                1825                1830

Asn Leu Ser Val Thr Ile Gln Glu Gly Arg Val Met Asn Ile Leu
    1835                1840                1845

Ser Tyr Arg Pro Arg Asp Thr Asp Ile Ser Glu Ser Ala Ala Ala
    1850                1855                1860

Tyr Leu Trp Ser Asn Arg Asp Leu Phe Ser Phe Gly Lys Lys Glu
    1865                1870                1875

Pro Ser Cys Ser Trp Ile Cys Leu Lys Thr Leu Asp Asn Trp Ala
    1880                1885                1890

Trp Ser His Ala Ser Val Leu Leu Ala Asn Asp Arg Lys Thr Gln
    1895                1900                1905

Gly Ile Asp Asn Lys Ala Met Gly Asn Ile Phe Arg Asp Cys Leu
    1910                1915                1920

Glu Gly Ser Leu Arg Lys Gln Gly Leu Met Arg Ser Lys Leu Thr
    1925                1930                1935

Glu Met Val Glu Lys Asn Val Val Pro Leu Thr Thr Gln Glu Leu
    1940                1945                1950

Val Asp Ile Leu Glu Glu Asp Ile Asp Phe Ser Asp Val Ile Ala
    1955                1960                1965

Val Glu Leu Ser Glu Gly Ser Leu Asp Ile Glu Ser Ile Phe Asp
    1970                1975                1980

Gly Ala Pro Ile Leu Trp Ser Ala Glu Val Glu Glu Phe Gly Glu
    1985                1990                1995

Gly Val Val Ala Val Ser Tyr Ser Ser Lys Tyr Tyr His Leu Thr
    2000                2005                2010

Leu Met Asp Gln Ala Ala Ile Thr Met Cys Ala Ile Met Gly Lys
    2015                2020                2025

Glu Gly Cys Arg Gly Leu Leu Thr Glu Lys Arg Cys Met Ala Ala
    2030                2035                2040

Ile Arg Glu Gln Val Arg Pro Phe Leu Ile Phe Leu Gln Ile Pro
    2045                2050                2055

Glu Asp Ser Ile Ser Trp Val Ser Asp Gln Phe Cys Asp Ser Arg
    2060                2065                2070

Gly Leu Asp Glu Glu Ser Thr Ile Met Trp Gly
    2075                2080

<210> SEQ ID NO 14
<211> LENGTH: 1073

```
<212> TYPE: PRT
<213> ORGANISM: Unknown
<220> FEATURE:
<223> OTHER INFORMATION: severe fever thrombocytopenia syndrome virus
      B-1 M

<400> SEQUENCE: 14
```

| | | | | | | | | | | | | | | | |
|---|---|---|---|---|---|---|---|---|---|---|---|---|---|---|---|
|Met|Met|Lys|Val|Ile|Trp|Phe|Ser|Ser|Leu|Ile|Cys|Leu|Val|Ile|Gln|
|1| | | |5| | | | |10| | | | |15| |
|Cys|Ser|Gly|Asp|Thr|Gly|Pro|Ile|Ile|Cys|Ala|Gly|Pro|Ile|His|Ser|
| | | |20| | | | |25| | | | |30| | |
|Asn|Lys|Ser|Ala|Asn|Ile|Pro|His|Leu|Leu|Gly|Tyr|Ser|Glu|Lys|Ile|
| | |35| | | | |40| | | | |45| | | |
|Cys|Gln|Ile|Asp|Arg|Leu|Ile|His|Val|Ser|Ser|Trp|Leu|Arg|Asn|His|
| |50| | | | |55| | | | |60| | | | |
|Ser|Gln|Phe|Gln|Gly|Tyr|Val|Gly|Gln|Arg|Gly|Arg|Ser|Gln|Val| |
|65| | | | |70| | | | |75| | | | |80|
|Ser|Tyr|Tyr|Pro|Ala|Glu|Asn|Ser|Tyr|Ser|Arg|Trp|Ser|Gly|Leu|Leu|
| | | | |85| | | | |90| | | | |95| |
|Ser|Pro|Cys|Asp|Ala|Asp|Trp|Leu|Gly|Met|Leu|Val|Val|Lys|Lys|Ala|
| | | |100| | | | |105| | | | |110| | |
|Lys|Gly|Ser|Asp|Met|Ile|Val|Pro|Gly|Pro|Ser|Tyr|Lys|Gly|Lys|Val|
| | |115| | | | |120| | | | |125| | | |
|Phe|Phe|Glu|Arg|Pro|Thr|Phe|Asp|Gly|Tyr|Val|Gly|Trp|Gly|Cys|Gly|
| |130| | | | |135| | | | |140| | | | |
|Ser|Gly|Lys|Ser|Arg|Thr|Glu|Ser|Gly|Glu|Leu|Cys|Ser|Ser|Asp|Ser|
|145| | | | |150| | | | |155| | | | |160|
|Gly|Thr|Ser|Ser|Gly|Leu|Leu|Pro|Ser|Asp|Arg|Val|Leu|Trp|Ile|Gly|
| | | | |165| | | | |170| | | | |175| |
|Asp|Val|Ala|Cys|Gln|Pro|Met|Thr|Pro|Ile|Pro|Glu|Glu|Thr|Phe|Leu|
| | | |180| | | | |185| | | | |190| | |
|Glu|Leu|Lys|Ser|Phe|Ser|Gln|Ser|Glu|Phe|Pro|Asp|Ile|Cys|Lys|Ile|
| | |195| | | | |200| | | | |205| | | |
|Asp|Gly|Ile|Val|Phe|Asn|Gln|Cys|Glu|Ser|Glu|Ser|Leu|Pro|Gln|Pro|
| |210| | | | |215| | | | |220| | | | |
|Leu|Asp|Val|Ala|Trp|Met|Asp|Val|Gly|His|Ser|His|Lys|Ile|Ile|Met|
|225| | | | |230| | | | |235| | | | |240|
|Arg|Glu|His|Lys|Thr|Lys|Trp|Val|Gln|Glu|Ser|Ser|Lys|Asp|Phe| |
| | | | |245| | | | |250| | | | |255| |
|Val|Cys|Tyr|Lys|Glu|Gly|Thr|Gly|Pro|Cys|Ser|Glu|Ser|Glu|Glu|Lys|
| | | |260| | | | |265| | | | |270| | |
|Thr|Cys|Lys|Thr|Ser|Gly|Ser|Cys|Arg|Gly|Asp|Met|Gln|Phe|Cys|Lys|
| | |275| | | | |280| | | | |285| | | |
|Val|Ala|Gly|Cys|Glu|His|Gly|Glu|Glu|Ala|Ser|Asp|Ala|Lys|Cys|Arg|
| |290| | | | |295| | | | |300| | | | |
|Cys|Ser|Leu|Val|His|Lys|Pro|Gly|Glu|Val|Val|Ser|Tyr|Gly|Gly| |
|305| | | | |310| | | | |315| | | | |320|
|Met|Arg|Val|Arg|Pro|Lys|Cys|Tyr|Gly|Phe|Ser|Arg|Met|Met|Ala|Thr|
| | | | |325| | | | |330| | | | |335| |
|Leu|Glu|Val|Asn|Pro|Pro|Glu|Gln|Arg|Ile|Gly|Gln|Cys|Thr|Gly|Cys|
| | | |340| | | | |345| | | | |350| | |
|His|Leu|Glu|Cys|Ile|Asn|Gly|Gly|Val|Arg|Leu|Ile|Thr|Leu|Thr|Ser|
| | |355| | | | |360| | | | |365| | | |
|Glu|Leu|Lys|Ser|Ala|Thr|Val|Cys|Ala|Ser|His|Phe|Cys|Ser|Ser|Ala|
| |370| | | | |375| | | | |380| | | | |

```
Thr Ser Gly Lys Lys Ser Thr Glu Ile Gln Phe His Ser Gly Ser Leu
385                 390                 395                 400

Val Gly Lys Thr Thr Ile His Val Lys Gly Ala Leu Val Asp Gly Thr
            405                 410                 415

Glu Phe Thr Phe Glu Gly Ser Cys Met Phe Pro Asp Gly Cys Asp Ala
        420                 425                 430

Val Asp Cys Thr Phe Cys Arg Glu Phe Leu Lys Asn Pro Gln Cys Tyr
            435                 440                 445

Pro Ala Lys Lys Trp Leu Phe Ile Ile Val Ile Leu Leu Gly Tyr
    450                 455                 460

Ala Gly Leu Met Leu Leu Thr Asn Val Leu Lys Ala Ile Gly Val Trp
465                 470                 475                 480

Gly Ser Trp Val Ile Ala Pro Val Lys Leu Met Phe Ala Ile Ile Lys
            485                 490                 495

Lys Leu Met Arg Ser Val Ser Cys Leu Met Gly Lys Leu Met Asp Arg
            500                 505                 510

Gly Arg Gln Val Ile His Glu Glu Ile Gly Glu Asn Arg Glu Gly Asn
            515                 520                 525

Gln Asp Asp Val Arg Ile Glu Met Ala Arg Pro Arg Val Arg His
530                 535                 540

Trp Met Tyr Ser Pro Val Ile Leu Thr Ile Leu Ala Ile Gly Leu Ala
545                 550                 555                 560

Glu Gly Cys Asp Glu Met Val His Ala Asp Ser Lys Leu Val Ser Cys
            565                 570                 575

Lys Gln Gly Ser Gly Asn Met Lys Glu Cys Val Thr Thr Gly Arg Ala
            580                 585                 590

Leu Leu Pro Ala Val Asn Pro Gly Gln Glu Ala Cys Leu His Phe Thr
            595                 600                 605

Ala Pro Gly Ser Pro Asp Ser Lys Cys Leu Lys Ile Lys Val Lys Arg
            610                 615                 620

Ile Asn Leu Lys Cys Lys Lys Ser Ser Ser Tyr Phe Val Pro Asp Ala
625                 630                 635                 640

Arg Ser Arg Cys Thr Ser Val Arg Arg Cys Arg Trp Ala Gly Asp Cys
            645                 650                 655

Gln Ser Gly Cys Pro Ser His Phe Thr Ser Asn Ser Phe Ser Asp Asp
            660                 665                 670

Trp Ala Gly Lys Met Asp Arg Ala Gly Leu Gly Phe Ser Gly Cys Ser
            675                 680                 685

Asp Gly Cys Gly Gly Ala Ala Cys Gly Cys Phe Asn Ala Ala Pro Ser
            690                 695                 700

Cys Ile Phe Trp Arg Lys Trp Val Glu Asn Pro His Gly Ile Ile Trp
705                 710                 715                 720

Lys Val Ser Pro Cys Ala Ala Trp Val Pro Ser Ala Val Ile Glu Leu
            725                 730                 735

Thr Met Pro Ser Gly Glu Val Arg Thr Phe His Pro Met Ser Gly Ile
            740                 745                 750

Pro Thr Gln Val Phe Lys Gly Val Ser Val Thr Tyr Leu Gly Ser Asp
            755                 760                 765

Met Glu Val Ser Gly Leu Thr Asp Leu Cys Glu Ile Glu Glu Leu Lys
            770                 775                 780

Ser Lys Lys Leu Ala Leu Ala Pro Cys Asn Gln Ala Gly Met Gly Val
785                 790                 795                 800
```

-continued

Val Gly Lys Val Gly Glu Ile Gln Cys Ser Ser Glu Ser Ala Arg
            805                 810                 815

Thr Ile Lys Lys Asp Gly Cys Ile Trp Asn Ala Asp Leu Val Gly Ile
        820                 825                 830

Glu Leu Arg Val Asp Asp Ala Val Cys Tyr Ser Lys Ile Thr Ser Val
        835                 840                 845

Glu Ala Val Ala Asn Tyr Ser Ala Ile Pro Thr Thr Ile Gly Gly Leu
    850                 855                 860

Arg Phe Glu Arg Ser His Asp Ser Gln Gly Lys Ile Ser Gly Ser Pro
865                 870                 875                 880

Leu Asp Ile Thr Ala Ile Arg Gly Ser Phe Ser Val Asn Tyr Arg Gly
            885                 890                 895

Leu Arg Leu Ser Leu Ser Glu Val Thr Ala Thr Cys Thr Gly Glu Val
        900                 905                 910

Thr Asn Val Ser Gly Cys Tyr Ser Cys Met Thr Gly Ala Lys Val Ser
        915                 920                 925

Ile Lys Leu His Ser Ser Lys Asn Ser Thr Ala His Val Arg Cys Lys
    930                 935                 940

Gly Asp Glu Thr Ala Phe Ser Val Leu Val Gly Val His Ser Tyr Thr
945                 950                 955                 960

Val Ser Leu Ser Phe Asp His Ala Val Val Asp Glu Gln Cys Gln Leu
            965                 970                 975

Asn Cys Gly Gly His Glu Ser Gln Val Thr Leu Lys Gly Asn Leu Ile
        980                 985                 990

Phe Leu Asp Val Pro Lys Phe Val Asp Gly Ser Tyr Met Gln Thr Tyr
        995                 1000                1005

His Ser Ser Val Pro Thr Gly Ala Asn Ile Pro Ser Pro Thr Asp
    1010                1015                1020

Trp Leu Asn Ala Leu Phe Gly Asn Gly Leu Ser Arg Trp Ile Leu
    1025                1030                1035

Gly Val Ile Gly Val Leu Leu Gly Gly Leu Ala Leu Phe Phe Leu
    1040                1045                1050

Ile Met Ser Leu Phe Lys Leu Gly Thr Lys Gln Val Phe Arg Ser
    1055                1060                1065

Arg Thr Lys Leu Ala
    1070

<210> SEQ ID NO 15
<211> LENGTH: 1073
<212> TYPE: PRT
<213> ORGANISM: Unknown
<220> FEATURE:
<223> OTHER INFORMATION: severe fever thrombocytopenia syndrome virus
      B-1 NP

<400> SEQUENCE: 15

Met Met Lys Val Ile Trp Phe Ser Ser Leu Ile Cys Leu Val Ile Gln
1               5                   10                  15

Cys Ser Gly Asp Thr Gly Pro Ile Ile Cys Ala Gly Pro Ile His Ser
            20                  25                  30

Asn Lys Ser Ala Asn Ile Pro His Leu Leu Gly Tyr Ser Glu Lys Ile
        35                  40                  45

Cys Gln Ile Asp Arg Leu Ile His Val Ser Ser Trp Leu Arg Asn His
    50                  55                  60

Ser Gln Phe Gln Gly Tyr Val Gly Gln Arg Gly Gly Arg Ser Gln Val
65                  70                  75                  80

```
Ser Tyr Tyr Pro Ala Glu Asn Ser Tyr Ser Arg Trp Ser Gly Leu Leu
                85                  90                  95

Ser Pro Cys Asp Ala Asp Trp Leu Gly Met Leu Val Val Lys Lys Ala
            100                 105                 110

Lys Gly Ser Asp Met Ile Val Pro Gly Pro Ser Tyr Lys Gly Lys Val
        115                 120                 125

Phe Phe Glu Arg Pro Thr Phe Asp Gly Tyr Val Gly Trp Gly Cys Gly
    130                 135                 140

Ser Gly Lys Ser Arg Thr Glu Ser Gly Glu Leu Cys Ser Ser Asp Ser
145                 150                 155                 160

Gly Thr Ser Ser Gly Leu Leu Pro Ser Asp Arg Val Leu Trp Ile Gly
                165                 170                 175

Asp Val Ala Cys Gln Pro Met Thr Pro Ile Pro Glu Glu Thr Phe Leu
            180                 185                 190

Glu Leu Lys Ser Phe Ser Gln Ser Glu Phe Pro Asp Ile Cys Lys Ile
        195                 200                 205

Asp Gly Ile Val Phe Asn Gln Cys Glu Ser Glu Ser Leu Pro Gln Pro
    210                 215                 220

Leu Asp Val Ala Trp Met Asp Val Gly His Ser His Lys Ile Ile Met
225                 230                 235                 240

Arg Glu His Lys Thr Lys Trp Val Gln Glu Ser Ser Lys Asp Phe
                245                 250                 255

Val Cys Tyr Lys Glu Gly Thr Gly Pro Cys Ser Glu Ser Glu Glu Lys
            260                 265                 270

Thr Cys Lys Thr Ser Gly Ser Cys Arg Gly Asp Met Gln Phe Cys Lys
        275                 280                 285

Val Ala Gly Cys Glu His Gly Glu Glu Ala Ser Asp Ala Lys Cys Arg
    290                 295                 300

Cys Ser Leu Val His Lys Pro Gly Glu Val Val Ser Tyr Gly Gly
305                 310                 315                 320

Met Arg Val Arg Pro Lys Cys Tyr Gly Phe Ser Arg Met Met Ala Thr
                325                 330                 335

Leu Glu Val Asn Pro Pro Glu Gln Arg Ile Gly Gln Cys Thr Gly Cys
            340                 345                 350

His Leu Glu Cys Ile Asn Gly Gly Val Arg Leu Ile Thr Leu Thr Ser
        355                 360                 365

Glu Leu Lys Ser Ala Thr Val Cys Ala Ser His Phe Cys Ser Ser Ala
    370                 375                 380

Thr Ser Gly Lys Lys Ser Thr Glu Ile Gln Phe His Ser Gly Ser Leu
385                 390                 395                 400

Val Gly Lys Thr Thr Ile His Val Lys Gly Ala Leu Val Asp Gly Thr
                405                 410                 415

Glu Phe Thr Phe Glu Gly Ser Cys Met Phe Pro Asp Gly Cys Asp Ala
            420                 425                 430

Val Asp Cys Thr Phe Cys Arg Glu Phe Leu Lys Asn Pro Gln Cys Tyr
        435                 440                 445

Pro Ala Lys Lys Trp Leu Phe Ile Ile Ile Val Ile Leu Leu Gly Tyr
    450                 455                 460

Ala Gly Leu Met Leu Leu Thr Asn Val Leu Lys Ala Ile Gly Val Trp
465                 470                 475                 480

Gly Ser Trp Val Ile Ala Pro Val Lys Leu Met Phe Ala Ile Ile Lys
                485                 490                 495
```

```
Lys Leu Met Arg Ser Val Ser Cys Leu Met Gly Lys Leu Met Asp Arg
            500                 505                 510

Gly Arg Gln Val Ile His Glu Glu Ile Gly Glu Asn Arg Glu Gly Asn
        515                 520                 525

Gln Asp Asp Val Arg Ile Glu Met Ala Arg Pro Arg Val Arg His
    530                 535                 540

Trp Met Tyr Ser Pro Val Ile Leu Thr Ile Leu Ala Ile Gly Leu Ala
545                 550                 555                 560

Glu Gly Cys Asp Glu Met Val His Ala Asp Ser Lys Leu Val Ser Cys
                565                 570                 575

Lys Gln Gly Ser Gly Asn Met Lys Glu Cys Val Thr Thr Gly Arg Ala
            580                 585                 590

Leu Leu Pro Ala Val Asn Pro Gly Gln Glu Ala Cys Leu His Phe Thr
        595                 600                 605

Ala Pro Gly Ser Pro Asp Ser Lys Cys Leu Lys Ile Lys Val Lys Arg
    610                 615                 620

Ile Asn Leu Lys Cys Lys Lys Ser Ser Tyr Phe Val Pro Asp Ala
625                 630                 635                 640

Arg Ser Arg Cys Thr Ser Val Arg Arg Cys Arg Trp Ala Gly Asp Cys
                645                 650                 655

Gln Ser Gly Cys Pro Ser His Phe Thr Ser Asn Ser Phe Ser Asp Asp
            660                 665                 670

Trp Ala Gly Lys Met Asp Arg Ala Gly Leu Gly Phe Ser Gly Cys Ser
        675                 680                 685

Asp Gly Cys Gly Gly Ala Ala Cys Gly Cys Phe Asn Ala Ala Pro Ser
    690                 695                 700

Cys Ile Phe Trp Arg Lys Trp Val Glu Asn Pro His Gly Ile Ile Trp
705                 710                 715                 720

Lys Val Ser Pro Cys Ala Ala Trp Val Pro Ser Ala Val Ile Glu Leu
                725                 730                 735

Thr Met Pro Ser Gly Glu Val Arg Thr Phe His Pro Met Ser Gly Ile
            740                 745                 750

Pro Thr Gln Val Phe Lys Gly Val Ser Val Thr Tyr Leu Gly Ser Asp
        755                 760                 765

Met Glu Val Ser Gly Leu Thr Asp Leu Cys Glu Ile Glu Glu Leu Lys
    770                 775                 780

Ser Lys Lys Leu Ala Leu Ala Pro Cys Asn Gln Ala Gly Met Gly Val
785                 790                 795                 800

Val Gly Lys Val Gly Glu Ile Gln Cys Ser Ser Glu Glu Ser Ala Arg
                805                 810                 815

Thr Ile Lys Lys Asp Gly Cys Ile Trp Asn Ala Asp Leu Val Gly Ile
            820                 825                 830

Glu Leu Arg Val Asp Asp Ala Val Cys Tyr Ser Lys Ile Thr Ser Val
        835                 840                 845

Glu Ala Val Ala Asn Tyr Ser Ala Ile Pro Thr Thr Ile Gly Gly Leu
    850                 855                 860

Arg Phe Glu Arg Ser His Asp Ser Gln Gly Lys Ile Ser Gly Ser Pro
865                 870                 875                 880

Leu Asp Ile Thr Ala Ile Arg Gly Ser Phe Ser Val Asn Tyr Arg Gly
                885                 890                 895

Leu Arg Leu Ser Leu Ser Glu Val Thr Ala Thr Cys Thr Gly Glu Val
            900                 905                 910

Thr Asn Val Ser Gly Cys Tyr Ser Cys Met Thr Gly Ala Lys Val Ser
```

```
            915                 920                 925
Ile Lys Leu His Ser Ser Lys Asn Ser Thr Ala His Val Arg Cys Lys
        930                 935                 940

Gly Asp Glu Thr Ala Phe Ser Val Leu Val Gly Val His Ser Tyr Thr
945                 950                 955                 960

Val Ser Leu Ser Phe Asp His Ala Val Val Asp Glu Gln Cys Gln Leu
                965                 970                 975

Asn Cys Gly Gly His Glu Ser Gln Val Thr Leu Lys Gly Asn Leu Ile
            980                 985                 990

Phe Leu Asp Val Pro Lys Phe Val Asp Gly Ser Tyr Met Gln Thr Tyr
        995                 1000                1005

His Ser Ser Val Pro Thr Gly Ala Asn Ile Pro Ser Pro Thr Asp
    1010                1015                1020

Trp Leu Asn Ala Leu Phe Gly Asn Gly Leu Ser Arg Trp Ile Leu
    1025                1030                1035

Gly Val Ile Gly Val Leu Leu Gly Gly Leu Ala Leu Phe Phe Leu
    1040                1045                1050

Ile Met Ser Leu Phe Lys Leu Gly Thr Lys Gln Val Phe Arg Ser
    1055                1060                1065

Arg Thr Lys Leu Ala
    1070

<210> SEQ ID NO 16
<211> LENGTH: 293
<212> TYPE: PRT
<213> ORGANISM: Unknown
<220> FEATURE:
<223> OTHER INFORMATION: severe fever thrombocytopenia syndrome virus
      B-1 NS

<400> SEQUENCE: 16

Met Ser Leu Ser Lys Cys Ser Asn Val Asp Leu Lys Ser Val Ala Met
1               5                   10                  15

Asn Ala Asn Thr Val Arg Leu Glu Pro Ser Leu Gly Glu Tyr Pro Thr
            20                  25                  30

Leu Arg Arg Asp Leu Val Glu Cys Ser Cys Ser Val Leu Thr Leu Ser
        35                  40                  45

Met Val Lys Arg Met Gly Lys Met Thr Asn Thr Val Trp Leu Phe Gly
    50                  55                  60

Asn Pro Lys Asn Pro Leu His Gln Leu Glu Pro Gly Leu Glu Gln Leu
65                  70                  75                  80

Leu Asp Met Tyr Tyr Lys Asp Met Arg Cys Tyr Ser Gln Arg Glu Leu
                85                  90                  95

Ser Ala Leu Arg Trp Pro Ser Gly Lys Pro Ser Val Trp Phe Leu Gln
            100                 105                 110

Ala Ala His Met Phe Phe Ser Ile Lys Asn Ser Trp Ala Met Glu Thr
        115                 120                 125

Gly Arg Glu Asn Trp Arg Gly Leu Phe His Arg Ile Thr Lys Gly Lys
    130                 135                 140

Lys Tyr Leu Phe Glu Gly Asp Met Ile Leu Asp Ser Leu Glu Ala Ile
145                 150                 155                 160

Glu Lys Arg Arg Leu Arg Leu Gly Leu Pro Glu Ile Leu Ile Thr Gly
                165                 170                 175

Leu Ser Pro Ile Leu Asp Val Ala Leu Leu Gln Ile Glu Ser Leu Ala
            180                 185                 190
```

```
Arg Leu Arg Gly Met Ser Leu Asn His His Leu Phe Thr Ser Ser Ser
        195                 200                 205

Leu Arg Lys Pro Leu Leu Asp Cys Trp Asp Phe Phe Ile Pro Ile Arg
210                 215                 220

Lys Lys Arg Thr Asp Gly Ser Tyr Ser Ile Leu Asp Glu Asp Asp Glu
225                 230                 235                 240

Leu Gly Val Leu Gln Gly Tyr Pro Tyr Leu Met Ala His Tyr Leu Asn
                245                 250                 255

Arg Cys Pro Phe His Asn Leu Ile Arg Phe Asp Glu Glu Leu Arg Thr
                260                 265                 270

Ala Ala Leu Asn Thr Ile Trp Gly Arg Asp Trp Pro Ala Ile Gly Asp
            275                 280                 285

Leu Pro Lys Glu Val
        290

<210> SEQ ID NO 17
<211> LENGTH: 2084
<212> TYPE: PRT
<213> ORGANISM: Unknown
<220> FEATURE:
<223> OTHER INFORMATION: severe fever thrombocytopenia syndrome virus
      B-2 L

<400> SEQUENCE: 17

Met Asn Leu Glu Val Leu Cys Gly Arg Ile Asn Val Glu Asn Gly Leu
1               5                   10                  15

Ser Leu Gly Glu Pro Gly Leu Tyr Asp Gln Ile Tyr Asp Arg Pro Gly
            20                  25                  30

Leu Pro Asp Leu Asp Val Thr Val Asp Ala Thr Gly Val Thr Val Asp
        35                  40                  45

Ile Gly Ala Val Pro Asp Ser Ala Ser Gln Leu Gly Ser Ser Ile Asn
    50                  55                  60

Ala Gly Leu Ile Thr Ile Gln Leu Ser Glu Ala Tyr Lys Ile Asn His
65                  70                  75                  80

Asp Phe Thr Phe Ser Gly Leu Ser Lys Thr Thr Asp Arg Arg Leu Ser
                85                  90                  95

Glu Val Phe Pro Ile Thr His Asp Gly Ser Asp Gly Met Thr Pro Asp
            100                 105                 110

Val Ile His Thr Arg Leu Asp Gly Thr Ile Val Val Glu Phe Ser
        115                 120                 125

Thr Thr Arg Ser His Asn Ile Gly Gly Leu Glu Thr Ala Tyr Arg Thr
    130                 135                 140

Lys Ile Glu Lys Tyr Arg Asp Pro Ile Ser Arg Arg Val Asp Ile Met
145                 150                 155                 160

Glu Asn Pro Arg Val Phe Phe Gly Val Ile Val Ser Ser Gly Gly
                165                 170                 175

Val Leu Ser Asn Met Pro Leu Thr Gln Asp Glu Ala Glu Leu Met
            180                 185                 190

Tyr Arg Phe Cys Ile Ala Asn Glu Ile Tyr Thr Lys Ala Arg Ser Met
        195                 200                 205

Asp Ala Asp Ile Glu Leu Gln Lys Ser Glu Glu Leu Glu Ala Ile
    210                 215                 220

Ser Arg Ala Leu Ser Phe Phe Ser Leu Phe Glu Pro Asn Ile Glu Lys
225                 230                 235                 240

Val Glu Gly Thr Phe Pro Asn Ser Glu Ile Glu Met Leu Glu Gln Phe
                245                 250                 255
```

```
Leu Ser Thr Pro Ala Asp Val Asp Phe Ile Thr Lys Thr Leu Lys Ala
            260                 265                 270
Lys Glu Val Glu Ala Tyr Ala Asp Leu Cys Asp Ser His Tyr Leu Lys
            275                 280                 285
Pro Glu Lys Thr Ile Gln Glu Arg Leu Glu Ile Asn Arg Cys Glu Ala
            290                 295                 300
Ile Asp Lys Thr Gln Asp Leu Leu Ala Ser Leu His Ala Arg Ser Asn
305                 310                 315                 320
Lys Gln Thr Ser Leu Asn Arg Gly Thr Val Lys Leu Pro Pro Trp Leu
            325                 330                 335
Pro Lys Pro Ser Ser Glu Ser Ile Asp Ile Lys Thr Asp Ser Gly Phe
            340                 345                 350
Gly Ser Leu Met Asp His Gly Ala Tyr Gly Glu Leu Trp Ala Lys Cys
            355                 360                 365
Leu Leu Asp Val Ser Leu Gly Asn Val Glu Gly Val Ile Ser Asp Pro
            370                 375                 380
Ala Lys Glu Leu Asp Ile Ala Ile Ser Asp Asp Pro Glu Lys Asp Thr
385                 390                 395                 400
Pro Lys Glu Ala Lys Ile Thr Tyr Arg Arg Phe Lys Pro Ala Leu Ser
            405                 410                 415
Ser Ser Ala Arg Gln Glu Phe Ser Leu Gln Gly Val Glu Gly Lys Lys
            420                 425                 430
Trp Lys Arg Met Ala Ala Asn Gln Lys Lys Glu Lys Glu Ser His Glu
            435                 440                 445
Ala Leu Ser Pro Phe Leu Asp Val Glu Asp Ile Gly Asp Phe Leu Thr
            450                 455                 460
Phe Asn Asn Leu Leu Ala Asp Ser Arg Tyr Gly Asp Glu Ser Val Gln
465                 470                 475                 480
Arg Ala Val Ser Ile Leu Leu Glu Lys Ala Ser Ala Met Gln Asn Thr
            485                 490                 495
Glu Leu Thr His Ala Leu Asn Asp Ser Phe Lys Arg Asn Leu Ser Ser
            500                 505                 510
Asn Val Val Gln Trp Ser Leu Trp Val Ser Cys Leu Ala Gln Glu Leu
            515                 520                 525
Ala Ser Ala Leu Lys Gln His Cys Arg Ala Gly Glu Phe Ile Ile Lys
            530                 535                 540
Lys Leu Lys Phe Trp Pro Ile Tyr Val Ile Lys Pro Thr Lys Ser
545                 550                 555                 560
Ser Ser His Ile Phe Tyr Ser Leu Gly Ile Arg Lys Ala Asp Val Thr
            565                 570                 575
Arg Arg Leu Thr Gly Arg Val Phe Ser Asp Thr Ile Asp Ala Gly Glu
            580                 585                 590
Trp Glu Leu Thr Glu Phe Lys Ser Leu Lys Thr Cys Lys Leu Thr Asn
            595                 600                 605
Leu Val Asn Leu Pro Cys Thr Met Leu Asn Ser Ile Ala Phe Trp Arg
            610                 615                 620
Glu Lys Leu Gly Val Ala Pro Trp Leu Arg Lys Pro Cys Ser Glu
625                 630                 635                 640
Leu Arg Glu Gln Val Gly Leu Thr Phe Leu Ile Ser Leu Glu Asp Lys
            645                 650                 655
Ser Lys Thr Glu Glu Ile Ile Thr Leu Thr Arg Tyr Thr Gln Met Glu
            660                 665                 670
```

```
Gly Phe Val Ser Pro Pro Met Leu Pro Lys Pro Gln Lys Met Leu Gly
            675                 680                 685

Lys Leu Asp Gly Pro Leu Arg Thr Lys Leu Gln Val Tyr Leu Leu Arg
    690                 695                 700

Lys His Leu Asp Cys Met Val Arg Ile Ala Ser Gln Pro Phe Ser Leu
705                 710                 715                 720

Ile Pro Arg Glu Gly Arg Val Glu Trp Gly Thr Phe His Ala Ile
                725                 730                 735

Ser Gly Arg Ser Thr Asn Leu Glu Asn Met Val Asn Ser Trp Tyr Ile
            740                 745                 750

Gly Tyr Tyr Lys Asn Lys Glu Glu Ser Thr Glu Leu Asn Ala Leu Gly
    755                 760                 765

Glu Met Tyr Lys Lys Ile Val Glu Met Glu Glu Asp Lys Pro Ser Ser
    770                 775                 780

Pro Glu Phe Leu Gly Trp Gly Asp Thr Asp Ser Pro Lys Lys His Glu
785                 790                 795                 800

Phe Ser Arg Ser Phe Leu Arg Ala Ala Cys Ser Ser Leu Glu Arg Glu
                805                 810                 815

Ile Ala Gln Arg His Gly Arg Gln Trp Lys Gln Asn Leu Glu Glu Arg
                820                 825                 830

Val Leu Arg Glu Ile Gly Thr Lys Asn Ile Leu Asp Leu Ala Ser Met
    835                 840                 845

Lys Ala Thr Ser Asn Phe Ser Lys Asp Trp Glu Leu Tyr Ser Glu Val
    850                 855                 860

Gln Thr Lys Glu Tyr His Arg Ser Lys Leu Leu Glu Lys Met Ala Thr
865                 870                 875                 880

Leu Ile Glu Lys Gly Val Met Trp Tyr Ile Asp Ala Val Gly Gln Ala
                885                 890                 895

Trp Lys Ala Val Leu Asp Asp Gly Cys Met Arg Ile Cys Leu Phe Lys
                900                 905                 910

Lys Asn Gln His Gly Gly Leu Arg Glu Ile Tyr Val Met Asp Ala Asn
    915                 920                 925

Ala Arg Leu Val Gln Phe Gly Val Glu Thr Met Ala Arg Cys Val Cys
    930                 935                 940

Glu Leu Ser Pro His Glu Thr Val Ala Asn Pro Arg Leu Lys Asn Ser
945                 950                 955                 960

Ile Ile Glu Asn His Gly Leu Lys Ser Ala Arg Ser Leu Gly Pro Gly
                965                 970                 975

Ser Ile Asn Ile Asn Ser Ser Asp Ala Lys Lys Trp Asn Gln Gly
            980                 985                 990

His Tyr Thr Thr Lys Leu Ala Leu Val Leu Cys Trp Phe Met Pro Ala
    995                 1000                1005

Lys Phe His Arg Phe Ile Trp Ala Ala Ile Ser Met Phe Arg Arg
    1010                1015                1020

Lys Lys Met Met Val Asp Leu Arg Phe Leu Ala His Leu Ser Ser
    1025                1030                1035

Lys Ser Glu Ser Arg Ser Ser Asp Pro Phe Arg Glu Ala Met Thr
    1040                1045                1050

Asp Ala Phe His Gly Asn Arg Glu Val Ser Trp Met Asp Lys Gly
    1055                1060                1065

Arg Thr Tyr Ile Lys Thr Glu Thr Gly Met Met Gln Gly Ile Leu
    1070                1075                1080

His Phe Thr Ser Ser Leu Leu His Ser Cys Val Gln Ser Phe Tyr
```

```
              1085                1090                1095
Lys Ser Tyr Phe Val Ser Lys Leu Lys Glu Gly Tyr Met Gly Glu
        1100                1105                1110

Ser Ile Asn Gly Val Val Asp Val Ile Glu Gly Ser Asp Asp Ser
        1115                1120                1125

Ala Ile Met Ile Ser Ile Arg Pro Lys Ser Asp Met Asp Glu Val
        1130                1135                1140

Arg Ser Arg Phe Phe Val Ala Asn Leu Leu His Ser Val Lys Phe
        1145                1150                1155

Leu Asn Pro Leu Phe Gly Ile Tyr Ser Ser Glu Lys Ser Thr Val
        1160                1165                1170

Asn Thr Val Tyr Cys Val Glu Tyr Asn Ser Glu Phe His Phe His
        1175                1180                1185

Arg His Leu Val Arg Pro Thr Leu Arg Trp Ile Ala Ala Ser His
        1190                1195                1200

Gln Ile Ser Glu Thr Glu Ala Leu Ala Ser Arg Gln Glu Asp Tyr
        1205                1210                1215

Ser Asn Leu Leu Thr Gln Cys Leu Glu Gly Gly Ala Ser Phe Ser
        1220                1225                1230

Leu Thr Tyr Leu Ile Gln Cys Ala Gln Leu Leu His His Tyr Met
        1235                1240                1245

Leu Leu Gly Leu Cys Leu His Pro Leu Phe Gly Thr Phe Met Gly
        1250                1255                1260

Met Leu Ile Ser Asp Pro Asp Pro Ala Leu Gly Phe Phe Leu Met
        1265                1270                1275

Asp Asn Pro Ala Phe Ala Gly Gly Ala Gly Phe Arg Phe Asn Leu
        1280                1285                1290

Trp Arg Ala Cys Lys Thr Thr Asp Leu Gly Arg Lys Tyr Ala Tyr
        1295                1300                1305

Tyr Phe Asn Glu Ile Gln Gly Lys Thr Lys Gly Asp Glu Asp Tyr
        1310                1315                1320

Arg Ala Leu Asp Ala Thr Ser Gly Gly Thr Leu Ser His Ser Val
        1325                1330                1335

Met Val Tyr Trp Gly Asp Arg Lys Lys Tyr Gln Ala Leu Leu Asn
        1340                1345                1350

Arg Met Gly Leu Pro Glu Asp Trp Val Glu Gln Ile Asp Glu Asn
        1355                1360                1365

Pro Gly Val Leu Tyr Arg Arg Ala Ala Asn Lys Lys Glu Leu Leu
        1370                1375                1380

Leu Lys Leu Ala Glu Lys Val His Ser Pro Gly Val Thr Ser Ser
        1385                1390                1395

Leu Ser Lys Gly His Val Val Pro Arg Val Val Ala Ala Gly Val
        1400                1405                1410

Tyr Leu Leu Ser Arg His Cys Phe Arg Phe Ser Ser Ser Ile His
        1415                1420                1425

Gly Arg Gly Ser Ala Gln Lys Ala Ser Leu Ile Lys Leu Leu Met
        1430                1435                1440

Met Ser Ser Ile Ser Ala Met Lys His Gly Gly Ser Leu Asn Pro
        1445                1450                1455

Asn Gln Glu Arg Met Leu Phe Pro Gln Ala Gln Glu Tyr Asp Arg
        1460                1465                1470

Val Cys Thr Leu Leu Glu Glu Val Glu His Leu Thr Gly Lys Phe
        1475                1480                1485
```

```
Val Val Arg Glu Arg Asn Ile Val Arg Ser Arg Ile Asp Leu Phe
    1490                1495                1500

Gln Glu Pro Val Asp Leu Arg Cys Lys Ala Glu Asp Leu Val Ser
    1505                1510                1515

Glu Val Trp Phe Gly Leu Lys Arg Thr Lys Leu Gly Pro Arg Leu
    1520                1525                1530

Leu Lys Glu Glu Trp Asp Lys Leu Arg Ala Ser Phe Ala Trp Leu
    1535                1540                1545

Ser Thr Asp Pro Ser Glu Thr Leu Arg Asp Gly Pro Phe Leu Ser
    1550                1555                1560

His Val Gln Phe Arg Asn Phe Ile Ala His Val Asp Ala Lys Ser
    1565                1570                1575

Arg Ser Val Arg Leu Leu Gly Ala Pro Val Lys Lys Ser Gly Gly
    1580                1585                1590

Val Thr Thr Ile Ser Gln Val Val Arg Met Asn Phe Phe Pro Gly
    1595                1600                1605

Phe Ser Leu Glu Ala Glu Lys Ser Leu Asp Asn Gln Glu Arg Leu
    1610                1615                1620

Glu Ser Ile Ser Ile Leu Lys His Val Leu Phe Met Val Leu Asn
    1625                1630                1635

Gly Pro Tyr Thr Glu Glu Tyr Lys Leu Glu Met Ile Ile Glu Ala
    1640                1645                1650

Phe Ser Thr Leu Val Ile Pro Gln Pro Ser Glu Val Ile Arg Lys
    1655                1660                1665

Ser Arg Thr Met Thr Leu Cys Leu Leu Ser Asn Tyr Leu Ser Ser
    1670                1675                1680

Arg Gly Gly Ser Ile Leu Asp Gln Ile Glu Arg Ala Gln Ser Gly
    1685                1690                1695

Thr Leu Gly Gly Phe Ser Lys Pro Gln Lys Thr Phe Ile Arg Pro
    1700                1705                1710

Gly Gly Gly Ile Gly Tyr Lys Gly Lys Gly Val Trp Thr Gly Val
    1715                1720                1725

Met Glu Asp Thr His Val Gln Ile Leu Ile Asp Gly Asp Gly Thr
    1730                1735                1740

Ser Asn Trp Leu Glu Glu Ile Arg Leu Ser Ser Asp Ala Arg Leu
    1745                1750                1755

Tyr Asp Val Ile Glu Ser Ile Arg Arg Leu Cys Asp Asp Leu Gly
    1760                1765                1770

Ile Asn Asn Arg Val Ala Ser Ala Tyr Arg Gly His Cys Met Val
    1775                1780                1785

Arg Leu Ser Gly Phe Lys Ile Lys Pro Ala Ser Arg Thr Asp Gly
    1790                1795                1800

Cys Pro Val Arg Ile Met Glu Arg Gly Phe Arg Ile Arg Glu Leu
    1805                1810                1815

Gln Asn Pro Asp Glu Val Lys Met Arg Val Arg Gly Asp Ile Leu
    1820                1825                1830

Asn Leu Ser Val Thr Ile Gln Glu Gly Arg Val Met Asn Ile Leu
    1835                1840                1845

Ser Tyr Arg Pro Arg Asp Thr Asp Ile Ser Glu Ser Ala Ala Ala
    1850                1855                1860

Tyr Leu Trp Ser Asn Arg Asp Leu Phe Ser Phe Gly Lys Lys Glu
    1865                1870                1875
```

```
Pro Ser Cys Ser Trp Ile Cys Leu Lys Thr Leu Asp Asn Trp Ala
    1880                1885                1890

Trp Ser His Ala Ser Val Leu Leu Ala Asn Asp Arg Lys Thr Gln
    1895                1900                1905

Gly Ile Asp Asn Arg Ala Met Gly Asn Ile Phe Arg Asp Cys Leu
    1910                1915                1920

Glu Gly Ser Leu Arg Lys Gln Gly Leu Met Arg Ser Lys Leu Thr
    1925                1930                1935

Glu Met Val Glu Lys Asn Val Val Pro Leu Thr Thr Gln Glu Leu
    1940                1945                1950

Val Asp Ile Leu Glu Glu Asp Ile Asp Phe Ser Asp Val Ile Ala
    1955                1960                1965

Val Glu Leu Ser Glu Gly Ser Leu Asp Ile Glu Ser Ile Phe Asp
    1970                1975                1980

Gly Ala Pro Ile Leu Trp Ser Ala Glu Val Glu Glu Phe Gly Glu
    1985                1990                1995

Gly Val Val Ala Val Ser Tyr Ser Ser Lys Tyr Tyr His Leu Thr
    2000                2005                2010

Leu Met Asp Gln Ala Ala Ile Thr Met Cys Ala Ile Met Gly Lys
    2015                2020                2025

Glu Gly Cys Arg Gly Leu Leu Thr Glu Lys Arg Cys Met Ala Ala
    2030                2035                2040

Ile Arg Glu Gln Val Arg Pro Phe Leu Ile Phe Leu Gln Ile Pro
    2045                2050                2055

Glu Asp Ser Ile Ser Trp Val Ser Asp Gln Phe Cys Asp Ser Arg
    2060                2065                2070

Gly Leu Asp Glu Glu Ser Thr Ile Met Trp Gly
    2075                2080

<210> SEQ ID NO 18
<211> LENGTH: 1073
<212> TYPE: PRT
<213> ORGANISM: Unknown
<220> FEATURE:
<223> OTHER INFORMATION: severe fever thrombocytopenia syndrome virus
      B-2 M

<400> SEQUENCE: 18

Met Met Lys Val Ile Trp Phe Ser Ser Leu Ile Cys Leu Val Ile Gln
1               5                   10                  15

Cys Ser Gly Asp Thr Gly Pro Ile Ile Cys Ala Gly Pro Ile His Ser
                20                  25                  30

Asn Lys Ser Ala Asp Ile Pro His Leu Leu Gly Tyr Ser Glu Lys Ile
        35                  40                  45

Cys Gln Ile Asp Arg Leu Ile His Val Ser Ser Trp Leu Arg Asn His
    50                  55                  60

Ser Gln Phe Gln Gly Tyr Val Gly Gln Arg Gly Gly Arg Ser Gln Val
65                  70                  75                  80

Ser Tyr Phe Pro Ala Glu Asn Ser Tyr Ser Arg Trp Ser Gly Leu Leu
                85                  90                  95

Ser Pro Cys Asp Ala Asp Trp Leu Gly Met Leu Val Lys Lys Ala
                100                 105                 110

Lys Gly Ser Asp Met Ile Val Pro Gly Pro Ser Tyr Lys Gly Lys Val
        115                 120                 125

Phe Phe Glu Arg Pro Thr Phe Asp Gly Tyr Val Gly Trp Gly Cys Gly
    130                 135                 140
```

-continued

```
Ser Gly Lys Ser Arg Thr Glu Ser Gly Glu Leu Cys Ser Ser Asp Ser
145                 150                 155                 160

Gly Thr Ser Ser Gly Leu Leu Pro Ser Asn Arg Val Leu Trp Ile Gly
                165                 170                 175

Asp Val Ala Cys Gln Pro Met Thr Pro Ile Pro Glu Glu Thr Phe Leu
            180                 185                 190

Glu Leu Lys Ser Phe Ser Gln Ser Glu Phe Pro Asp Ile Cys Lys Ile
                195                 200                 205

Asp Gly Ile Val Phe Asn Gln Cys Glu Ser Glu Ser Leu Pro Gln Pro
        210                 215                 220

Phe Asp Val Ala Trp Met Asp Val Gly His Ser His Lys Ile Ile Met
225                 230                 235                 240

Arg Glu His Lys Thr Lys Trp Val Gln Glu Ser Ser Ser Lys Asp Phe
                245                 250                 255

Val Cys Tyr Lys Glu Gly Thr Gly Pro Cys Ser Glu Ser Glu Glu Lys
                260                 265                 270

Thr Cys Lys Thr Ser Gly Ser Cys Arg Gly Asp Met Gln Phe Cys Lys
            275                 280                 285

Val Ala Gly Cys Glu His Gly Glu Glu Thr Ser Glu Ala Lys Cys Arg
        290                 295                 300

Cys Ser Leu Val His Lys Pro Gly Glu Val Val Ser Tyr Gly Gly
305                 310                 315                 320

Met Arg Val Arg Pro Lys Cys Tyr Gly Phe Ser Arg Met Met Ala Thr
                325                 330                 335

Leu Glu Val Asn Pro Pro Glu Gln Arg Ile Gly Gln Cys Thr Gly Cys
            340                 345                 350

His Leu Glu Cys Ile Asn Gly Gly Val Arg Ile Ile Thr Leu Thr Ser
                355                 360                 365

Glu Leu Lys Ser Ala Thr Val Cys Ala Ser His Phe Cys Ser Ser Ala
        370                 375                 380

Thr Ser Gly Lys Lys Ser Thr Glu Ile Gln Phe His Ser Gly Ser Leu
385                 390                 395                 400

Val Gly Lys Thr Ala Ile His Val Lys Gly Ala Leu Val Asp Gly Thr
                405                 410                 415

Glu Phe Thr Phe Glu Gly Ser Cys Met Phe Pro Asp Gly Cys Asp Ala
            420                 425                 430

Val Asp Cys Thr Phe Cys Arg Glu Phe Leu Lys Asn Pro Gln Cys Tyr
        435                 440                 445

Pro Ala Lys Lys Trp Leu Phe Ile Ile Ile Val Ile Leu Leu Gly Tyr
        450                 455                 460

Ala Gly Leu Met Leu Leu Thr Asn Val Leu Lys Ala Ile Gly Val Trp
465                 470                 475                 480

Gly Ser Trp Val Ile Ala Pro Val Lys Leu Met Phe Ala Ile Ile Lys
                485                 490                 495

Lys Leu Met Arg Ser Val Ser Cys Leu Met Gly Lys Leu Met Asp Arg
            500                 505                 510

Gly Arg Gln Val Ile His Glu Ile Gly Glu Asn Arg Glu Gly Asn
        515                 520                 525

Gln Asp Asp Val Arg Ile Glu Met Ala Arg Pro Arg Val Arg His
        530                 535                 540

Trp Met Tyr Ser Pro Val Ile Leu Thr Ile Leu Ala Ile Gly Leu Ala
545                 550                 555                 560
```

-continued

Glu Gly Cys Asp Glu Met Val His Ala Asp Ser Lys Leu Val Ser Cys
            565                 570                 575

Lys Gln Gly Ser Gly Asn Met Lys Glu Cys Val Thr Thr Gly Arg Ala
        580                 585                 590

Leu Leu Pro Ala Val Asn Pro Gly Gln Glu Ala Cys Leu His Phe Thr
        595                 600                 605

Ala Pro Gly Ser Pro Asp Ser Lys Cys Leu Lys Ile Lys Val Lys Arg
    610                 615                 620

Ile Asn Leu Lys Cys Lys Lys Ser Ser Ser Tyr Phe Val Pro Asp Ala
625                 630                 635                 640

Arg Ser Arg Cys Thr Ser Val Arg Arg Cys Arg Trp Ala Gly Asp Cys
            645                 650                 655

Gln Ser Gly Cys Pro Ser His Phe Thr Ser Asn Ser Phe Ser Asp Asp
            660                 665                 670

Trp Ala Gly Lys Met Asp Arg Ala Gly Leu Gly Phe Ser Gly Cys Ser
        675                 680                 685

Asp Gly Cys Gly Gly Ala Ala Cys Gly Cys Phe Asn Ala Ala Pro Ser
    690                 695                 700

Cys Ile Phe Trp Arg Lys Trp Val Glu Asn Pro His Gly Ile Ile Trp
705                 710                 715                 720

Lys Val Ser Pro Cys Ala Ala Trp Val Pro Ser Ala Val Ile Glu Leu
            725                 730                 735

Thr Met Pro Ser Gly Glu Val Arg Thr Phe His Pro Met Ser Gly Ile
            740                 745                 750

Pro Thr Gln Val Phe Lys Gly Val Ser Val Thr Tyr Leu Gly Ser Asp
        755                 760                 765

Met Glu Val Ser Gly Leu Thr Asp Leu Cys Glu Ile Glu Glu Leu Lys
    770                 775                 780

Ser Lys Lys Leu Ala Leu Ala Pro Cys Asn Gln Ala Gly Met Gly Val
785                 790                 795                 800

Val Gly Lys Val Gly Glu Ile Gln Cys Ser Ser Glu Glu Ser Ala Arg
            805                 810                 815

Thr Ile Lys Lys Asp Gly Cys Ile Trp Asn Ala Asp Leu Val Gly Ile
            820                 825                 830

Glu Leu Arg Val Asp Asp Ala Val Cys Tyr Ser Lys Ile Thr Ser Val
        835                 840                 845

Glu Ala Val Ala Asn Tyr Ser Ala Ile Pro Thr Thr Ile Gly Gly Leu
    850                 855                 860

Arg Phe Glu Arg Ser His Asp Ser Gln Gly Lys Ile Ser Gly Ser Pro
865                 870                 875                 880

Leu Asp Ile Thr Ala Ile Arg Gly Ser Phe Ser Val Asn Tyr Arg Gly
            885                 890                 895

Leu Arg Leu Ser Leu Ser Glu Ile Thr Ala Thr Cys Thr Gly Glu Val
            900                 905                 910

Thr Asn Val Ser Gly Cys Tyr Ser Cys Met Thr Gly Ala Lys Val Ser
        915                 920                 925

Ile Lys Leu His Ser Ser Lys Asn Ser Thr Ala His Val Arg Cys Lys
    930                 935                 940

Gly Asp Glu Thr Ala Phe Ser Val Leu Glu Gly Val His Ser Tyr Thr
945                 950                 955                 960

Val Ser Leu Ser Phe Asp His Ala Val Val Asp Glu Gln Cys Gln Leu
            965                 970                 975

Asn Cys Gly Gly His Glu Ser Gln Val Thr Leu Lys Gly Asn Leu Ile

```
                980             985             990
Phe Leu Asp Val Pro Lys Phe Val Asp Gly Ser Tyr Met Gln Thr Tyr
            995             1000            1005

His Ser Ser Val Pro Thr Gly Ala Asn Ile Pro Ser Pro Thr Asp
    1010            1015            1020

Trp Leu Asn Ala Leu Phe Gly Asn Gly Leu Ser Arg Trp Ile Leu
    1025            1030            1035

Gly Val Ile Gly Val Leu Leu Gly Gly Leu Ala Leu Phe Phe Leu
    1040            1045            1050

Ile Met Ser Leu Phe Lys Leu Gly Thr Lys Gln Val Phe Arg Ser
    1055            1060            1065

Arg Thr Lys Leu Ala
    1070

<210> SEQ ID NO 19
<211> LENGTH: 245
<212> TYPE: PRT
<213> ORGANISM: Unknown
<220> FEATURE:
<223> OTHER INFORMATION: severe fever thrombocytopenia syndrome virus
      B-2 NP

<400> SEQUENCE: 19

Met Ser Glu Trp Ser Arg Ile Ala Val Glu Phe Gly Glu Gln Gln Leu
1               5                   10                  15

Asn Leu Thr Glu Leu Glu Asp Phe Ala Arg Glu Leu Ala Tyr Glu Gly
            20                  25                  30

Leu Asp Pro Ala Leu Ile Ile Lys Leu Lys Glu Thr Gly Gly Asp
        35                  40                  45

Asp Trp Val Arg Asp Thr Lys Phe Ile Ile Val Phe Ala Leu Thr Arg
50                  55                  60

Gly Asn Lys Ile Val Lys Ala Ser Gly Lys Met Ser Asn Ser Gly Ser
65                  70                  75                  80

Lys Arg Leu Met Ala Leu Gln Glu Lys Tyr Gly Leu Val Glu Arg Ala
                85                  90                  95

Glu Thr Arg Leu Ser Ile Thr Pro Val Arg Val Ala Gln Ser Leu Pro
            100                 105                 110

Thr Trp Thr Cys Ala Ala Ala Ala Leu Lys Glu Tyr Leu Pro Val
        115                 120                 125

Gly Pro Ala Val Met Asn Leu Lys Val Glu Asn Tyr Pro Pro Glu Met
130                 135                 140

Met Cys Met Ala Phe Gly Ser Leu Ile Pro Thr Ala Gly Val Ser Glu
145                 150                 155                 160

Ala Thr Thr Lys Thr Leu Met Glu Ala Tyr Ser Leu Trp Gln Asp Ala
                165                 170                 175

Phe Thr Lys Thr Ile Asn Val Lys Met Arg Gly Ala Ser Lys Thr Glu
            180                 185                 190

Val Tyr Asn Ser Phe Arg Asp Pro Leu His Ala Ala Val Asn Ser Val
        195                 200                 205

Phe Phe Pro Asn Asp Val Arg Val Lys Trp Leu Lys Ala Lys Gly Ile
210                 215                 220

Leu Gly Pro Asp Gly Val Pro Ser Arg Ala Ala Glu Val Ala Ala Ala
225                 230                 235                 240

Ala Tyr Arg Asn Leu
            245
```

<210> SEQ ID NO 20
<211> LENGTH: 293
<212> TYPE: PRT
<213> ORGANISM: Unknown
<220> FEATURE:
<223> OTHER INFORMATION: severe fever thrombocytopenia syndrome virus
      B-2 NS

<400> SEQUENCE: 20

Met Ser Leu Ser Lys Cys Ser Asn Val Asp Leu Lys Ser Val Ala Met
1               5                   10                  15

Asn Ala Asn Thr Val Arg Leu Glu Pro Ser Leu Gly Glu Tyr Pro Thr
            20                  25                  30

Leu Arg Arg Asp Leu Val Glu Cys Ser Cys Ser Val Leu Thr Leu Ser
        35                  40                  45

Met Val Lys Arg Met Gly Lys Met Thr Asn Thr Val Trp Leu Phe Gly
50                  55                  60

Asn Pro Lys Asn Pro Leu His Gln Leu Glu Pro Gly Leu Glu Gln Leu
65                  70                  75                  80

Leu Asp Met Tyr Tyr Lys Asp Met Arg Cys Tyr Ser Gln Arg Glu Leu
                85                  90                  95

Ser Ala Leu Arg Trp Pro Ser Gly Lys Pro Ser Val Trp Phe Leu Gln
            100                 105                 110

Ala Ala His Met Phe Phe Ser Ile Lys Asn Ser Trp Ala Met Glu Thr
        115                 120                 125

Gly Arg Glu Asn Trp Arg Gly Leu Phe His Arg Ile Thr Lys Gly Gln
130                 135                 140

Lys Tyr Leu Phe Glu Gly Asp Met Ile Leu Asp Ser Leu Glu Ala Ile
145                 150                 155                 160

Glu Lys Arg Arg Leu Arg Leu Gly Leu Pro Glu Ile Leu Ile Thr Gly
                165                 170                 175

Leu Ser Pro Ile Leu Asp Val Ala Leu Leu Gln Ile Glu Ser Leu Ala
            180                 185                 190

Arg Leu Arg Gly Met Ser Leu Asn His His Leu Phe Thr Ser Ser Ser
        195                 200                 205

Leu Arg Lys Pro Leu Leu Asp Cys Trp Asp Phe Phe Ile Pro Ile Arg
210                 215                 220

Lys Lys Lys Thr Asp Gly Ser Tyr Ser Val Leu Asp Glu Asp Asp Glu
225                 230                 235                 240

Pro Gly Ile Leu Gln Gly Tyr Pro Tyr Leu Met Ala His Tyr Leu Asn
                245                 250                 255

Arg Cys Pro Phe His Asn Leu Ile Arg Phe Asp Glu Glu Leu Arg Thr
            260                 265                 270

Ala Ala Leu Asn Thr Ile Trp Gly Arg Asp Trp Pro Ala Ile Gly Asp
        275                 280                 285

Leu Pro Lys Glu Val
    290

<210> SEQ ID NO 21
<211> LENGTH: 2084
<212> TYPE: PRT
<213> ORGANISM: Unknown
<220> FEATURE:
<223> OTHER INFORMATION: severe fever thrombocytopenia syndrome virus
      B-3 L

<400> SEQUENCE: 21

```
Met Asn Leu Glu Val Leu Cys Gly Arg Ile Asn Val Glu Asn Gly Leu
1               5                   10                  15
Ser Leu Gly Glu Pro Gly Leu Tyr Asp Gln Ile Tyr Asp Arg Pro Gly
            20                  25                  30
Leu Pro Asp Leu Asp Val Thr Val Asp Ala Ile Gly Val Thr Val Asp
            35                  40                  45
Ile Gly Ala Val Pro Asp Ser Ala Ser Gln Leu Gly Ser Ser Ile Asn
50                      55                  60
Ala Gly Leu Ile Thr Ile Gln Leu Ser Glu Ala Tyr Lys Ile Asn His
65                  70                  75                  80
Asp Phe Thr Phe Ser Gly Leu Ser Lys Thr Thr Asp Arg Arg Leu Ser
                85                  90                  95
Glu Val Phe Pro Ile Thr His Asp Gly Ser Asp Gly Met Thr Pro Asp
            100                 105                 110
Val Ile His Thr Arg Leu Asp Gly Thr Ile Val Val Glu Phe Ser
            115                 120                 125
Thr Thr Arg Ser His Asn Ile Gly Gly Leu Glu Ala Ala Tyr Arg Thr
    130                 135                 140
Lys Ile Glu Lys Tyr Arg Asp Pro Ile Ser Arg Arg Val Asp Ile Met
145                 150                 155                 160
Glu Asn Pro Arg Val Phe Phe Gly Val Ile Val Ser Ser Gly Gly
                165                 170                 175
Val Leu Ser Asn Met Pro Leu Thr Gln Asp Glu Ala Glu Leu Met
            180                 185                 190
Tyr Arg Phe Cys Ile Ala Asn Glu Ile Tyr Thr Lys Ala Arg Ser Met
        195                 200                 205
Asp Ala Asp Ile Glu Leu Gln Lys Ser Glu Glu Leu Glu Ala Ile
    210                 215                 220
Ser Arg Ala Leu Ser Phe Phe Ser Leu Phe Glu Pro Asn Ile Glu Arg
225                 230                 235                 240
Val Glu Gly Thr Phe Pro Asn Ser Glu Ile Glu Met Leu Glu Gln Phe
                245                 250                 255
Leu Ser Thr Pro Ala Asp Val Asp Phe Ile Thr Lys Thr Leu Lys Ala
            260                 265                 270
Lys Glu Val Glu Ala Tyr Ala Asp Leu Cys Asp Ser His Tyr Leu Lys
        275                 280                 285
Pro Glu Lys Thr Ile Gln Glu Arg Leu Glu Ile Asn Arg Cys Glu Ala
    290                 295                 300
Ile Asp Lys Thr Gln Asp Leu Leu Ala Ser Leu His Ala Arg Ser Asn
305                 310                 315                 320
Lys Gln Thr Ser Leu Asn Arg Gly Thr Val Lys Leu Pro Pro Trp Leu
            325                 330                 335
Pro Lys Pro Ser Ser Glu Ser Ile Asp Ile Lys Thr Asp Ser Gly Phe
            340                 345                 350
Gly Ser Leu Met Asp His Gly Thr Tyr Gly Glu Leu Trp Ala Lys Cys
        355                 360                 365
Leu Leu Asp Val Ser Leu Gly Asn Val Glu Gly Val Val Ser Asp Pro
    370                 375                 380
Ala Lys Glu Leu Asp Ile Ala Ile Ser Asp Asp Pro Glu Lys Asp Thr
385                 390                 395                 400
Pro Lys Glu Ala Lys Ile Thr Tyr Arg Arg Phe Lys Pro Ala Leu Ser
            405                 410                 415
Ser Ser Ala Arg Gln Glu Phe Ser Leu Gln Gly Val Glu Gly Lys Lys
```

```
                420             425             430
Trp Lys Arg Met Ala Asn Gln Lys Lys Glu Lys Glu Ser His Glu
            435             440             445
Thr Leu Ser Pro Phe Leu Asp Val Glu Asp Ile Gly Asp Phe Leu Thr
        450             455             460
Phe Asn Asn Leu Leu Ala Asp Ser Arg Tyr Gly Asp Glu Ser Val Gln
465             470             475             480
Arg Ala Val Ser Ile Leu Leu Glu Lys Ala Ser Ala Met Gln Asp Thr
            485             490             495
Glu Leu Thr His Ala Leu Asn Asp Ser Phe Lys Arg Asn Leu Ser Ser
        500             505             510
Asn Val Val Gln Trp Ser Leu Trp Val Ser Cys Leu Ala Gln Glu Leu
    515             520             525
Ala Ser Ala Leu Lys Gln His Cys Arg Ala Gly Glu Phe Ile Ile Lys
    530             535             540
Lys Leu Lys Phe Trp Pro Ile Tyr Val Ile Ile Lys Pro Thr Lys Ser
545             550             555             560
Ser Ser His Ile Phe Tyr Ser Leu Gly Ile Arg Lys Ala Asp Val Thr
            565             570             575
Arg Arg Leu Thr Gly Arg Val Phe Ser Asp Thr Ile Asp Ala Gly Glu
        580             585             590
Trp Glu Leu Thr Glu Phe Lys Ser Leu Lys Thr Cys Lys Leu Thr Asn
    595             600             605
Leu Val Asn Leu Pro Cys Thr Met Leu Asn Ser Ile Ala Phe Trp Arg
    610             615             620
Glu Lys Leu Gly Val Ala Pro Trp Leu Val Arg Lys Pro Cys Ser Glu
625             630             635             640
Leu Arg Glu Gln Val Gly Leu Thr Phe Leu Ile Ser Leu Glu Asp Lys
            645             650             655
Ser Lys Thr Glu Glu Ile Ile Thr Leu Thr Arg Tyr Thr Gln Met Glu
        660             665             670
Gly Phe Val Ser Pro Pro Met Leu Pro Lys Pro Gln Lys Met Leu Gly
            675             680             685
Lys Leu Asp Gly Pro Leu Arg Thr Lys Leu Gln Val Tyr Leu Leu Arg
        690             695             700
Lys His Leu Asp Cys Met Val Arg Ile Ala Ser Gln Pro Phe Ser Leu
705             710             715             720
Ile Pro Arg Glu Gly Arg Val Glu Trp Gly Gly Thr Phe His Ala Ile
            725             730             735
Ser Gly Arg Ser Thr Asn Leu Glu Asn Met Val Asn Ser Trp Tyr Ile
        740             745             750
Gly Tyr Tyr Lys Asn Lys Glu Glu Ser Thr Glu Leu Asn Ala Leu Gly
        755             760             765
Glu Met Tyr Lys Lys Ile Val Glu Met Glu Glu Asp Lys Pro Ser Ser
    770             775             780
Pro Lys Phe Leu Gly Trp Gly Asp Thr Asp Ser Pro Lys Lys His Glu
785             790             795             800
Phe Ser Arg Ser Phe Leu Arg Ala Ala Cys Ser Ser Leu Glu Arg Glu
            805             810             815
Ile Ala Gln Arg His Gly Arg Gln Trp Lys Gln Asn Leu Glu Glu Arg
        820             825             830
Val Leu Arg Glu Ile Gly Thr Lys Asn Ile Leu Asp Leu Ala Ser Met
    835             840             845
```

```
Lys Ala Thr Ser Asn Phe Ser Lys Asp Trp Glu Leu Tyr Ser Glu Val
    850                 855                 860

Gln Thr Lys Glu Tyr His Arg Ser Lys Leu Leu Glu Lys Met Ala Thr
865                 870                 875                 880

Leu Ile Glu Lys Gly Val Met Trp Tyr Ile Asp Ala Val Gly Gln Ala
                885                 890                 895

Trp Lys Ala Val Leu Asp Asp Gly Cys Met Arg Ile Cys Leu Phe Lys
                900                 905                 910

Lys Asn Gln His Gly Gly Leu Arg Glu Ile Tyr Val Met Asp Ala Asn
                915                 920                 925

Ala Arg Leu Val Gln Phe Gly Val Glu Thr Met Ala Arg Cys Val Cys
    930                 935                 940

Glu Leu Ser Pro His Glu Thr Val Ala Asn Pro Arg Leu Lys Asn Ser
945                 950                 955                 960

Ile Ile Glu Asn His Gly Leu Lys Ser Ala Arg Ser Leu Gly Pro Gly
                965                 970                 975

Ser Ile Asn Ile Asn Ser Ser Asn Asp Ala Lys Lys Trp Asn Gln Gly
                980                 985                 990

His Tyr Thr Thr Lys Leu Ala Leu Val Leu Cys Trp Phe Met Pro Ala
            995                 1000                1005

Lys Phe His Arg Phe Ile Trp Ala Ala Ile Ser Met Phe Arg Arg
    1010                1015                1020

Lys Lys Met Met Val Asp Leu Arg Phe Leu Ala His Leu Ser Ser
    1025                1030                1035

Lys Ser Glu Ser Arg Ser Ser Asp Pro Phe Arg Glu Ala Met Thr
    1040                1045                1050

Asp Ala Phe His Gly Asn Arg Glu Val Ser Trp Met Asp Lys Gly
    1055                1060                1065

Arg Thr Tyr Ile Lys Thr Glu Thr Gly Met Met Gln Gly Ile Leu
    1070                1075                1080

His Phe Thr Ser Ser Leu Leu His Ser Cys Val Gln Ser Phe Tyr
    1085                1090                1095

Lys Ser Tyr Phe Val Ser Lys Leu Lys Glu Gly Tyr Met Gly Glu
    1100                1105                1110

Ser Ile Ser Gly Val Val Asp Val Ile Glu Gly Ser Asp Asp Ser
    1115                1120                1125

Ala Ile Met Ile Ser Ile Arg Pro Lys Ser Asp Met Asp Glu Val
    1130                1135                1140

Arg Ser Arg Phe Phe Val Ala Asn Leu Leu His Ser Val Lys Phe
    1145                1150                1155

Leu Asn Pro Leu Phe Gly Ile Tyr Ser Ser Glu Lys Ser Thr Val
    1160                1165                1170

Asn Thr Val Tyr Cys Val Glu Tyr Asn Ser Glu Phe His Phe His
    1175                1180                1185

Arg His Leu Val Arg Pro Thr Leu Arg Trp Ile Ala Ala Ser His
    1190                1195                1200

Gln Ile Ser Glu Thr Glu Ala Leu Ala Ser Arg Gln Glu Asp Tyr
    1205                1210                1215

Ser Asn Leu Leu Thr Gln Cys Leu Glu Gly Gly Ala Ser Phe Ser
    1220                1225                1230

Leu Thr Tyr Leu Ile Gln Cys Ala Gln Leu Leu His His Tyr Met
    1235                1240                1245
```

```
Leu Leu Gly Leu Cys Leu His Pro Leu Phe Gly Thr Phe Met Gly
    1250                1255                1260

Met Leu Ile Ser Asp Pro Asp Pro Ala Leu Gly Phe Phe Leu Met
    1265                1270                1275

Asp Asn Pro Ala Phe Ala Gly Gly Ala Gly Phe Arg Phe Asn Leu
    1280                1285                1290

Trp Arg Ala Cys Lys Thr Thr Asp Leu Gly Arg Lys Tyr Ala Tyr
    1295                1300                1305

Tyr Phe Asn Glu Ile Gln Gly Lys Thr Lys Gly Asp Glu Asp Tyr
    1310                1315                1320

Arg Ala Leu Asp Ala Thr Ser Gly Gly Thr Leu Ser His Ser Val
    1325                1330                1335

Met Val Tyr Trp Gly Asp Arg Lys Lys Tyr Gln Ala Leu Leu Asn
    1340                1345                1350

Arg Met Gly Leu Pro Glu Asp Trp Val Glu Gln Ile Asp Glu Asn
    1355                1360                1365

Pro Gly Val Leu Tyr Arg Arg Ala Ala Asn Lys Lys Glu Leu Leu
    1370                1375                1380

Leu Lys Leu Ala Glu Lys Val His Ser Pro Gly Val Thr Ser Ser
    1385                1390                1395

Leu Ser Lys Gly His Val Val Pro Arg Val Val Ala Ala Gly Val
    1400                1405                1410

Tyr Leu Leu Ser Arg His Cys Phe Arg Phe Ser Ser Ser Ile His
    1415                1420                1425

Gly Arg Gly Ser Ala Gln Lys Ala Ser Leu Ile Lys Leu Leu Met
    1430                1435                1440

Met Ser Ser Ile Ser Ala Met Lys His Gly Gly Ser Leu Asn Pro
    1445                1450                1455

Asn Gln Glu Arg Met Leu Phe Pro Gln Ala Gln Glu Tyr Asp Arg
    1460                1465                1470

Val Cys Thr Leu Leu Glu Glu Val Glu His Leu Thr Gly Lys Phe
    1475                1480                1485

Val Val Arg Glu Arg Asn Ile Val Arg Ser Arg Ile Asp Leu Phe
    1490                1495                1500

Gln Glu Pro Val Asp Leu Arg Cys Lys Ala Glu Asp Leu Val Ser
    1505                1510                1515

Glu Val Trp Phe Gly Leu Lys Arg Thr Lys Leu Gly Pro Arg Leu
    1520                1525                1530

Leu Lys Glu Glu Trp Asp Lys Leu Arg Ala Ser Phe Ala Trp Leu
    1535                1540                1545

Ser Thr Asp Pro Ser Glu Thr Leu Arg Asp Gly Pro Phe Leu Ser
    1550                1555                1560

His Val Gln Phe Arg Asn Phe Ile Ala His Val Asp Ala Lys Ser
    1565                1570                1575

Arg Ser Val Arg Leu Leu Gly Ala Pro Val Lys Lys Ser Gly Gly
    1580                1585                1590

Val Thr Thr Ile Ser Gln Val Arg Met Asn Phe Phe Pro Gly
    1595                1600                1605

Phe Ser Leu Glu Ala Glu Lys Ser Leu Asp Asn Gln Glu Arg Leu
    1610                1615                1620

Glu Ser Ile Ser Ile Leu Lys His Val Leu Phe Met Val Leu Asn
    1625                1630                1635

Gly Pro Tyr Thr Glu Glu Tyr Lys Leu Asp Met Ile Ile Glu Ala
```

```
              1640                1645                1650

Phe Ser Thr Leu Val Ile Pro Gln Pro Ser Glu Val Ile Arg Lys
        1655                1660                1665

Ser Arg Thr Met Thr Leu Cys Leu Leu Ser Asn Tyr Leu Ser Ser
        1670                1675                1680

Arg Gly Gly Ser Ile Leu Asp Gln Ile Glu Arg Ala Gln Ser Gly
        1685                1690                1695

Thr Leu Gly Gly Phe Ser Lys Pro Gln Lys Thr Phe Ile Arg Pro
        1700                1705                1710

Gly Gly Gly Ile Gly Tyr Lys Gly Lys Gly Val Trp Thr Gly Val
        1715                1720                1725

Met Glu Asp Thr His Val Gln Ile Leu Ile Asp Gly Asp Gly Thr
        1730                1735                1740

Ser Asn Trp Leu Glu Glu Ile Arg Leu Ser Ser Asp Ala Arg Leu
        1745                1750                1755

Tyr Asp Val Ile Glu Ser Ile Arg Arg Leu Cys Asp Asp Leu Gly
        1760                1765                1770

Ile Asn Asn Arg Val Ala Ser Ala Tyr Arg Gly His Cys Met Val
        1775                1780                1785

Arg Leu Ser Gly Phe Lys Ile Lys Pro Ala Ser Arg Thr Asp Gly
        1790                1795                1800

Cys Pro Val Arg Ile Met Glu Arg Gly Phe Arg Ile Arg Glu Leu
        1805                1810                1815

Gln Asn Pro Asp Glu Val Lys Met Arg Val Arg Gly Asp Ile Leu
        1820                1825                1830

Asn Leu Ser Val Thr Ile Gln Glu Gly Arg Val Met Asn Ile Leu
        1835                1840                1845

Ser Tyr Arg Pro Arg Asp Thr Asp Ile Ser Glu Ser Ala Ala Ala
        1850                1855                1860

Tyr Leu Trp Ser Asn Arg Asp Leu Phe Ser Phe Gly Lys Lys Glu
        1865                1870                1875

Pro Ser Cys Ser Trp Ile Cys Leu Lys Thr Leu Asp Asn Trp Ala
        1880                1885                1890

Trp Ser His Ala Ser Val Leu Leu Ala Asn Asp Arg Lys Thr Gln
        1895                1900                1905

Gly Ile Asp Asn Arg Ala Met Gly Asn Ile Phe Arg Asp Cys Leu
        1910                1915                1920

Glu Gly Ser Leu Arg Lys Gln Gly Leu Met Arg Ser Lys Leu Thr
        1925                1930                1935

Glu Met Val Glu Lys Asn Val Val Pro Leu Thr Thr Gln Glu Leu
        1940                1945                1950

Val Asp Ile Leu Glu Glu Asp Ile Asp Phe Ser Asp Val Ile Ala
        1955                1960                1965

Val Glu Leu Ser Glu Gly Ser Leu Asp Ile Glu Ser Ile Phe Asp
        1970                1975                1980

Gly Ala Pro Ile Leu Trp Ser Ala Glu Val Glu Glu Phe Gly Glu
        1985                1990                1995

Gly Val Val Ala Val Ser Tyr Ser Ser Lys Tyr Tyr His Leu Thr
        2000                2005                2010

Leu Met Asp Gln Ala Ala Ile Thr Met Cys Ala Ile Met Gly Lys
        2015                2020                2025

Glu Gly Cys Arg Gly Leu Leu Thr Glu Lys Arg Cys Met Ala Ala
        2030                2035                2040
```

Ile Arg Glu Gln Val Arg Pro Phe Leu Ile Phe Leu Gln Ile Pro
    2045                2050                2055

Glu Asp Ser Ile Ser Trp Val Ser Asp Gln Phe Cys Asp Ser Arg
    2060                2065                2070

Gly Leu Asp Glu Glu Ser Thr Ile Met Trp Gly
    2075                2080

<210> SEQ ID NO 22
<211> LENGTH: 1073
<212> TYPE: PRT
<213> ORGANISM: Unknown
<220> FEATURE:
<223> OTHER INFORMATION: severe fever thrombocytopenia syndrome virus
      B-3 M

<400> SEQUENCE: 22

Met Met Lys Val Ile Trp Phe Ser Ser Leu Ile Cys Leu Val Ile Gln
1               5                   10                  15

Cys Ser Gly Asp Thr Gly Pro Ile Ile Cys Ala Gly Pro Ile His Ser
            20                  25                  30

Asn Lys Ser Ala Asn Ile Pro His Leu Leu Gly Tyr Ser Glu Lys Ile
        35                  40                  45

Cys Gln Ile Asp Arg Leu Ile His Val Ser Ser Trp Leu Arg Asn His
    50                  55                  60

Ser Gln Phe Gln Gly Tyr Val Gly Gln Arg Gly Arg Ser Gln Val
65                  70                  75                  80

Ser Tyr Tyr Pro Ala Glu Asn Ser Tyr Ser Arg Trp Ser Gly Leu Leu
                85                  90                  95

Ser Pro Cys Asp Ala Asp Trp Leu Gly Met Leu Val Val Lys Lys Ala
            100                 105                 110

Lys Gly Ser Asp Met Ile Val Pro Gly Pro Ser Tyr Lys Gly Lys Val
        115                 120                 125

Phe Phe Glu Arg Pro Thr Phe Asp Gly Tyr Val Gly Trp Gly Cys Gly
    130                 135                 140

Ser Gly Lys Ser Arg Thr Glu Ser Gly Glu Leu Cys Ser Ser Asp Ser
145                 150                 155                 160

Gly Thr Ser Ser Gly Leu Leu Pro Ser Asn Arg Val Leu Trp Ile Gly
                165                 170                 175

Asp Val Ala Cys Gln Pro Met Thr Pro Ile Pro Glu Glu Thr Phe Leu
            180                 185                 190

Glu Leu Lys Ser Phe Ser Gln Ser Glu Phe Pro Asp Ile Cys Lys Val
        195                 200                 205

Asp Gly Ile Val Phe Asn Gln Cys Glu Ser Glu Ser Leu Pro Gln Pro
    210                 215                 220

Phe Asp Val Ala Trp Met Asp Val Gly His Ser His Lys Ile Ile Met
225                 230                 235                 240

Arg Glu His Lys Thr Lys Trp Val Gln Glu Ser Ser Lys Asp Phe
                245                 250                 255

Val Cys Tyr Lys Glu Gly Thr Gly Pro Cys Ser Glu Ser Glu Lys
            260                 265                 270

Thr Cys Lys Thr Ser Gly Ser Cys Arg Gly Asp Met Gln Phe Cys Lys
        275                 280                 285

Val Ala Gly Cys Glu His Gly Glu Glu Ala Ser Glu Ala Lys Cys Arg
    290                 295                 300

Cys Ser Leu Val His Lys Pro Gly Glu Val Val Val Ser Tyr Gly Gly

```
305                 310                 315                 320
Met Arg Val Arg Pro Lys Cys Tyr Gly Phe Ser Arg Met Met Ala Thr
                325                 330                 335
Leu Glu Val Asn Pro Glu Gln Arg Ile Gly Gln Cys Thr Gly Cys
                340                 345                 350
His Leu Glu Cys Ile Asn Gly Val Arg Leu Ile Thr Leu Thr Ser
                355                 360                 365
Glu Leu Lys Ser Ala Thr Val Cys Ala Ser His Phe Cys Ser Ser Ala
370                 375                 380
Thr Ser Gly Lys Lys Ser Thr Glu Ile Gln Phe His Ser Gly Ser Leu
385                 390                 395                 400
Val Gly Lys Ala Ala Ile His Val Lys Gly Thr Leu Val Asp Gly Thr
                405                 410                 415
Glu Phe Thr Phe Glu Gly Ser Cys Met Phe Pro Asp Gly Cys Asp Ala
                420                 425                 430
Val Asp Cys Thr Phe Cys Arg Glu Phe Leu Lys Asn Pro Gln Cys Tyr
                435                 440                 445
Pro Ala Lys Lys Trp Leu Phe Ile Ile Ala Ile Leu Leu Gly Tyr
                450                 455                 460
Ala Gly Leu Met Leu Leu Thr Asn Val Leu Lys Ala Ile Gly Val Trp
465                 470                 475                 480
Gly Ser Trp Val Ile Ala Pro Val Lys Leu Met Phe Ala Ile Ile Lys
                485                 490                 495
Lys Leu Met Arg Ser Val Ser Cys Leu Met Gly Lys Leu Met Asp Arg
                500                 505                 510
Gly Arg Gln Val Ile His Glu Ile Gly Glu Asn Arg Glu Gly Asn
                515                 520                 525
Gln Glu Asp Val Arg Ile Glu Ile Ala Arg Pro Arg Val Arg His
                530                 535                 540
Trp Met Tyr Ser Pro Val Ile Leu Ala Ile Leu Ala Ile Gly Leu Ala
545                 550                 555                 560
Glu Gly Cys Asp Glu Met Val His Ala Asp Ser Lys Leu Val Ser Cys
                565                 570                 575
Arg Gln Gly Ser Gly Asn Met Lys Glu Cys Val Thr Thr Gly Arg Ala
                580                 585                 590
Leu Leu Pro Ala Val Asn Pro Gly Gln Glu Ala Cys Leu His Phe Thr
                595                 600                 605
Ala Pro Gly Ser Pro Asp Ser Lys Cys Leu Lys Ile Lys Val Lys Arg
                610                 615                 620
Ile Asn Leu Lys Cys Lys Lys Ser Ser Ser Tyr Phe Val Pro Asp Ala
625                 630                 635                 640
Arg Ser Arg Cys Thr Ser Val Arg Arg Cys Arg Trp Ala Gly Asp Cys
                645                 650                 655
Gln Ser Gly Cys Pro Ser His Phe Thr Ser Asn Ser Phe Ser Asp Asp
                660                 665                 670
Trp Ala Gly Lys Met Asp Arg Ala Gly Leu Gly Phe Ser Gly Cys Ser
                675                 680                 685
Asp Gly Cys Gly Gly Ala Ala Cys Gly Cys Phe Asn Ala Ala Pro Ser
                690                 695                 700
Cys Ile Phe Trp Arg Lys Trp Val Glu Asn Pro His Gly Ile Ile Trp
705                 710                 715                 720
Lys Val Ser Pro Cys Ala Ala Trp Val Pro Ser Thr Val Ile Glu Leu
                725                 730                 735
```

Thr Met Pro Ser Gly Glu Val Arg Thr Phe His Pro Met Ser Gly Ile
            740                 745                 750

Pro Thr Gln Val Phe Lys Gly Val Ser Val Thr Tyr Leu Gly Ser Asp
            755                 760                 765

Met Glu Val Ser Gly Leu Thr Asp Leu Cys Glu Ile Glu Glu Leu Lys
770                 775                 780

Ser Lys Lys Leu Ala Leu Ala Pro Cys Asn Gln Ala Gly Met Gly Val
785                 790                 795                 800

Val Gly Lys Val Gly Glu Ile Gln Cys Ser Ser Glu Ser Ala Arg
                805                 810                 815

Ser Ile Lys Lys Asp Gly Cys Ile Trp Asn Ala Asp Leu Val Gly Ile
            820                 825                 830

Glu Leu Arg Val Asp Asp Ala Val Cys Tyr Ser Lys Ile Thr Ser Val
            835                 840                 845

Glu Ala Val Ala Asn Tyr Ser Ala Ile Pro Thr Thr Ile Gly Gly Leu
850                 855                 860

Arg Phe Glu Arg Ser His Asp Ser Gln Gly Lys Ile Ser Gly Ser Pro
865                 870                 875                 880

Leu Asp Ile Thr Ala Ile Arg Gly Ser Phe Ser Val Asn Tyr Arg Gly
            885                 890                 895

Leu Arg Leu Ser Leu Ser Glu Ile Thr Ala Thr Cys Thr Gly Glu Val
            900                 905                 910

Thr Asn Val Ser Gly Cys Tyr Ser Cys Met Thr Gly Ala Lys Val Ser
            915                 920                 925

Ile Lys Leu His Ser Ser Lys Asn Ser Thr Ala His Val Arg Cys Lys
930                 935                 940

Gly Asp Glu Thr Ala Phe Ser Val Leu Glu Gly Val His Ser Tyr Thr
945                 950                 955                 960

Val Ser Leu Ser Phe Asp His Ala Val Val Asp Glu Gln Cys Gln Leu
            965                 970                 975

Asn Cys Gly Gly His Glu Ser Gln Val Thr Leu Lys Gly Asn Leu Ile
            980                 985                 990

Phe Leu Asp Val Pro Lys Phe Val Asp Gly Ser Tyr Met Gln Thr Tyr
            995                 1000                1005

His Ser Ser Val Pro Thr Gly Ala Asn Ile Pro Ser Pro Thr Asp
            1010                1015                1020

Trp Leu Asn Ala Leu Phe Gly Asn Gly Leu Ser Arg Trp Ile Leu
            1025                1030                1035

Gly Val Ile Gly Val Leu Leu Gly Gly Leu Ala Leu Phe Phe Leu
            1040                1045                1050

Ile Met Ser Leu Phe Lys Leu Gly Thr Lys Gln Ile Phe Arg Ser
            1055                1060                1065

Arg Thr Lys Leu Ala
            1070

<210> SEQ ID NO 23
<211> LENGTH: 245
<212> TYPE: PRT
<213> ORGANISM: Unknown
<220> FEATURE:
<223> OTHER INFORMATION: severe fever thrombocytopenia syndrome virus
      B-3 NP

<400> SEQUENCE: 23

Met Ser Glu Trp Ser Arg Ile Ala Val Glu Phe Gly Glu Gln Gln Leu

```
                 1               5              10              15
              Asn Leu Thr Glu Leu Glu Asp Phe Ala Arg Glu Leu Ala Tyr Glu Gly
                             20                  25                  30

Leu Asp Pro Ala Leu Ile Ile Lys Lys Leu Lys Glu Thr Gly Gly Asp
                             35                  40                  45

Asp Trp Val Arg Asp Thr Lys Phe Ile Ile Val Phe Ala Leu Thr Arg
                             50                  55                  60

Gly Asn Lys Ile Val Lys Ala Ser Gly Lys Met Ser Asn Ser Gly Ser
               65                 70                  75                  80

Lys Arg Leu Met Ala Leu Gln Glu Lys Tyr Gly Leu Val Glu Arg Ala
                                 85                  90                  95

Glu Thr Arg Leu Ser Ile Thr Pro Val Arg Val Ala Gln Ser Leu Pro
                            100                 105                 110

Thr Trp Thr Cys Ala Ala Ala Ala Leu Lys Glu Tyr Leu Pro Val
                            115                 120                 125

Gly Pro Ala Val Met Asn Leu Lys Val Glu Asn Tyr Pro Pro Glu Met
                            130                 135                 140

Met Cys Met Ala Phe Gly Ser Leu Ile Pro Thr Ala Gly Val Ser Glu
              145                 150                 155                 160

Ala Thr Thr Lys Thr Leu Met Glu Ala Tyr Ser Leu Trp Gln Asp Ala
                                165                 170                 175

Phe Thr Lys Thr Ile Asn Val Lys Met Arg Gly Ala Ser Lys Thr Glu
                            180                 185                 190

Val Tyr Asn Ser Phe Arg Asp Pro Leu His Ala Ala Val Asn Ser Val
                            195                 200                 205

Phe Phe Pro Asn Asp Val Arg Val Lys Trp Leu Lys Ala Lys Gly Ile
                            210                 215                 220

Leu Gly Pro Asp Gly Val Pro Ser Arg Ala Ala Glu Val Ala Ala Ala
              225                 230                 235                 240

Ala Tyr Arg Asn Leu
                            245

<210> SEQ ID NO 24
<211> LENGTH: 293
<212> TYPE: PRT
<213> ORGANISM: Unknown
<220> FEATURE:
<223> OTHER INFORMATION: severe fever thrombocytopenia syndrome virus
      B-3 NS

<400> SEQUENCE: 24

Met Ser Leu Ser Lys Cys Ser Asn Val Asp Leu Lys Ser Val Ala Met
               1               5                  10                  15

Asn Ala Asn Thr Val Arg Leu Glu Pro Ser Leu Gly Glu Tyr Pro Thr
                             20                  25                  30

Leu Arg Lys Asp Leu Val Glu Cys Ser Cys Ser Val Leu Thr Leu Ser
                             35                  40                  45

Met Val Lys Arg Met Gly Lys Met Thr Asn Thr Val Trp Leu Phe Gly
                             50                  55                  60

Asn Pro Lys Asn Pro Leu His Gln Leu Glu Pro Gly Leu Glu Gln Leu
               65                 70                  75                  80

Leu Asp Met Tyr Tyr Lys Asp Met Arg Cys Tyr Ser Gln Arg Glu Leu
                                 85                  90                  95

Ser Ala Leu Arg Trp Pro Ser Gly Lys Pro Ser Val Trp Phe Leu Gln
                            100                 105                 110
```

-continued

```
Ala Ala His Met Phe Phe Ser Ile Lys Asn Ser Trp Ala Met Glu Thr
        115                 120                 125

Gly Arg Glu Asn Trp Arg Gly Leu Phe His Arg Ile Thr Lys Gly Lys
    130                 135                 140

Lys Tyr Leu Phe Glu Gly Asp Met Ile Leu Asp Ser Leu Glu Ala Ile
145                 150                 155                 160

Glu Lys Arg Arg Leu Arg Leu Gly Leu Pro Glu Ile Leu Ile Thr Gly
                165                 170                 175

Leu Ser Pro Ile Leu Asp Val Ala Leu Leu Gln Ile Glu Ser Leu Ala
            180                 185                 190

Arg Leu Arg Gly Met Ser Leu Asn His His Leu Phe Thr Ser Ser Ser
        195                 200                 205

Leu Arg Lys Pro Leu Leu Asp Cys Trp Asp Phe Phe Ile Pro Ile Arg
    210                 215                 220

Lys Lys Lys Thr Asp Gly Ser Tyr Ser Val Leu Asp Glu Asp Asp Glu
225                 230                 235                 240

Pro Gly Val Leu Gln Gly Tyr Pro Tyr Leu Met Ala His Tyr Leu Asn
                245                 250                 255

Arg Cys Pro Phe His Asn Leu Ile Arg Phe Asp Glu Glu Leu Arg Thr
            260                 265                 270

Ala Ala Leu Asn Thr Ile Trp Gly Arg Asp Trp Pro Ala Ile Gly Asp
        275                 280                 285

Leu Pro Lys Glu Val
        290
```

SEVERE FEVER WITH THROMBOCYTOPENIA SYNDROME VIRUS

CROSS REFERENCE TO RELATED APPLICATIONS

This application is a National Stage of International Application No. PCT/KR2019/004857 filed Apr. 23, 2019, claiming priority based on Korean Patent Application No. 10-2018-0047865 filed Apr. 25, 2018, the entire disclosures of which are incorporated herein by reference.

TECHNICAL FIELD

The present disclosure relates to a novel genotype of severe fever with thrombocytopenia syndrome virus and use thereof as an immunogenic composition.

BACKGROUND ART

A severe fever with thrombocytopenia syndrome (SFTS) is accompanied by symptoms such as high fever, vomiting, diarrhea, thrombocytopenia, leukopenia and multiple organ failure, and is a serious disease with a mortality rate of 6% to 30% (Yu X J et al., N. Engl. J. Med. 2011; 364:1523-32; Ding F et al Clin Infect Dis 2013; 56: 1682-3).

A causative pathogen of SFTS is SFTSV (severe fever thrombocytopenia syndrome virus), which belongs to Bunyaviridae family. Bunyaviridae family is a negative-strand RNA virus containing three segments. Bunyaviridae family includes five genera including Orthobunyavirus, Hantavirus, Nairovirus, Phlebovirus and Tospovirus. SFTSV belongs to the Phlebovirus genus which includes Rift valley fever virus. SFTSV was first reported in China in 2011 (Yu X J et al. ibid), and is a new variant virus that continues to outbreak not only in China, but also in Korea and Japan. SFTSV is a ball-shaped virus with a diameter of 80 nm to 100 nm. This virus carries three genes: a large (L) segment as a single-stranded negative sense RNA segment, a medium (M) segment, and a small (S) segment (NP, NS).

The SFTS virus is known to spread via *Haemaphysalis longicornis* as a vector thereof, which spreads widely in Korea as well (Chae J S et al. J Vet Sci 2008; 9: 285-93; Kim C M et al. Appl Environ Microbiol 2006; 72: 5766-76). Seroconversion and viraemia of the SFTS virus have been found in domestic animals such as goats, sheep, cattle, pigs and dogs. It is believed that these animals act as intermediate vectors thereof in the area where SFTS virus spreads (Zhao L et al. Emerg Infect Dis 2013; 18: 963-5; Niu G et al. Emerg Infect Dis 2013; 19: 756-63). SFTSV is detected in the blood of patients, and the concentration of SFTSV is very high in blood of severely ill patients. Thus, human-to-human transmission thereof is possible via the blood (Tang X, Wu W, Wang H, et al. J Infect Dis 2013; 207:736-739.).

Antiviral agents for SFTSV have not been developed yet, and thus SFTS treatment is based on conservative therapy for organ failure such as blood transfusion and renal replacement therapy. In China, ribavirin infusion has been introduced into the treatment guidelines since 2012. However, there was no difference in the mortality rate between the ribavirin-treated group and the non-administered group in the recently published treatment results. Therefore, a vaccine against SFTSV is required, but such a vaccine has not been developed yet.

DISCLOSURE

Technical Purpose

A purpose of the present disclosure is to provide a novel genotype of severe fever with thrombocytopenia syndrome virus and an immunogenic composition containing the same.

Technical Solution

To achieve the purpose, the present disclosure provides a novel severe fever with thrombocytopenia syndrome virus.

Further, the present disclosure provides an immunogenic composition for prevention or treatment of the severe fever with thrombocytopenia syndrome.

Further, the present disclosure provides antibodies against the severe fever with thrombocytopenia syndrome virus or an antigen thereof.

Further, the present disclosure provides a diagnostic kit for the severe fever with thrombocytopenia syndrome virus.

Further, the present disclosure provides a method to detect the severe fever with thrombocytopenia syndrome virus antibody.

Further, the present disclosure provides a method for producing antiserum against the severe fever with thrombocytopenia syndrome virus.

In addition, the present disclosure provides a method to provide information regarding diagnosis of the severe fever with thrombocytopenia syndrome.

Advantageous Effects

The severe fever with thrombocytopenia syndrome virus according to the present disclosure is genetically different from the conventional thrombocytopenia virus and is a novel virus as systematically subdivided from a B genotype. Thus, the novel virus according to the present disclosure may be usefully used as vaccines with excellent cross immunogenicity against SFTSV, due to characteristics of a vaccine that only a specific genotype virus exhibits limited protective ability.

MODES OF THE INVENTION

Figure 1:
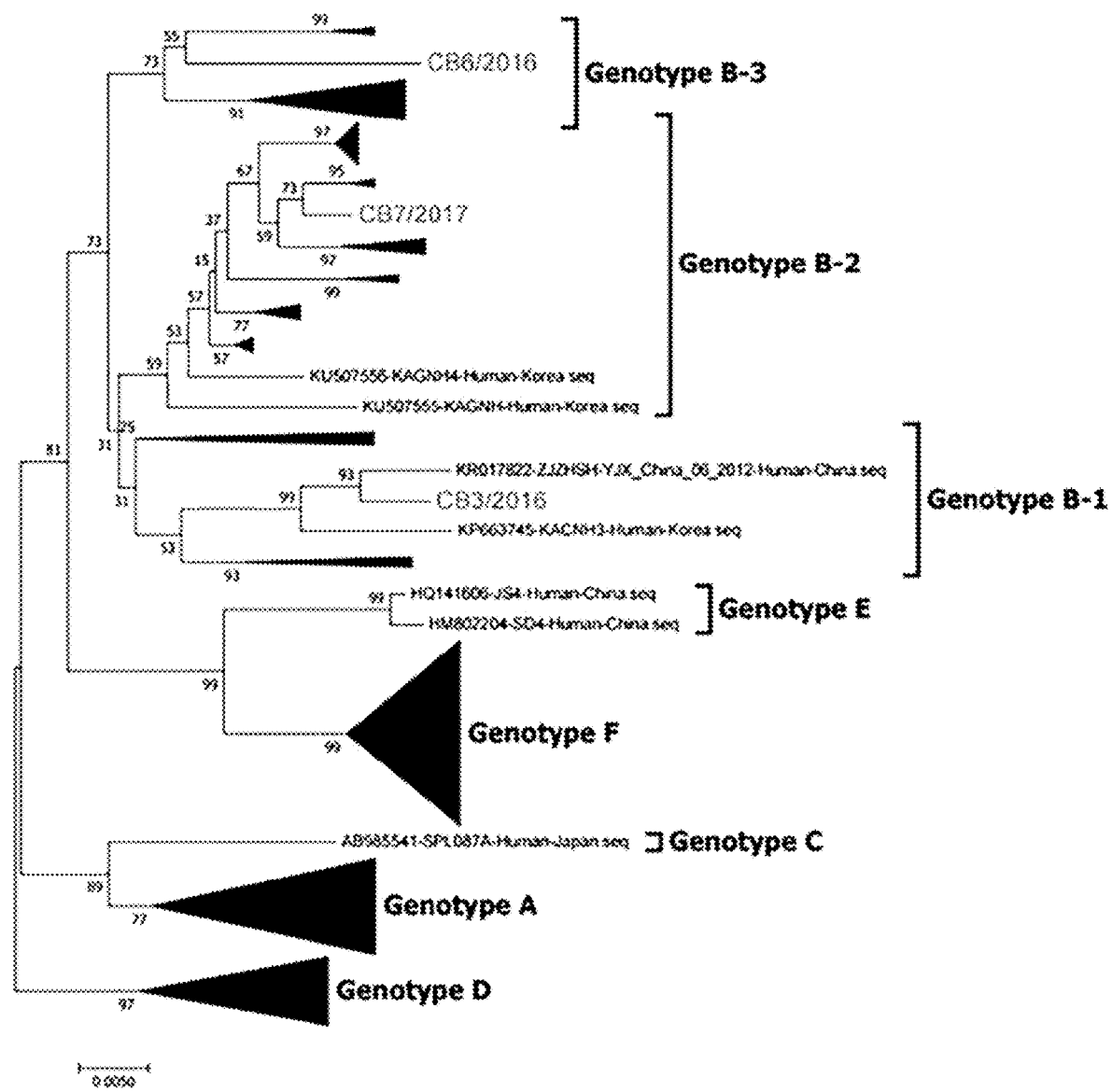
FIG. 1 is a phylogenetic tree showing three novel viruses according to the present disclosure and SFTSV L gene isolated from China, Japan, and Korea.
Figure 2:
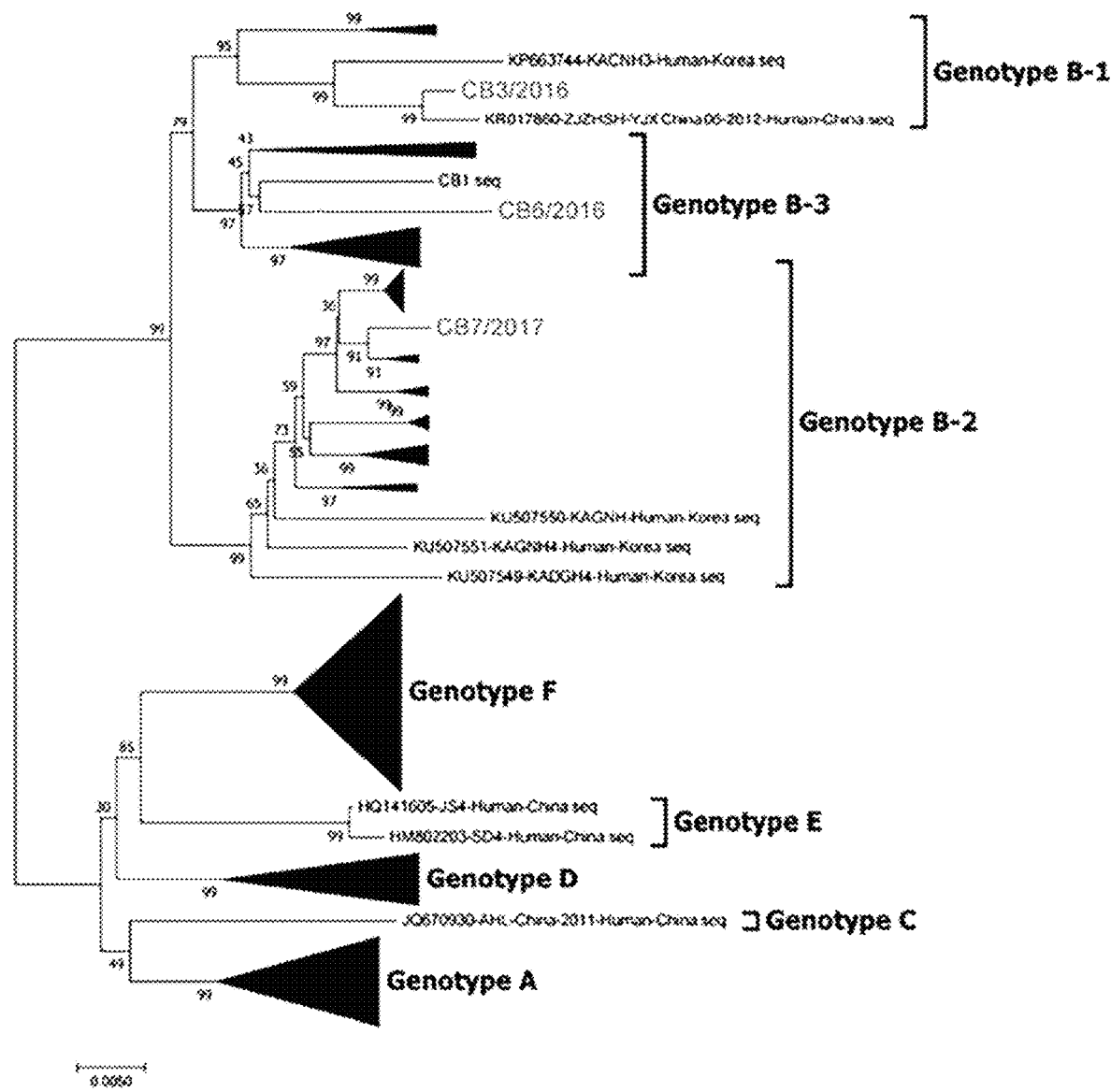
FIG. 2 is a phylogenetic tree showing the three novel viruses according to the present disclosure and SFTSV M gene isolated from China, Japan, and Korea.
Figure 3:
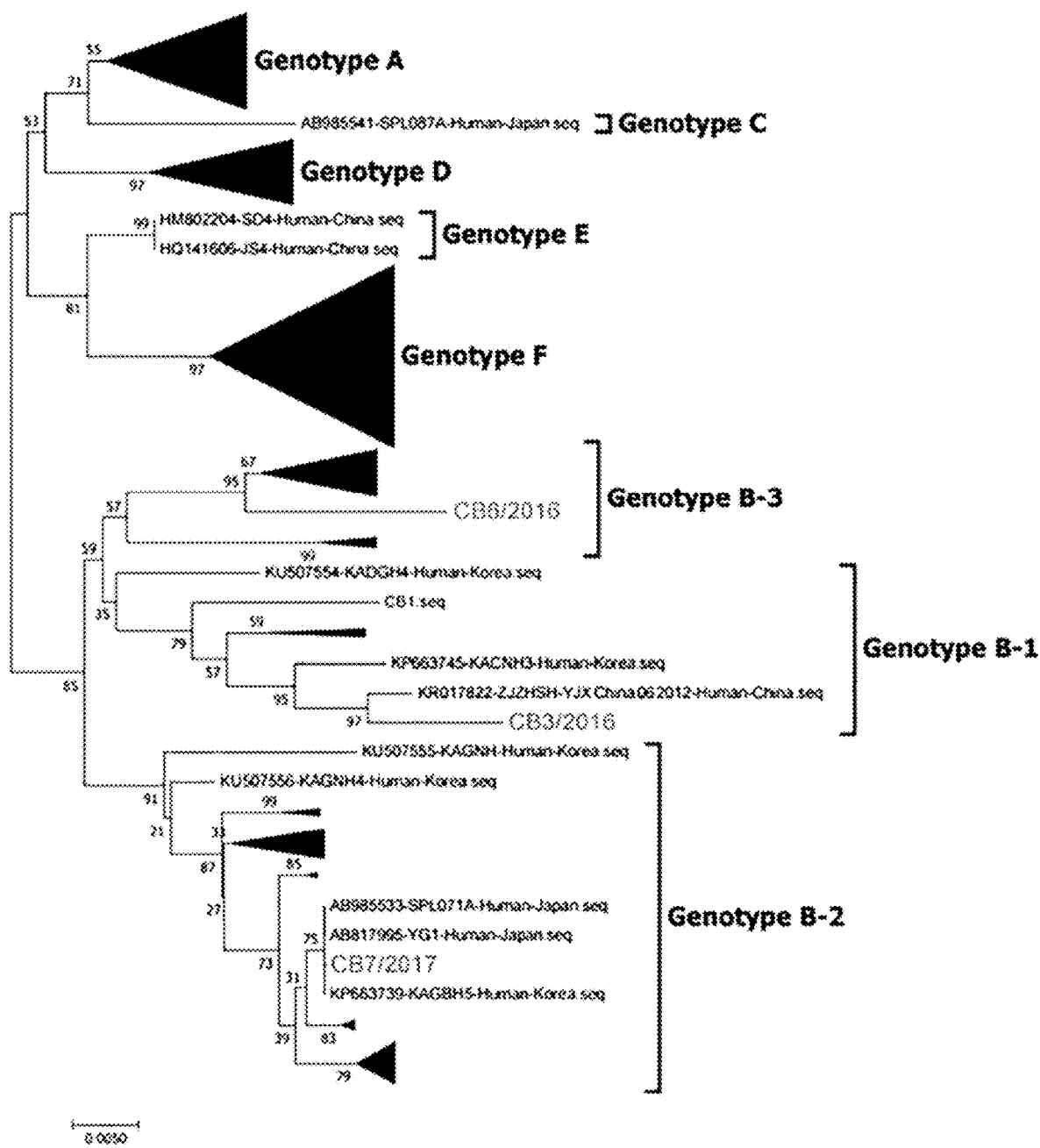
FIG. 3 is a phylogenetic tree showing the three novel viruses according to the present disclosure and SFTSV S (NP) gene isolated from China, Japan, and Korea.
Figure 4:
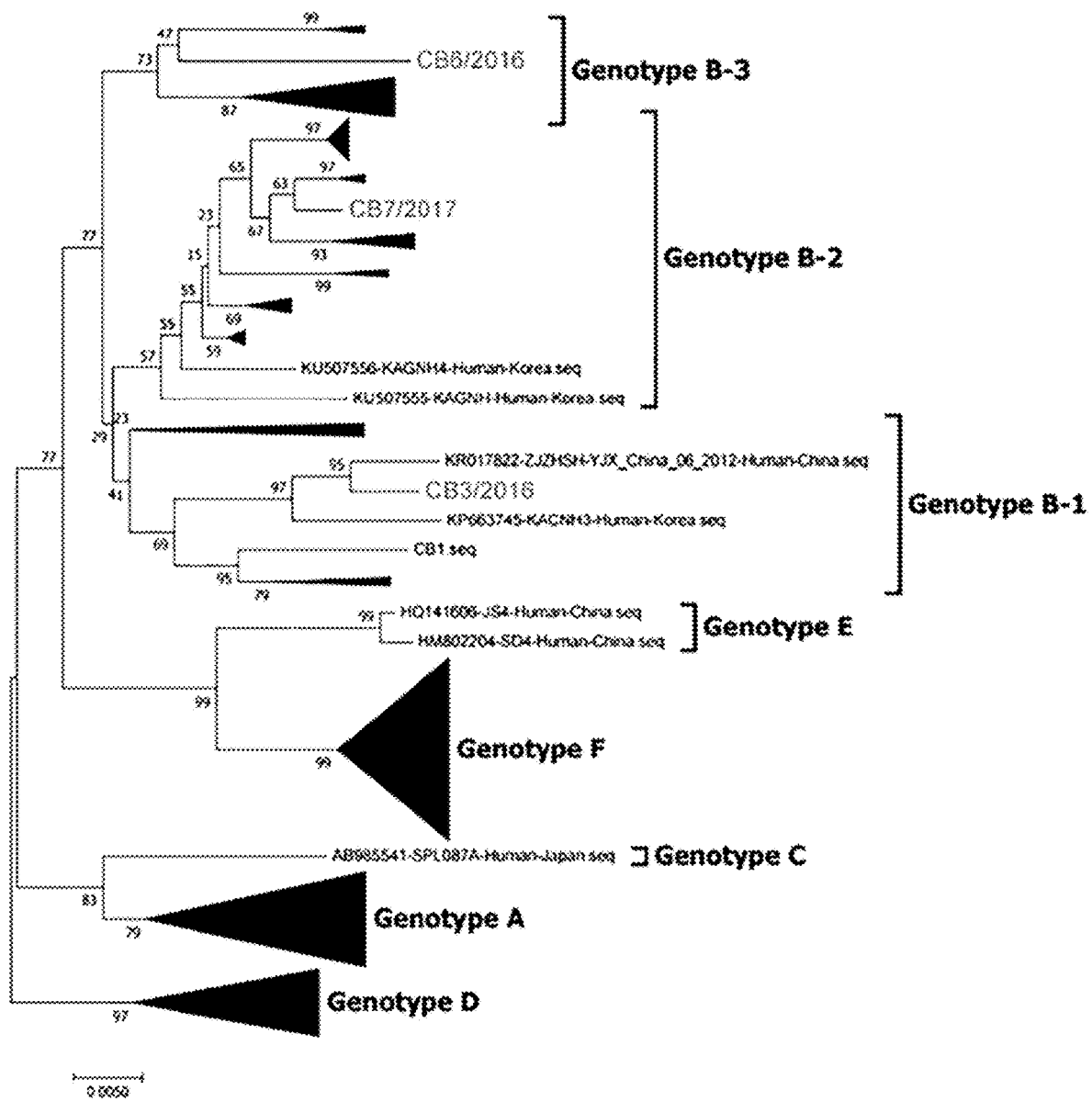
FIG. 4 is a phylogenetic tree showing the three novel viruses according to the present disclosure and SFTSV S (NS) gene isolated from China, Japan, and Korea.

Hereinafter, the present disclosure will be described in detail based on implementations according to the present disclosure with reference to the accompanying drawings. However, the following implementations are presented as only examples of the present disclosure. When it is determined that detailed description of a well-known component or configuration may unnecessarily obscure the gist of the present disclosure, the detailed description may be omitted. The implementations do not limit the present disclosure. The present disclosure may be variously modified and applied within the scope interpreted based on the claims to be described later.

Further, terms (terminologies) used in this specification are used to properly describe preferred Example of the present disclosure, and may vary according to a user's or operator's intention or a practice of the field to which the present disclosure belongs. Accordingly, definitions of these terms should be made based on contents throughout the present specification. It will be further understood that the terms "comprises", "comprising", "includes", and "including", "containing" and "contains", etc. when used in this specification, specify the presence of the stated elements, and/or components, but do not preclude the presence or addition of one or more other elements, components, and/or portions thereof.

In one aspect, the present disclosure relates to the severe fever with thrombocytopenia syndrome virus (SFTSV) in which a 1447-th amino acid of a protein expressed in ORF (6255 bp) of an L gene thereof is valine or a 1913-rd amino acid thereof is lysine, wherein a 83-rd amino acid of a protein expressed in ORF (3222 bp) of an M gene thereof is tyrosine, or a 404-th amino acid thereof is threonine or a 904-th amino acid thereof is valine. In one Example of the present disclosure, this virus was named B-1 (CB3).

In one implementation, the severe fever with thrombocytopenia syndrome virus belongs to genotype B-1 and may be a virus in which isoleucine as a 1447-th amino acid of a protein expressed in ORF (6255 bp) of an L gene of a virus conventionally classified as a genotype B is substituted with valine, and arginine as a 1913-rd amino acid thereof is substituted (SEQ ID NO: 13) with lysine, and isoleucine as a 904-th amino acid of an M gene thereof is substituted (SEQ ID NO: 14) with valine.

In one implementation, the severe fever with thrombocytopenia syndrome virus may contain an L gene containing a base sequence represented by SEQ ID NO: 1, an M gene containing a base sequence represented by SEQ ID NO: 2, and an S gene containing NP containing a base sequence represented by SEQ ID NO: 3 and NS containing a base sequence represented by SEQ ID NO: 4.

In one implementation, the severe fever with thrombocytopenia syndrome virus may contain an amino acid sequence represented by SEQ ID NO: 13 expressed in ORF (6255 bp) of an L gene, an amino acid sequence represented by SEQ ID NO: 14 expressed in ORF (3222 bp) of an M gene, and an amino acid sequence represented by SEQ ID NO: 15 expressed in ORF of an NP gene, and an amino acid sequence represented by SEQ ID NO: 16 expressed in ORF of an NS gene.

In one aspect, the present disclosure relates to a severe fever with thrombocytopenia syndrome virus in which a 1447-th amino acid of a protein expressed in ORF (6255 bp) of an L gene thereof is isoleucine or a 1913-rd amino acid thereof is arginine, wherein a 83-rd amino acid of a protein expressed in ORF (3222 bp) of an M gene is phenylalanine, a 404-th amino acid thereof is threonine or a 904-th amino acid thereof is isoleucine. In one Example of the present disclosure, the virus was named B-2 (CB4).

In one implementation, the severe fever with thrombocytopenia syndrome virus belongs to genotype B-2, and may be a virus in which tyrosine as an 83-rd amino acid of an M gene of a virus conventionally classified as a genotype B has been replaced with phenylalanine.

In one implementation, the severe fever with thrombocytopenia syndrome virus may contain an L gene containing a base sequence represented by SEQ ID NO: 5, an M gene containing a base sequence represented by SEQ ID NO: 6, and an S gene containing a NP containing a base sequence represented by SEQ ID NO: 7 and a NS containing a base sequence represented by SEQ ID NO: 8.

In one implementation, the severe fever with thrombocytopenia syndrome virus may contain an amino acid sequence represented by SEQ ID NO: 17 expressed in ORF of an L gene, an amino acid sequence represented by SEQ ID NO: 18 expressed in ORF of an M gene, an amino acid sequence represented by SEQ ID NO: 19 expressed in ORF of an NP gene and an amino acid sequence represented by SEQ ID NO: 20 expressed in ORF of an NS gene.

In one aspect, the present disclosure relates to a severe fever with thrombocytopenia syndrome virus in which a 1447-th amino acid of a protein expressed in ORF (6255 bp) of an L gene thereof is isoleucine or a 1913-rd amino acid thereof is arginine, wherein a 83-rd amino acid of a protein expressed in ORF (3222 bp) of an M gene thereof is tyrosine, a 404-th amino acid thereof is alanine or a 904-th amino acid thereof is isoleucine. In one Example of the present disclosure, the virus was named B-3 (CB1).

In one implementation, the severe fever with thrombocytopenia syndrome virus belongs to genotype B-3, and may be a virus in which threonine as a 404-th amino acid of an M gene of a virus conventionally classified as a genotype B is substituted with alanine.

In one implementation, the severe fever with thrombocytopenia syndrome virus may contain an L gene containing a base sequence represented by SEQ ID NO: 9, an M gene containing a base sequence represented by SEQ ID NO: 10, and an S gene containing NP containing a base sequence represented by SEQ ID NO: 11 and NS containing a base sequence represented by SEQ ID NO: 12.

In one implementation, the severe fever with thrombocytopenia syndrome virus may contain an amino acid sequence represented by SEQ ID NO: 21 expressed in ORF of an L gene, an amino acid sequence represented by SEQ ID NO: 22 expressed in ORF of an M gene, an amino acid sequence represented by SEQ ID NO: 23 expressed in ORF of an NP gene, and an amino acid sequence represented by SEQ ID NO: 24 expressed in ORF of an NS gene.

In one example of the present disclosure, it was revealed based on a result of genetic analysis of the severe fever with thrombocytopenia syndrome virus as isolated that a gene sequence thereof was different from that of the severe fever with thrombocytopenia syndrome virus as previously known. It was revealed based on a result of systematically classifying the severe fever with thrombocytopenia syndrome virus according to the present disclosure that a genotype thereof is subdivided into at least three genotypes other than a single B genotype group as previously known.

The term "substitution" as used in the present disclosure refers to replacement of one or more amino acids or nucleotides by other amino acids or nucleotides, respectively.

The severe fever with thrombocytopenia syndrome virus according to the present disclosure is a negative single-stranded RNA virus and belongs to Bunyaviridae family and to phlebovirus genus. The severe fever with thrombocytopenia syndrome virus according to the present disclosure is a spherical virus with a diameter of 80 nm to 100 nm and spreads via *Haemaphysalis longicornis* as a vector thereof. A genome thereof includes a large (L) segment, a medium (M) segment, and a small (S) segment and codes six proteins including RNA dependent RNA polymerase (RdRp), glycoprotein precursor (M), glycoprotein N (Gn), glycoprotein C (Gc), nucleocapsid protein (NP), and non-structural protein (NS). In a negative or antisense strand (sense encoding a viral protein or antisense against a positive strand), a protein or gene is encoded as antisense. For expression of a gene into a protein, a sense or positive strand RNA is generated, and then translation therefrom is performed such that the protein is produced.

In one aspect, the present disclosure relates to an immunogenic composition for prevention or treatment of a severe fever with thrombocytopenia syndrome, the composition containing the severe fever with thrombocytopenia syndrome virus or an antigen thereof as an active ingredient.

In one implementation, the immunogenic composition according to the present disclosure may contain an inactivated severe fever with thrombocytopenia syndrome virus and a pharmaceutically acceptable carrier or adjuvant.

In one implementation, the immunogenic composition may be a vaccine composition, wherein a form thereof may be selected from the group consisting of live vaccine, killed vaccine, subunit vaccine produced using a gene of an attenuated severe fever with thrombocytopenia syndrome virus, vector vaccine, chimeric vaccine, DNA vaccine, and RNA vaccine.

In one implementation, the immunogenic composition may contain, as an active ingredient, a severe fever with thrombocytopenia syndrome virus containing an L gene containing a base sequence represented by SEQ ID NO: 1, an M gene containing a base sequence represented by SEQ ID NO: 2, and an S gene containing a base sequence represented by SEQ ID NO: 3; a severe fever with thrombocytopenia syndrome virus containing an L gene containing a base sequence represented by SEQ ID NO: 4, an M gene containing a base sequence represented by SEQ ID NO: 5, and an S gene containing a base sequence represented by SEQ ID NO: 6; and a severe fever with thrombocytopenia syndrome virus containing an L gene containing a base sequence represented by SEQ ID NO: 7, an M gene containing a base sequence represented by SEQ ID NO: 8, and an S gene containing a base sequence represented by SEQ ID NO: 9; or antigens thereof.

For preparation of the immunogenic composition (i.e., a vaccine) according to the present disclosure, the virus or an antigen thereof according to the present disclosure is transformed into a physiologically acceptable form. This may be done based on experiences of preparing a vaccine used for vaccination against influenza (disclosed by Stickl, H. et al. [1974] Dtsch. med. Wschr. 99, 2386-2392). For the preparation of vaccine injections, for example, virus particles are lyophilized in 100 ml of phosphate-buffered saline (PBS) under the presence of 1% human albumin and 2% peptone in ampoules, preferably in glass ampoules. Alternatively, vaccine injections may be produced by sequential freeze-drying of the virus in the formulation. This formulation may contain additional additives such as mannitol, dextran, sugar, glycine, lactose or polyvinylpyrrolidone or antioxidants or inert gases, stabilizers or other adjuvants such as recombinant proteins suitable for in vivo administration (e.g. human serum albumin). The glass ampoule may then be sealed and stored at a temperature between 4° C. and room temperature for several months. However, unless otherwise required, the ampoules may preferably be stored below −20° C.

For vaccination or treatment, the lyophilisate may be dissolved in 0.1 ml to 0.5 ml of an aqueous solution, preferably physiological saline or tris buffer, and then may be administered to a subject systemically or locally, i.e. in parenteral, subcutaneous, intramuscular manner or via other routes of administration known to those skilled in the art. A dosage form, dosage and frequency of administration thereof may be optimized by a person skilled in the art in a known manner. However, most commonly, patients receive a second vaccination about a month to 6 weeks after a first vaccination.

In the present disclosure, the term "prevention" refers to any action that inhibits or delays the occurrence, spread and recurrence of the severe fever with thrombocytopenia syndrome by administration of the immunogenic composition according to the present disclosure.

The term "treatment" as used in the present disclosure refers to any action that reduces or beneficially alters the symptoms of the severe fever with thrombocytopenia syndrome and complications thereof via the administration of the immunogenic composition according to the present disclosure. A person with ordinary knowledge in the technical field to which the present disclosure belongs refers to the data presented by the Korean Medical Association, etc. to know the exact criteria about the disease to which the composition according to the present disclosure is effective, and to determine degrees of the improvement and treatment.

The term "therapeutically effective amount" used in combination with an active ingredient in the present disclosure refers to an amount effective for preventing or treating the severe fever with thrombocytopenia syndrome. The therapeutically effective amount of the composition according to the present disclosure may vary depending on several factors, such as administration method, target site, and patient's condition. Therefore, when the composition is used for the human body, the dosage should be determined as an appropriate amount in consideration of safety and efficiency. The skilled person may estimate the amount to be used for humans from an effective amount determined through animal experiments. Factors to consider when determining the effective amount are described, for example, in Hardman and Limbird, eds., Goodman and Gilman's The Pharmacological Basis of Therapeutics, 10th ed. (2001), Pergamon Press; And E. W. Martin ed., Remington's Pharmaceutical Sciences, 18th ed. (1990), Mack Publishing Co.

A pharmaceutical composition according to the present disclosure is administered in a pharmaceutically effective amount. As used in the present disclosure, the term "pharmaceutically effective amount" refers to an amount sufficient to treat the severe fever with thrombocytopenia syndrome at a reasonable benefit/risk ratio applicable to medical treatment and not to cause side effects. The effective dose level may be determined based on factors including the patient's health status, type of transplantation, severity, activity of the drug, sensitivity to the drug, method of administration, time of administration, route of administration and rate of excretion, duration of treatment, drugs used in combination or simultaneously, and other factors well known in the medical field. The composition according to the present disclosure may be administered as an individual therapeutic agent or administered in combination with other therapeutic agents or may be administered sequentially or simultaneously with a conventional treatment agent, or may be administered single or multiple times. Considering all of the above factors, it is important to administer the amount by which the maximum effect may be obtained at the minimum amount without side effects. This amount may be easily determined by a person skilled in the art.

The pharmaceutical composition according to the present disclosure may contain carriers, diluents, excipients or a combination of two or more thereof commonly used in biological preparations. As used in the present disclosure, the term "pharmaceutically acceptable" refers to characteristics that a composition is not toxic to cells or humans as exposed to the composition. The carrier is not particularly limited as long as the carrier is suitable for delivery of the composition to a target site in vivo. The carrier may include, for example, compounds described in Merck Index, 13th ed., Merck & Co. Inc., saline, sterile water, Ringer's solution, buffered saline, dextrose solution, maltodextrin solution, glycerol, ethanol, and mixtures of one or more of these components. If necessary, other conventional additives such as antioxidants, buffers, and bacteriostatic agents may be added thereto. Further, when additionally adding a diluent, a dispersant, a surfactant, a binder, and a lubricant to the composition, the composition may be formulated into a formulation for injection such as an aqueous solution, a suspension, an emulsion, a pill, a capsule, a granule or a tablet. Furthermore, the composition may be preferably formulated based on each disease or component using a method appropriate in the art or by a method disclosed in Remington's Pharmaceutical Science (Mack Publishing Company, Easton Pa., 18th, 1990).

In one implementation, the pharmaceutical composition may be formulated into at least one selected from the group including oral dosage forms, external preparations, suppositories, sterile injectable solutions and sprays. Oral or injection formulations are more preferred.

The term "administration" as used in the present disclosure means providing a predetermined substance to a subject or patient in any appropriate way. Depending on the intended method, parenteral administration (for example, an injection formulation being applied in intravenous, subcutaneous, intraperitoneal manner or topically) or oral administration may be possible. The dosage range varies depending on the patient's weight, age, sex, health status, diet, administration time, administration method, excretion rate, and severity of disease. Liquid formulations for oral administration of the composition according to the present disclosure include suspensions, liquid solutions, emulsions, syrups, etc. In addition to water and liquid paraffin, which are commonly used simple diluents, various excipients such as wetting agents, sweeteners, fragrances, and preservative may be contained therein together. Formulations for parenteral administration include sterile aqueous solutions may include non-aqueous solvents, suspensions, emulsions, lyophilized formulations, suppositories, and the like. The pharmaceutical composition according to the present disclosure may be administered using any device capable of delivering the active substance to the target cell. Preferred modes of administration and formulations may be intravenous injections, subcutaneous injections, intradermal injections, intramuscular injections, drop injections and the like. Injectables may be prepared using aqueous solvents such as physiological saline and Ringer solutions, or non-aqueous solvents such as vegetable oils, higher fatty acid esters (e.g., oleic acid ethyl, etc.), alcohols (e.g., ethanol, benzyl alcohol, propylene glycol, glycerin, etc.). It may contain a pharmaceutical carrier such as stabilizers to prevent deterioration (e.g. ascorbic acid, sodium hydrogen sulfite, sodium pyro sulfite, BHA, tocopherol, EDTA, etc.), an emulsifier, a buffer for pH control, and a preservative for preventing the growth of microorganisms (e.g., phenyl mercury nitrate, thimerosal, benzalkonium chloride, phenol, cresol, benzyl alcohol, etc.).

As used in the present disclosure, the term "subject" refers to monkeys, cows, horses, sheep, pigs, chickens, turkeys, quails, cats, dogs, mice, rats, rabbits or guinea pigs, or humans who have the severe fever with thrombocytopenia syndrome. The "specimen" may be whole blood, plasma, serum, urine or saliva isolated therefrom.

The pharmaceutical composition according to the present disclosure may further contain pharmaceutically acceptable additives. The pharmaceutically acceptable additives include starch, gelatinized starch, microcrystalline cellulose, lactose, povidone, colloidal silicon dioxide, calcium hydrogen phosphate, lactose, mannitol, malt, arabic rubber, pregelatinized starch, corn starch, powdered cellulose, hydroxypropyl cellulose, opadry, sodium starch glycolate, lead carnauba, synthetic aluminum silicate, stearic acid, magnesium stearate, aluminum stearate, calcium stearate, sucrose, dextrose, sorbitol, talc, and the like. The pharmaceutically acceptable additive according to the present disclosure is preferably contained in 0.1 parts by weight to 90 parts by weight based on the composition, but is not limited thereto.

In one aspect, the present disclosure relates to an antibody produced in response to immunization using the virus or antigen thereof according to the present disclosure.

The antibody is not only in the form of a whole antibody, but also includes a functional fragment of an antibody molecule. The whole antibody has a structure having two full-length light chains and two full-length heavy chains, and each light chain is connected to a heavy chain via a disulfide bond. A functional fragment of an antibody molecule refers to a fragment that has an antigen-binding function. Examples of antibody fragments may include (i) a Fab fragment composed of a variable region (VL) of a light chain and a variable region (VH) of a heavy chain, a constant region (CL) of a light chain, and a first constant region (CH1) of a heavy chain; (ii) an Fd fragment composed of VH and CH1 domains; (iii) an Fv fragment composed of VL and VH domains of a single antibody; (iv) a dAb fragment composed of a VH domain (Ward E S et al., Nature 341:544-546 (1989)); (v) an isolated CDR region; (vi) an F(ab')2 fragment as a bivalent fragment containing two linked Fab fragments; (vii) a single chain Fv molecule (scFv) bound via a peptide linker that binds the VH domain and the VL domain to each other to form an antigen binding site; (viii) a bispecific single-chain Fv dimer (PCT/US92/09965); and (ix) a diabody as a polyvalent or multispecific fragment produced by gene fusion (WO94/13804), and the like.

In one aspect, the present disclosure relates to a diagnostic kit for the severe fever with thrombocytopenia syndrome virus, the kit containing the severe fever with thrombocytopenia syndrome virus or an antigen thereof, or an antibody against the same.

In one implementation, the kit may contain a virus sample containing the virus according to the present disclosure and a reagent for detecting an antigen-antibody complex. The reagent for detecting the antigen-antibody complex includes reagents for radioimmunoassay, ELISA (Enzyme linked immunosorbent assay) or immunofluorescence analysis.

In one embodiment, the detection of the antigen-antibody complex may be achieved using an Ouchterlony plate simply detecting the antibody and/or antigen via the antigen-antibody binding, western blot, and immuno electrophoresis such as Crossed IE, Rocket IE, Fused Rocket IE, and Affinity IE. Reagents or substances as used in this method are known. This may be detected, for example, via antigen-antibody reactions, or substrates, nucleic acids or peptide aptamers that specifically bind to antigens, or reactions with receptors, ligands, or cofactors interacting with the complex or using mass spectrometry. The reagent or substance that specifically interacts or binds to the antigen-antibody complex of the present application may be used in a chip method or in combination with nanoparticles. The immunoassay or immunostaining method is described in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, N J, 1984. Analyzing the intensity of the final signal by the above-described immunoassay process, that is, performing signal contrast with a normal sample may diagnose absence or presence of the infection of the disease.

In one aspect, the present disclosure relates to a diagnostic composition containing the severe fever with thrombocytopenia syndrome virus or antigen thereof, or an antibody against the antigen.

The compounds according to the present disclosure as used in the diagnostic composition are preferably labeled detectably. Various methods available for labeling biomolecules are well known to those skilled in the art and are considered within the category according to the present disclosure. The methods are described in Tijssen, 'Practice and theory of enzyme immuno assays', Burden, R H and von Knippenburg (Eds), Volume 15 (1985), 'Basic methods in molecular biology'; Davis L G, Dibmer M D; Battey Elsevier (1990), Mayer et al., (Eds) 'Immunochemical methods in cell and molecular biology' Academic Press, London (1987), or in the series 'Methods in Enzymology', Academic Press, Inc.

There are many other marking methods and makers known to the skilled person. Examples of the types of markers that may be used in the present disclosure may be enzymes, radioactive isotopes, colloidal metals, fluorescent compounds, chemiluminescent compounds, and bioluminescent compounds.

Commonly used markers include fluorescent substances (e.g., fluresin, rhodamine, Texas red, etc.), enzymes (e.g. horseradish peroxidase, β-galactosidase, alkaline phosphatase), radioactive isotopes (e.g., $^{32}P$ or $^{125}I$), biotin, digoxigenin, colloidal metal, chemiluminescent or bioluminescent compounds (e.g., dioxetane, luminol or acridinium). The marking methods such as methods based on covalent bonding of enzymes or biotinyl groups, iodination, phosphorylation, and biotinylation are well known in the art.

The detection methods may include autoradiography, fluorescence microscopy, direct and indirect enzyme reactions, etc. but is not limited thereto. A commonly used detection assay may be a radioactive isotope or non-radioactive isotope method. These may include Western blotting, overlay-analysis, Radioimmuno Assay (RIA) and Immuno Radioimmunometric Assay (IRMA), Enzyme Immuno Assay (EIA), Enzyme Linked Immuno Sorbent Assay (ELISA), Fluorescent Immuno Assay (FIA), and Chemioluminescent Immune Assay (CLIA).

In one aspect, the present disclosure relates to a method for detecting a severe fever with thrombocytopenia syndrome virus antibody, the method including contacting a sample isolated from a specimen with a virus or antigen thereof according to the present disclosure under a condition in which an antigen/antibody complex is able to be formed; and detecting formation of an antigen/antibody complex.

In one aspect, the present disclosure relates to a method for producing antiserum against the severe fever with thrombocytopenia syndrome virus in a non-human animal, the method including administering the virus or antigen thereof according to the present disclosure to the non-human animal at an amount effective to induce an immune response; and collecting antiserum or plasma containing an antibody against the severe fever with thrombocytopenia syndrome virus.

In one aspect, the present disclosure relates to a method for providing information regarding the diagnosis of the severe fever with thrombocytopenia syndrome, the method including contacting a sample isolated from a specimen with the virus or antigen thereof according to the present disclosure to form an antigen-antibody complex; and detecting the formation of the complex.

EXAMPLES

The present disclosure is described in more detail based on following Examples. However, the following Examples are intended only for specifying the present disclosure, and the present disclosure is not limited thereto.

Example 1. Virus Isolation

Blood from patients who visited university hospitals and were suspected of having symptoms of severe fever thrombocytopenia syndrome, and bloods from animals (goat and abandoned dogs) suspected of having symptoms of severe fever thrombocytopenia syndrome, and wild mite homogenate were used to identify whether the SFTSV (severe fever thrombocytopenia syndrome virus) thereof is positive/negative via real-time PCR, PCR and ELISA analysis. Specifically, a day before virus infection, VeroE6 cells were dispensed into a 12-well plate, cultured so that the cell density exceeded 60%, and the cells were washed with PBS. The cells were treated with 300 µl of serum from a suspected infected patient (serum obtained by centrifuging whole blood at 3000 rpm for 20 minutes) for 1 hour to infect the cells. After the infection, the serum was removed, and the cells were washed with PBS, and then the cells were exchanged with 1% FBS DMEM medium and cultured in 1% FBS DMEM medium for 2 weeks. The two weeks later, RT-PCR (identification via real-time PCR after reverse transcription) and immune fluorescence assay (in which a mouse SFTSV NP antibody produced in a laboratory was used as the primary antibody and the antibody conjugated with FITC was used as the secondary antibody) were used to identify the presence or absence of the virus isolation. When the virus was not isolated, the virus was isolated by infecting another VeroE6 cell with the first infected supernatant. The isolated viruses were named as CB3/2016, CB7/2017 and CB6/2016.

Example 2. Genetic Analysis of Isolated Virus

The viruses CB3/2016, CB7/2017 and CB6/2016 isolated using Vero E6 cells were respectively reverse-transcribed, and then subjected to PCR, and NGS (next generation sequencing) to identify L, M, S (NP, NS) whole gene sequences thereof. Specifically, RNA was extracted from each virus, and cDNA was produced through reverse-transcription PCR. Subsequently, the L, M, and S genes of each SFTS virus were subjected to PCR to obtain each whole gene. The NGS method was used for gene sequence analysis. The L, M, and S genes of each virus were subjected to tagmentation and index PCR using an illumina nextera XT kit according to the protocol provided from illumina. Afterwards, Fasta Q file of the final sample was generated using the illimina miniseq equipment. The whole gene sequence of the generated file was analyzed using the CLC main workbench program. We integrated the identified gene sequences with the genes of conventional viruses isolated in Korea, China and Japan, and then performed genetic analysis. Thus, it was identified that the SFTSVs CB1, CB3 and CB4 as isolated according to the present disclosure are new genotypes of SFTSV genetically different from the genes of the viruses currently isolated in China or Korea (Yu X J et al., N. Engl. J. Med. 2011) and the virus first isolated in Korea (Gangwon/2012). In addition, it was identified based on a result of a phylogenetic gene analysis of L, M, and S (NP, NS) genes of viruses according to the present disclosure and viruses isolated from Korea, China, and Japan using the MEGA 7.0 program, that the viruses according to the present disclosure were close to the group B which most of the domestic isolated viruses belong to, but the genes L, M and S (NP and NS) thereof are different from those of the conventional viruses. Thus, we identified that the viruses according to the present disclosure is subdivided into at least 3 or more groups (FIG. 1 to FIG. 4). Accordingly, the three genotype SFTSVs isolated according to the present disclosure as subdivided were named B-1 (CB3/2016), B-2 (CB7/2017) and B-3 (CB6/2016), respectively.

Figure 5:
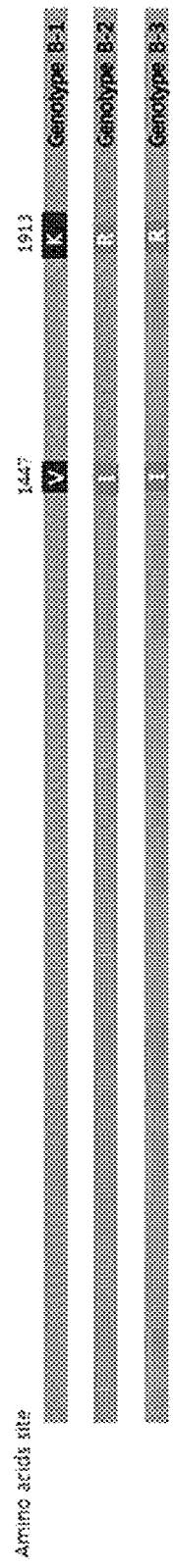
FIG. 5 shows amino acid mutation sites in L and M genes of three novel viruses of genotypes B-1 (CB3/2016), B-2 (CB7/2017) and B-3 (CB6/2016) according to the present disclosure.
Figure 5:
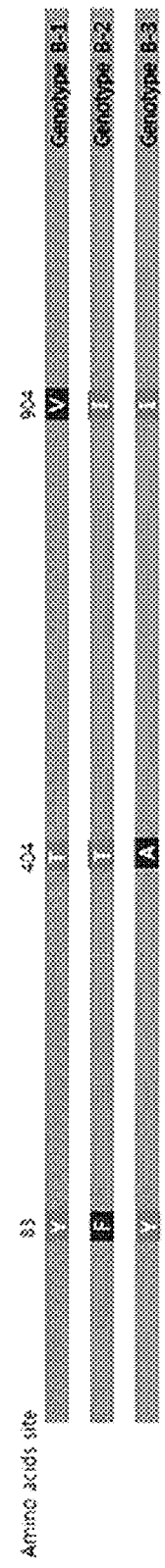

Example 3. Identification of Differences in Amino Acid Sequence of L, M and S Genes by Viruses 3-1. L Gene Amino Acid Sequence Difference It was identified based on a result of analyzing an amino acid sequence based on the open reading frame (ORF) of each of the L, M and S genes of the viruses of the novel subdivided genotypes B-1, B-2 and B-3 isolated according to the present disclosure, that the L and M genes were different from those in the conventional virus. Specifically, ORF (6255 bp) of an L gene in the B genotype encodes RdRp. In the genotype B-1 virus according to the present disclosure, the 1447-th amino acid of RdRp was valine or the 1913-rd amino acid thereof was lysine. In the genotype B-2 virus and B-3 virus according to the present disclosure, the 1447-th amino acid of RdRp was isoleucine or the 1913-rd amino acid thereof was arginine (FIG. 5A and Table 1).

TABLE 1

| Amino Acids site | L gene | | M gene | | |
|---|---|---|---|---|---|
| | 1447 | 1913 | 83 | 404 | 904 |
| B-1 type | Val | Lys | Tyr | Thr | Val |
| B-2 type | Ile | Arg | Phe | Thr | Ile |
| B-3 type | Ile | Arg | Tyr | Ala | Ile |

3-2. M Gene Amino Acid Sequence Difference

It was identified based on a result of analyzing an amino acid sequences of the L, M and S genes of the viruses of the new subdivided genotypes B-1, B-2 and B-3 isolated in accordance with the present disclosure, the L and M genes were different from those in the conventional virus. Specifically, ORF (3222 bp) of an M gene in the B genotype encodes Gn and Gc proteins. According to the present disclosure, in the genotype B-1 virus, the 83-rd amino acid of ORF of an M gene was tyrosine, the 404-th amino acid thereof was threonine or the 904-th amino acid thereof was valine. In the genotype B-2 virus, the 83-rd amino acid of ORF of an M gene was phenylalanine, the 404-th amino acid thereof was threonine or the 904-th amino acid thereof was isoleucine. In the genotype B-3 virus, the 83-rd amino acid of ORF of an M gene was tyrosine, the 404-th amino acid thereof was alanine, or the 904-th amino acid thereof was isoleucine (FIG. 5B and Table 1).

Example 4. Comparison of Gene Homology Based on Genotype

SFTSVs currently isolated in Korea and SFTSVs of the subdivided genotypes B-1, B-2 and B-3 according to the present disclosure were subjected to genetic analysis. The homology of L, M and S genes based on each genotype was compared and analyzed. As a result, about 96% to 100% of the gene homology (nucleotide level) between the viruses belonging to the same genotype was observed, while 91% to 97% of a relatively low gene homology between different genotype viruses was observed (Tables 2 to 5). Further, in the genotype B-3 group according to the present disclosure, the homology within the same group exhibited a relatively low homology at a level of about 95% to 100%. Thus, the possibility of subdividing the B-3 group into different genotype groups was identified.

TABLE 2

| | Sequence homology (%) (Nucleotide identity) | | |
|---|---|---|---|
| Genotype | B-1 | B-2 | B-3 |
| B-1 | 96.4~100.0% | 96.0~97.4% | 95.9~97.1% |
| B-2 | 98.6~99.6% | 97.2~100.0% | 96.2~97.1% |
| B-3 | 98.1~99.8% | 98.2~99.9% | 96.5~100.0% |

Comparison of Homology of L Gene

TABLE 3

| | Sequence homology (%) (Nucleotide identity) | | |
|---|---|---|---|
| Genotype | B-1 | B-2 | B-3 |
| B-1 | 95.8~100.0% | 94.5~97.1% | 93.2~96.8% |
| B-2 | 98.3~99.6% | 95.7~100.0% | 93.7~96.8% |
| B-3 | 94.8~99.3% | 95.3~99.7% | 94.4~100.0% |

Comparison of Homology of M Gene

TABLE 4

| | Sequence homology (%) (Nucleotide identity) | | |
|---|---|---|---|
| Genotype | B-1 | B-2 | B-3 |
| B-1 | 95.8~100.0% | 94.5~97.1% | 93.2~96.8% |
| B-2 | 98.3~99.6% | 95.7~100.0% | 93.7~96.8% |
| B-3 | 94.8~99.3% | 95.3~99.7% | 94.4~100.0% |

Comparison of Homology of S (NP) Gene

TABLE 5

| Genotype | Sequence homology (%) (Nucleotide identity) | | |
|---|---|---|---|
| | B-1 | B-2 | B-3 |
| B-1 | 95.8~100.0% | 94.8~97.4% | 94.3~96.8% |
| B-2 | 98.9~100.0% | 95.1~100.0% | 94.8~98.2% |
| B-3 | 96.2~100.0% | 94.9~100.0% | 96.1~100.0% |

Comparison of Homology of S (NS) Gene

Example 5. Cross Immunogenic Analysis and Vaccine Effect Identification Based on Genotype 5-1. Cross Immunogenic Analysis Based on Genotype In order to compare and analyze cross immunogenicity based on each genotype, a fifty percent of focus reduction neutralization test (FRNT50) was performed. Specifically, we carried out mass proliferation of viruses of the new subdivided genotype B-1, B-2 and B-3 as isolated according to the present disclosure, and then carried out inactivation thereof by adding formalin (0.05%) thereto, and then identified occurrence or non-occurrence of the inactivation thereof via 3 times virus isolations. The inactivated whole vaccines were used to produce proteins via ultracentrifugation using 20% sucrose. The proteins were immunized into ferrets. After 2 weeks, additional immunization was performed on the ferrets (two times immunizations, 2 weeks intervals), and the blood was collected therefrom and the serum was separated therefrom. The separated serum was inactivated at 56° C. for 30 minutes, diluted to ⅒, and then serially diluted 2 times. The virus diluted with 200 FFU/ml was reacted with the virus as serially diluted at 37° C. at 1:1. After washing the VeroE6 cells as dispensed in a 6-well plate, the cells were infected with the reacted virus. One hour thereafter, we performed washing of the cells. Then, the cells were immersed in 0.8% DMEM agarose gel containing 1% FBS. 5 days after the infection, formalin was used to fix the cells, and 3 hours thereafter, three washes were performed, followed by treatment with 10% triton x-100 for 5 minutes at room temperature. Then, the cells were washed 3 times and blocking thereof was performed with 5% BSA. After incubation of the cells using a produced polyclonal NP antibody as a primary antibody, the cells were washed three times, and the cells were reacted with the HRP conjugated antibody as a secondary antibody for 1 hour, and then were washed, and then colored with DAB to identify the coloring result. The result was interpreted such that up to a value reduced by 50% compared to that of the focus forming of the well infected with only the virus was effective.

TABLE 6

| Virus | Serum | | |
|---|---|---|---|
| | B-1 | B-2 | B-3 |
| B-1 | 1280 | 1280 | 320 |
| B-2 | 640 | 2560 | 320 |
| B-3 | 640 | 640 | 640 |

It was found based on the result of identifying cross-immunogenicity of the B-1, B-2, and B-3, the highest titer was found for each virus as shown in the Table 6. Thus, the viruses belonging to the same genotype exhibited high cross-neutralization reactivity, but the viruses belonging to different genotypes exhibited relatively low cross-neutralization reactivity.

5-2. Vaccine Effectiveness Identification

After proliferating the viruses of the new subdivided genotypes B-1, B-2 and B-3 isolated according to the present disclosure in large quantities, formalin (0.05%) was added thereto to inactivate each virus. Then, whether each virus was successfully inactivated was checked via three times virus isolations. Each of the inactivated whole vaccine was immunized into 5 ferrets twice at 2 weeks intervals, and the ferrets were challenged at $1\times10^{7.6}$/ml for each virus.

Figure 6:
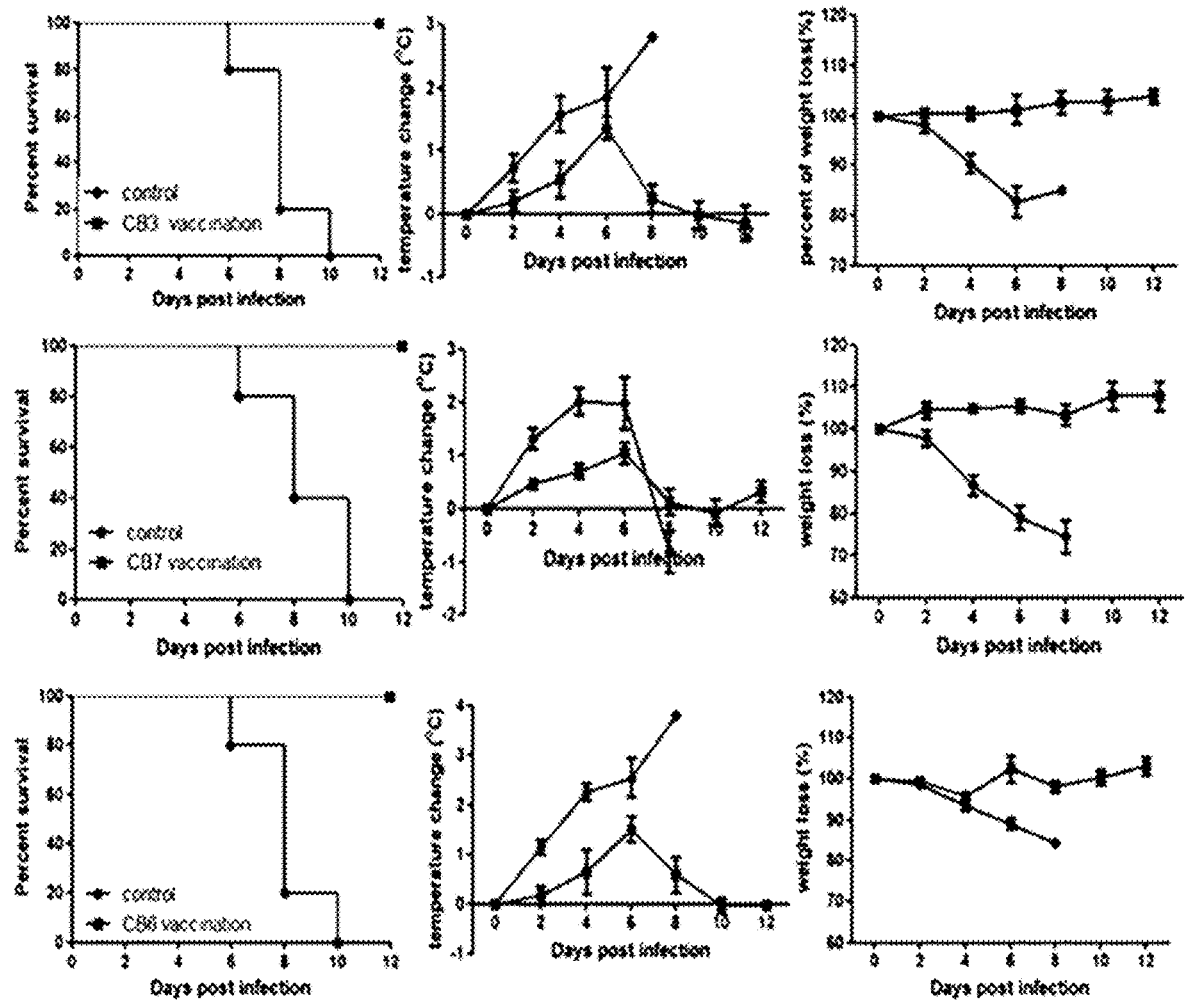
FIG. 6 is a diagram that identifies vaccine effects of three novel viruses of genotypes B-1 (CB3/2016), B-2 (CB7/2017) and B-3 (CB6/2016) according to the present disclosure.

It was identified based on the result of the attack challenge that the control animals died within 10 days of all challenge attack virus infections, but all ferrets of the vaccinated group survived. Body temperature increase and weight loss were identified 2 to 8 days after the infection. Thereafter, they were recovered (FIG. 6).

Summarizing the above results, there are various genotypes of viruses having various genes in SFTSV. The viruses belonging to the same genotype exhibited the relatively high gene homology and high cross-immune response, but the viruses of the different genotypes exhibited the relatively low gene homology and low cross-immunogenicity. Thus, it may be inferred that in order to exhibit the cross-immunogenicity between the various genotypes, only a specific genotype of virus may exhibit limited protective ability.

Therefore, the new viruses CB3/2016, CB7/2017 and CB6/2016 belonging to the subdivided genotypes B-1, B-2 and B-3 according to the present disclosure respectively are useful as vaccines having excellent cross immunogenicity with the SFTSV of the genotype B.

The invention claimed is:

1. An immunogenic composition for prevention or treatment of a severe fever with thrombocytopenia syndrome, comprising inactivated severe fever with thrombocytopenia syndrome virus or a gene thereof as an active ingredient, and an adjuvant,
   wherein the severe fever with thrombocytopenia syndrome virus or the gene thereof comprises:
   (i) a L gene that encodes a protein having the sequence of SEQ ID NO: 17, and a M gene that encodes a protein having the sequence of SEQ ID NO: 18, or
   (iii) a L gene that encodes a protein having the sequence of SEQ ID NO: 21, and a M gene that encodes a protein having the sequence of SEQ ID NO: 22.

2. The composition of claim 1, wherein the composition further comprises a pharmaceutically acceptable carrier.

3. The composition of claim 1, wherein the immunogenic composition contains, as an active ingredient:
   a severe fever with thrombocytopenia syndrome virus containing an L gene containing a base sequence represented by SEQ ID NO: 5, an M gene containing a base sequence represented by SEQ ID NO: 6, an NP gene containing a base sequence represented by SEQ ID NO: 7, and an NS gene containing a base sequence represented by SEQ ID NO: 8; or
   a severe fever with thrombocytopenia syndrome virus containing an L gene containing a base sequence represented by SEQ ID NO: 9, an M gene containing a base sequence represented by SEQ ID NO: 10, an NP gene containing a base sequence represented by SEQ ID NO: 11, and an NS gene containing a base sequence represented by SEQ ID NO: 12.

4. A method for detecting a severe fever with thrombocytopenia syndrome virus antibody, the method comprising:
   (a) contacting a sample isolated from a specimen with severe fever with thrombocytopenia syndrome virus or a gene thereof under a condition in which an antigen-antibody complex is able to be formed; and
   (b) detecting the formation of the antigen-antibody complex,
   wherein the severe fever with thrombocytopenia syndrome virus, or the gene thereof comprises
   (i) a L gene that encodes a protein having the sequence of SEQ ID NO: 17, and a M gene that encodes a protein having the sequence of SEQ ID NO: 18, or
   (iii) a L gene that encodes a protein having the sequence of SEQ ID NO: 21, and a M gene that encodes a protein having the sequence of SEQ ID NO: 22.

5. A method for producing antiserum against a severe fever with thrombocytopenia syndrome virus in a non-human animal, the method comprising:
   (a) administering severe fever with thrombocytopenia syndrome virus or a gene thereof to the non-human animal at an amount effective to induce an immune response; and
   (b) collecting antiserum or plasma containing an antibody against the severe fever with thrombocytopenia syndrome virus,
   wherein the severe fever with thrombocytopenia syndrome virus or the gene thereof comprises
   (i) a L gene that encodes a protein having the sequence of SEQ ID NO: 17, and a M gene that encodes a protein having the sequence of SEQ ID NO: 18, or
   (iii) a L gene that encodes a protein having the sequence of SEQ ID NO: 21, and a M gene that encodes a protein having the sequence of SEQ ID NO: 22.

* * * * *